(12) United States Patent
Linder et al.

(10) Patent No.: US 9,795,697 B2
(45) Date of Patent: Oct. 24, 2017

(54) LIQUID CONTAINMENT FOR INTEGRATED ASSAYS

(75) Inventors: Vincent Linder, Tewksbury, MA (US); David Steinmiller, Menlo Park, CA (US); Jason Taylor, Windham, NH (US)

(73) Assignee: OPKO Diagnostics, LLC, Woburn, MA (US)

( * ) Notice: Subject to any disclaimer, the term of this patent is extended or adjusted under 35 U.S.C. 154(b) by 39 days.

(21) Appl. No.: 12/196,392

(22) Filed: Aug. 22, 2008

(65) Prior Publication Data

US 2009/0075390 A1 Mar. 19, 2009

Related U.S. Application Data

(60) Provisional application No. 60/994,412, filed on Sep. 19, 2007.

(51) Int. Cl.
*G01N 30/00* (2006.01)
*C12M 1/34* (2006.01)
(Continued)

(52) U.S. Cl.
CPC ....... *A61L 2/0082* (2013.01); *B01L 3/502715* (2013.01); *B01L 3/502784* (2013.01);
(Continued)

(58) Field of Classification Search
CPC combination set(s) only.
See application file for complete search history.

(56) References Cited

U.S. PATENT DOCUMENTS 5,147,607 A 9/1992 Mochida
5,286,454 A 2/1994 Nilsson et al.
(Continued)

FOREIGN PATENT DOCUMENTS

EP 0110771 B1 6/1984
EP 0 281 201 9/1988
(Continued)

OTHER PUBLICATIONS

International Search Report from International Application No. PCT/US2008/010022, dated May 6, 2009.
(Continued)

*Primary Examiner* — Dirk Bass
(74) *Attorney, Agent, or Firm* — Wolf, Greenfield & Sacks, P.C.

(57) ABSTRACT

Microfluidic systems including liquid containment regions and methods associated therewith for performing chemical, biological, or biochemical analyzes are provided. Liquid containment regions of a microfluidic device may include regions that capture one or more liquids flowing in the device, while allowing gases or other fluids in the device to pass through the region. This may be achieved, in some embodiments, by positioning one or more absorbent materials in the liquid containment region for absorbing the liquids. This configuration may be useful for removing air bubbles from a stream of fluid and/or for separating hydrophobic liquids from hydrophilic liquids. In certain embodiments, the liquid containment region prevents any liquid from passing through the region. In some such cases, the liquid containment region may act as a waste area by capturing substantially all of the liquid in the device, thereby preventing any liquid from exiting the device. This arrangement may be useful when the device is used as a diagnostic tool, as the liquid containment region may prevent a user from being exposed to potentially-harmful fluids in the device.

38 Claims, 25 Drawing Sheets

(51) Int. Cl.
*A61L 2/00* (2006.01)
*B01L 3/00* (2006.01)

(52) U.S. Cl.
CPC . *B01L 2200/025* (2013.01); *B01L 2200/0673* (2013.01); *B01L 2300/069* (2013.01); *B01L 2300/087* (2013.01); *B01L 2300/0816* (2013.01); *B01L 2300/161* (2013.01); *B01L 2400/0406* (2013.01); *B01L 2400/0487* (2013.01)

(56) References Cited

U.S. PATENT DOCUMENTS

| | | | |
|---|---|---|---|
| 6,019,944 | A | 2/2000 | Buechler |
| 6,168,948 | B1 | 1/2001 | Anderson et al. |
| 6,416,642 | B1 | 7/2002 | Alajoki et al. |
| 6,488,894 | B1 | 12/2002 | Miethe et al. |
| 6,610,499 | B1 | 8/2003 | Fulwyler et al. |
| 6,632,619 | B1 | 10/2003 | Harrison et al. |
| 6,716,620 | B2 | 4/2004 | Bashir et al. |
| 6,818,184 | B2 | 11/2004 | Fulwyler et al. |
| 6,858,185 | B1 | 2/2005 | Kopf-Sill et al. |
| 6,989,128 | B2 | 1/2006 | Alajoki et al. |
| 7,015,046 | B2 | 3/2006 | Wohlstadter et al. |
| 7,087,148 | B1 | 8/2006 | Blackburn et al. |
| 2002/0142618 | A1 | 10/2002 | Parce et al. |
| 2003/0152927 | A1* | 8/2003 | Jakobsen et al. ............. 435/6 |
| 2003/0185713 | A1 | 10/2003 | Leonard et al. |
| 2005/0221281 | A1 | 10/2005 | Ho |
| 2006/0002827 | A1 | 1/2006 | Curcio et al. |
| 2006/0257992 | A1 | 11/2006 | McDevitt et al. |
| 2006/0275852 | A1 | 12/2006 | Montagu et al. |
| 2008/0038839 | A1* | 2/2008 | Linder et al. ............. 436/501 |
| 2009/0181411 | A1* | 7/2009 | Battrell et al. ............. 435/7.92 |

FOREIGN PATENT DOCUMENTS

| | | |
|---|---|---|
| EP | 0 430 248 | 6/1991 |
| EP | 0 430 248 A2 | 6/1991 |
| EP | 1 054 259 A1 | 11/2000 |
| JP | 2006-329901 | 7/2006 |
| WO | WO 88/06731 A1 | 9/1988 |
| WO | WO 89/00697 A2 | 1/1989 |
| WO | WO 91/01003 A | 1/1991 |
| WO | WO 04/087951 A2 | 10/2004 |
| WO | WO 2005/072858 | 8/2005 |
| WO | WO 2006056787 A1 | 6/2006 |
| WO | WO 2006/101851 A2 | 9/2006 |

OTHER PUBLICATIONS

Japanese Office Action for JP 2010-525801, dated Nov. 1, 2012.
Linder, et al., "Reagent-Loaded Cartridges for Valveless and Automated Fluid Delivery in Microfluidic Devices," *Anal Chem*, vol. 77, No. 1, (2005) pp. 64-71.
Obeid et al., "Microfabricated device for DNA and RNA amplification by continuous-flow polymerase chain reaction and reverse transcription-polymerase chain reaction with cycle number selection", *Anal. Chem.*, vol. 75, No. 2, (2003) pp. 288-295.
Song et al., "A microfluidic system for controlling reaction networks in time", *Angew. Chem. Int. Ed.*, vol. 42, No. 7, (2003) pp. 767-772.

* cited by examiner

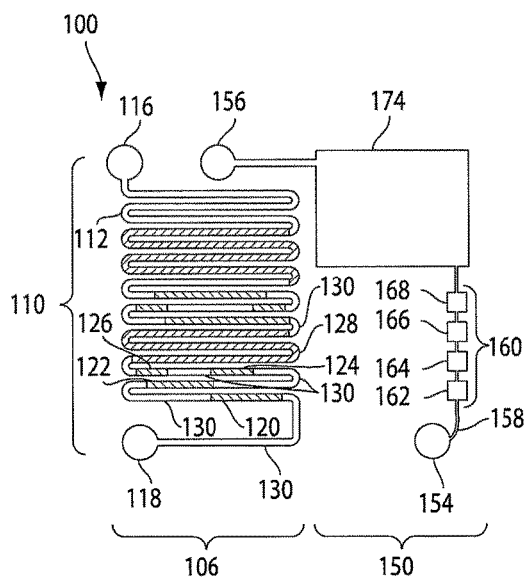
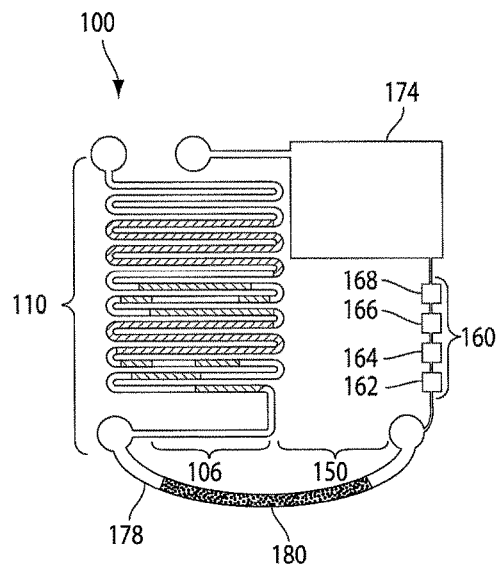
Fig. 3A  Fig. 3B
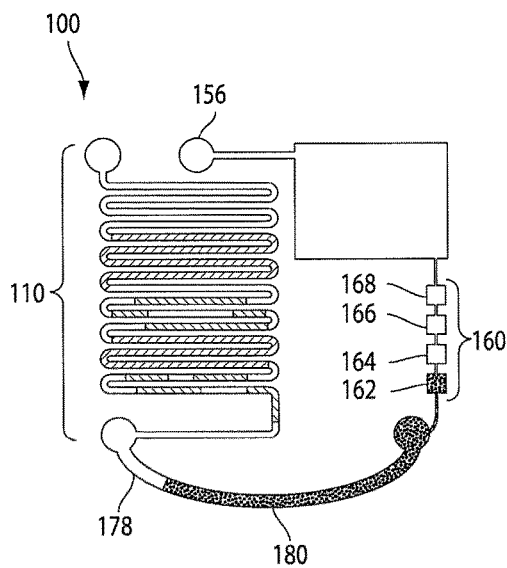
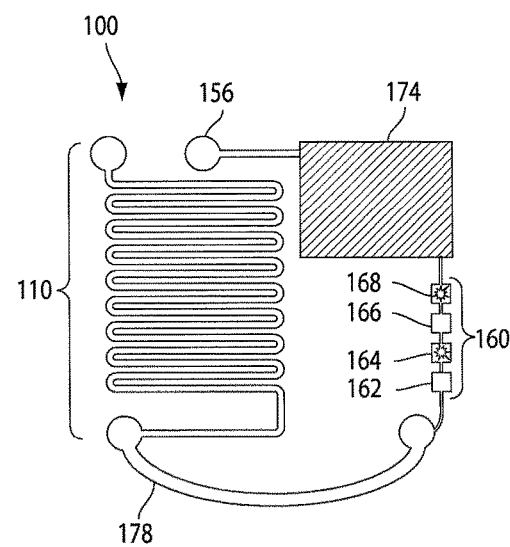
Fig. 3C  Fig. 3D

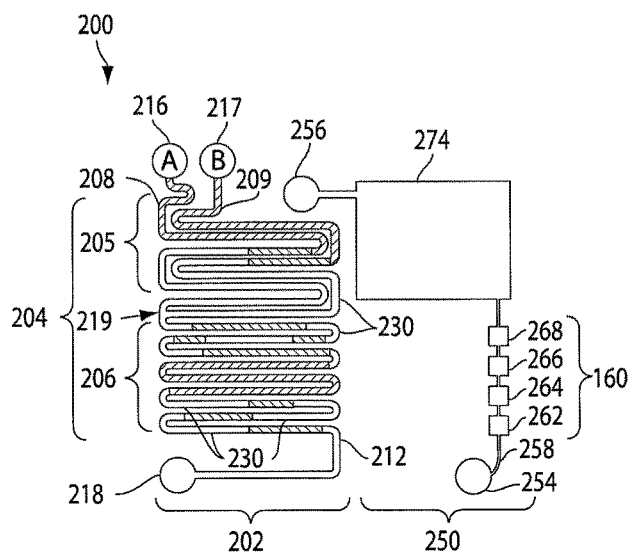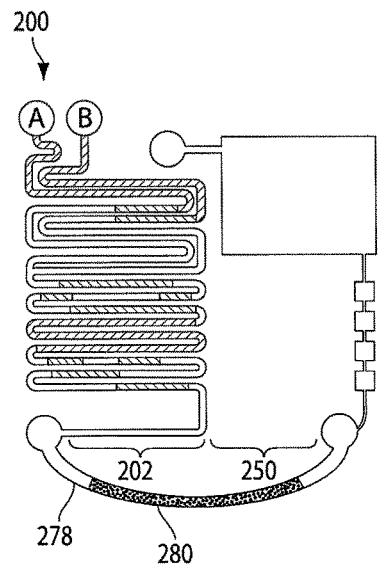
Fig. 4A
Fig. 4B
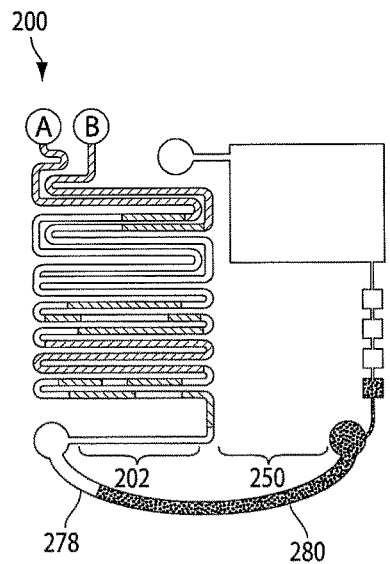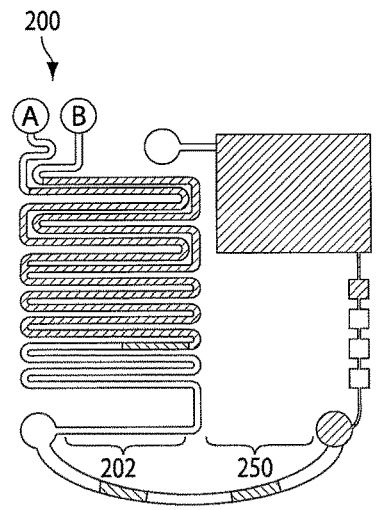
Fig. 4C
Fig. 4D

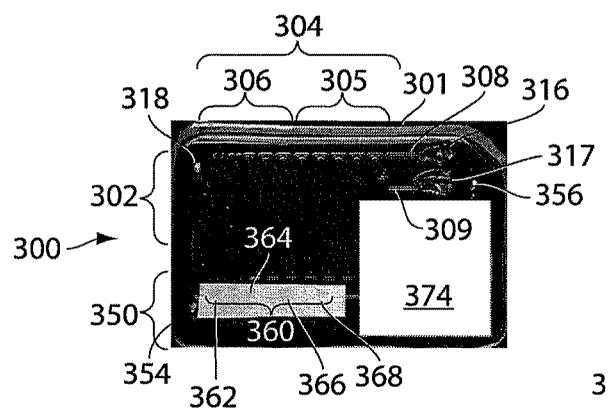
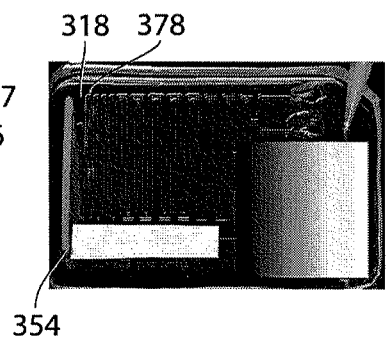
Fig. 5A    Fig. 5B
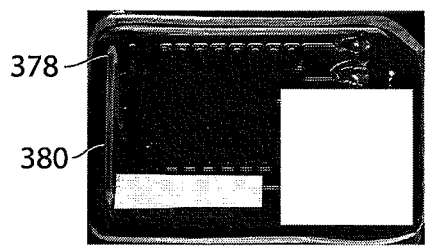
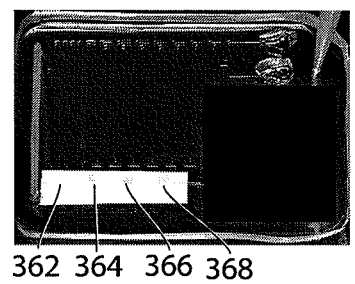
Fig. 5C    Fig. 5D
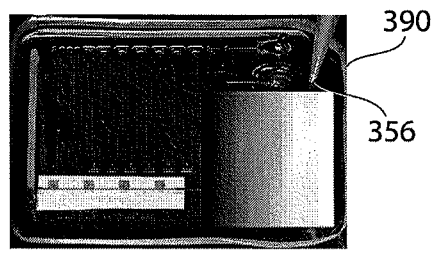
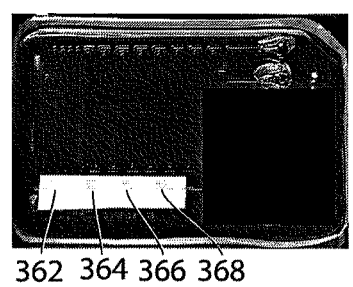
Fig. 5E    Fig. 5F

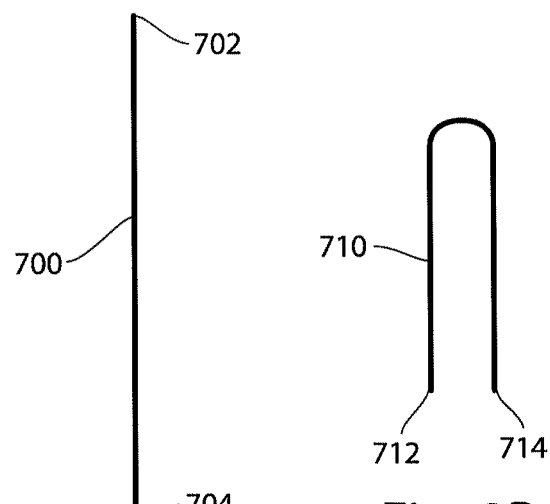
Fig. 8A
Fig. 8B
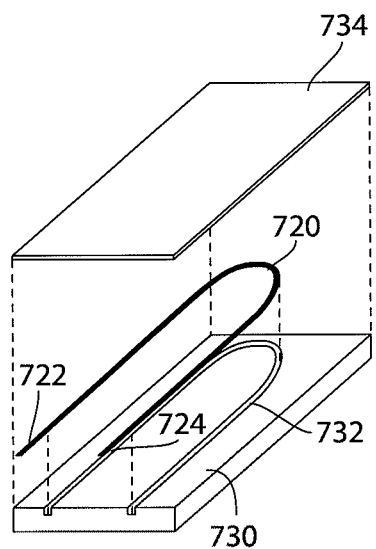
Fig. 8C
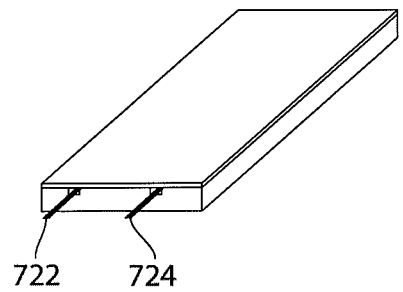
Fig. 8D

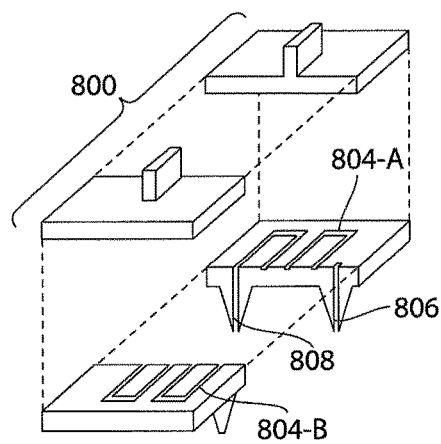
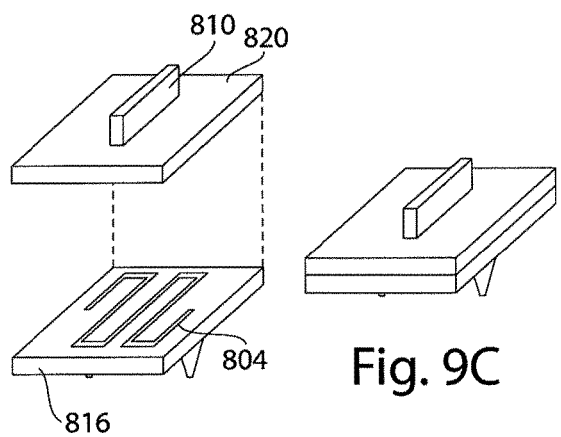
Fig. 9A      Fig. 9B      Fig. 9C
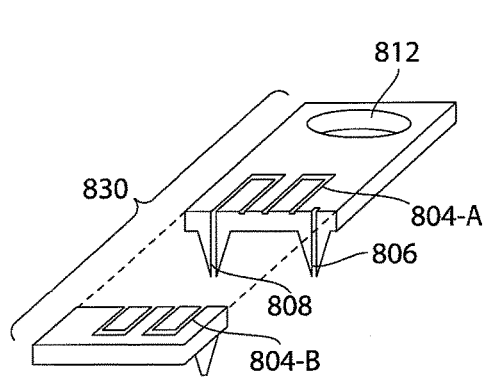
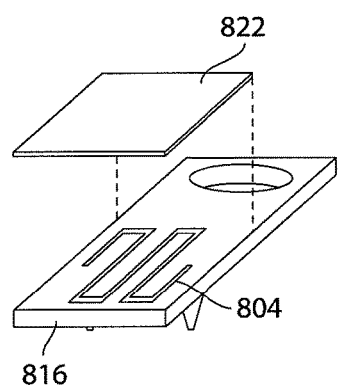
Fig. 9D      Fig. 9E
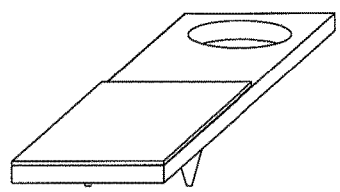
Fig. 9F

LIQUID CONTAINMENT FOR INTEGRATED ASSAYS

RELATED APPLICATIONS

This application claims priority under 35 U.S.C. 119(e) to U.S. Provisional Patent Application No. 60/994,412, filed Sep. 19, 2007, and entitled "Liquid containment for integrated assays", which is incorporated herein by reference.

FIELD OF INVENTION

The present invention relates generally to microfluidic systems and components thereof, and more specifically, to systems including liquid containment regions and methods associated therewith for performing chemical, biological, or biochemical analyses.

BACKGROUND

The manipulation of fluids plays an important role in fields such as chemistry, microbiology and biochemistry. These fluids may include liquids or gases and may provide reagents, solvents, reactants, or rinses to chemical or biological processes. While various microfluidic methods and devices, such as microfluidic assays, can provide inexpensive, sensitive and accurate analytical platforms, fluid manipulations-such as sample introduction, introduction of reagents, storage of reagents, separation of fluids, collection of waste, extraction of fluids for off-chip analysis, and transfer of fluids from one chip to the next—can add a level of cost and sophistication. Accordingly, advances in the field that could reduce costs, simplify use, and/or improve fluid manipulations in microfluidic systems would be beneficial.

SUMMARY OF THE INVENTION

Microfluidic systems including liquid containment regions and methods associated therewith for performing chemical, biological, or biochemical analyses are provided.

In one aspect, a series of methods are provided. In one embodiment, a method comprises establishing flow of a first plug comprising a first liquid and a second plug comprising a second liquid in a channel of a device including a microfluidic network, wherein the first and second plugs are separated by a fluid immiscible with the first and second liquids and contacting at least a portion of the first liquid and/or the second liquid with a reaction area of the network. The method also includes absorbing at least a portion of the first liquid and/or the second liquid with an absorbent material contained in a liquid containment region positioned downstream of the reaction area, the containment region in fluid communication with the channel, and controlling a rate of flow of a liquid in the channel, wherein the act of absorbing does not substantially modulate the flow rate of a liquid flowing in the channel upstream of the liquid containment region.

In another embodiment, a method comprises establishing flow of a first liquid in a channel of a device comprising a microfluidic network, causing a chemical and/or biological reaction to occur between a first component contained in the first liquid and a second component immobilized at a reaction area in fluid communication with the channel, and passing a wash solution across the reaction area. The method also includes absorbing at least a portion of the first liquid with an absorbent material contained in a liquid containment region in fluid communication with the channel, and controlling a rate of flow of a liquid in the channel, wherein the act of absorbing does not substantially modulate the flow rate of a liquid flowing in the channel upstream of the liquid containment region.

In another aspect, a series of devices including a microfluidic network are provided. In one embodiment, a device comprises a reservoir associated with the device, the reservoir containing a first liquid reagent stored therein prior to use of the device, in fluid communication with a first channel, and a reaction area in fluid communication with the first channel during use of the device. The device also includes an absorbent material contained in a liquid containment region positioned downstream of the reaction area and in fluid communication with the reaction area during use of the device, an outlet positioned downstream of the liquid containment region, and a connecting channel fluidly connecting the outlet with the liquid containment region.

In another embodiment, a device including a microfluidic network comprises a first channel and a reaction area in fluid communication with the first channel. The device also includes an absorbent material and a disinfectant stored in a liquid containment region prior to use of the device, the liquid containment region positioned downstream of the reaction area and in fluid communication with the reaction area during use of the device.

Other advantages and novel features of the present invention will become apparent from the following detailed description of various non-limiting embodiments of the invention when considered in conjunction with the accompanying figures. In cases where the present specification and a document incorporated by reference include conflicting and/or inconsistent disclosure, the present specification shall control. If two or more documents incorporated by reference include conflicting and/or inconsistent disclosure with respect to each other, then the document having the later effective date shall control.

BRIEF DESCRIPTION OF THE DRAWINGS

Non-limiting embodiments of the present invention will be described by way of example with reference to the accompanying figures, which are schematic and are not intended to be drawn to scale. In the figures, each identical or nearly identical component illustrated is typically represented by a single numeral. For purposes of clarity, not every component is labeled in every figure, nor is every component of each embodiment of the invention shown where illustration is not necessary to allow those of ordinary skill in the art to understand the invention. In the figures:

FIGS. 3A-3D are schematic diagrams of a microfluidic device including a fluidic connector and containing stored reagents used to perform a chemical and/or biological reaction according to an embodiment of the invention;

FIGS. 4A-4D are schematic diagrams of a microfluidic device including a fluidic connector and containing stored reagents used to perform a chemical and/or biological reaction according to an embodiment of the invention;

FIGS. 5A-5F are photographs of a microfluidic device including a fluidic connector used to perform a chemical and/or biological reaction according to an embodiment of the invention;

FIGS. 8A-8D are schematic diagrams of an open-ended fluidic device and fluidic connectors according to an embodiment of the invention;

FIGS. 9A-9F are schematic diagrams of monolithic fluidic connectors according to an embodiment of the invention;

DETAILED DESCRIPTION

Figure 1A:
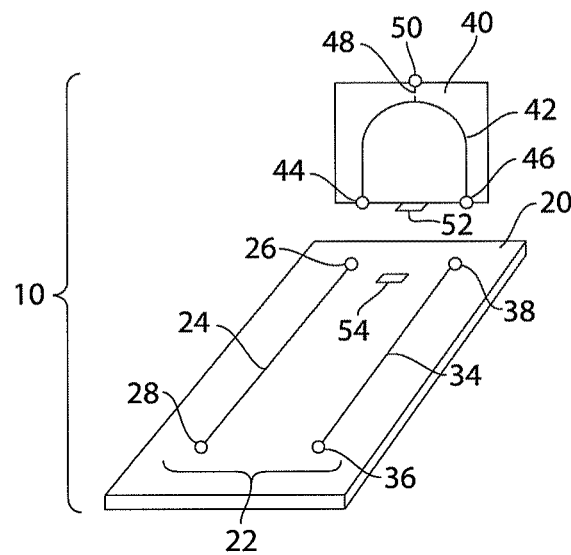
FIGS. 1A and 1B are schematic diagrams of a microfluidic device including a fluidic connector according to an embodiment of the invention.

Microfluidic systems including liquid containment regions and methods associated therewith for performing chemical, biological, or biochemical analyses are provided. Liquid containment regions of a microfluidic device may include regions that capture one or more liquids flowing in the device, while allowing gases or other fluids in the device to pass through the region. This may be achieved, in some embodiments, by positioning one or more absorbent materials in the liquid containment region for absorbing the liquids. This configuration may be useful for removing air bubbles from a stream of fluid and/or for separating hydrophobic liquids from hydrophilic liquids. In certain embodiments, the liquid containment region prevents any liquid from passing through the region. In some such cases, the liquid containment region may act as a waste area by capturing substantially all of the liquid in the device, thereby preventing any liquid from exiting the device. This arrangement may be useful when the device is used as a diagnostic tool, as the liquid containment region may prevent a user from being exposed to potentially-harmful fluids in the device.

In another aspect of the invention, fluidic connectors, methods, and devices for performing analyses (e.g., immunoassays) in microfluidic systems are provided. In some embodiments, a fluidic connector having a fluid path is used to connect two independent channels formed in a substrate so as to allow fluid communication between the two independent channels. One or both of the independent channels may be pre-filled with reagents (e.g., antibody solutions, washing buffers and amplification reagents), which can be used to perform the analysis. These reagents may be stored in the channels of the substrate for long periods amounts of time (e.g., 1 year) prior to use. Prior to connection of the fluid connector and the substrate, the fluid path may be filled with a sample (e.g., blood). The sample may be obtained, for example, by pricking a finger of a user until blood is drawn from the finger into the fluid path (e.g., by capillary forces). Upon connection of the fluidic connector and the channels of the substrate, the sample can pass through a reaction area within the first channel of the substrate. This process can allow components of the sample to interact with components disposed in the reaction area. Afterwards, reagents from the second channel can flow to the reaction area via the fluid path, allowing components in the reaction area to be processed (e.g., amplified to produce detectable signal). Components in the reaction area can then be determined using various methods of detection.

Microfluidic systems described herein may be useful for performing chemical and/or biological reactions, especially immunoassays, with one or more advantages such as: (a) use of small amounts of sample with little or no sample waste, (b) long-term stability of chemical and/or biological reagents stored in the device, (c) reduction of cross-contamination between stored reagents and/or between sample and reagent, (d) sample metering, (e) ease of use to untrained users for introducing a sample into the device, (f) efficient mixing of reagents, and (g) assay reliability. These and other advantages are described in more detail below in connection with the description and figures.

The articles, systems, and methods described herein may be combined with those described in International Patent Publication No. WO2005/066613 (International Patent Application Serial No. PCT/US2004/043585), filed Dec. 20, 2004 and entitled "Assay Device and Method," International Patent Publication No. WO2005/072858 (International Patent Application Serial No. PCT/US2005/003514), filed Jan. 26, 2005 and entitled "Fluid Delivery System and Method," International Patent Publication No. WO2006/113727 (International Patent Application Serial No. PCT/US06/14583), filed Apr. 19, 2006 and entitled "Fluidic Structures Including Meandering and Wide Channels," U.S. patent application Ser. No. 12/113,503, filed May 1, 2008 and entitled "Fluidic Connectors and Microfluidic Systems", and U.S. Patent Application Ser. No. 61/047,923, filed Apr. 25, 2008 and entitled "Flow Control in Microfluidic Systems", each of which is incorporated herein by reference in its entirety.

FIG. 1 shows a microfluidic device 10 according to one embodiment of the invention. As shown in this illustrative embodiment, device 10 comprises two attachable units: substrate 20, which includes a microfluidic system 22, and a fluidic connector 40, which can be used to connect two independent microfluidic channels of the substrate. Microfluidic system 22 of substrate 20 includes channel 24 having an inlet 26 and an outlet 28, as well as channel 34 having an inlet 36 and an outlet 38. As shown in the illustrative embodiment of FIG. 1A, channels 24 and 34 are not connected; that is, there is no fluid communication between the channels. As described in more detail below, non-connected channels may be advantageous in certain cases, such as for storing different reagents in each of the channels. For example, channel 24 may be used to store dry reagents and channel 34 may be used to store wet reagents. Having the channels be physically separated from one another can enhance long-term stability of the reagents stored in each of the channels, e.g., by keeping the reagent(s) stored in dry form protected from moisture that may be produced by reagent(s) stored in wet form. In some embodiments, physical separation of reagents may also prevent mixing between the reagents.

As shown, fluidic connector 40 includes a fluid path 42 having an inlet 46 and an outlet 44. Fluidic connector 40 can be connected to substrate 20, e.g., via the inlets and outlets. Upon connection, fluid path inlet 46 connects to outlet 38 of microfluidic channel 34 and fluid path outlet 44 connects to inlet 26 of microfluidic channel 24. This connection causes fluid communication between channels 24 and 34 via fluid path 42. The connections between the inlets and outlets of the article and the substrate may form fluid-tight seals to prevent leakage at the points of connection. Accordingly, as illustrated in FIG. 1B, if fluid flows in the direction of arrow 56, at least a portion of a fluid in channel 34 can flow into fluid path 42 and then into channel 24, optionally exiting at outlet 28.

Although FIG. 1A shows only two separate channels forming microfluidic system 22, in other embodiments, a microfluidic system may include more than two separate channels, and a fluidic connector can be used to connect three or more such channels of a substrate. In some such embodiments, a fluidic connector may have multiple fluid paths (which may be interconnected or independent) and/or multiple inlets and/or outlets that can connect to several different microfluidic channels of the substrate. Additionally, although FIG. 1 shows two separate channels 24 and 34 on the same substrate, article 40 can be used to connect channels on different substrates.

Figure 1B:
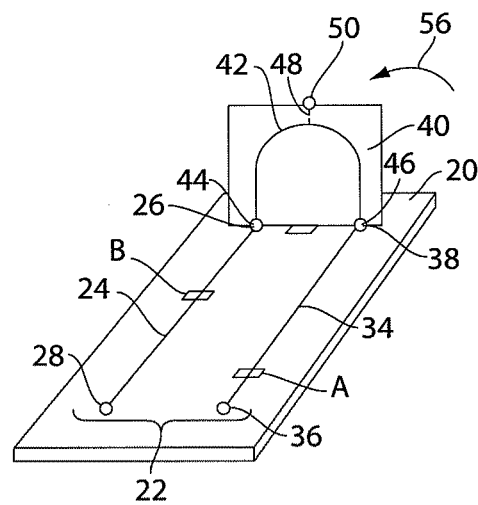

The microfluidic system formed by the connection of two independent channels of a substrate using a fluidic connector, as shown in FIG. 1B, is an example of an "open-loop" system. As used herein, an "open-loop" system does not allow recirculation of a fluid within the microfluidic system. In other words, a fluid portion starting out at a first position within the microfluidic system does not pass the first position again after it leaves that position. Instead, the fluid portion may exit the device at an outlet (unless, for example, the fluid portion gets processed or used up in the microfluidic system). For example, as illustrated in FIG. 1B, a fluid portion initially at position "A" and flowing in the direction of arrow 56 may flow into fluid path 42 and then into channel 24, optionally exiting at outlet 28; however, the design of the microfluidic system does not allow the fluid portion to re-enter channel 34 and to pass though position "A" again. Similarly, a fluid portion initially at position "B" and flowing in the direction of arrow 56 may exit outlet 28; this fluid portion cannot enter into channel 34 or 24 to allow the portion to pass though position "B" again.

In other embodiments, a fluidic connector can be used to form a "closed-loop" system. As used herein, a "closed-loop" system may allow recirculation of a fluid within the microfluidic system such that a fluid portion starting out at a first position within the microfluidic system can pass the first position again after it leaves that position. For example, if a second fluidic connector (e.g., one similar to fluidic connector 40) was used to connect inlet 36 and outlet 28 of substrate 20 of FIG. 1B, a closed-loop system would be formed. Alternatively, if microfluidic system 22 was designed so that inlet 36 and outlet 28 were joined such that channels 24 and 34 formed a single continuous channel, the connection of fluidic connector 40 to inlet 38 and outlet 26 would form a closed-loop system.

It should also be understood that a device described herein may include more than one fluidic connector. Multiple fluid connectors are useful for connecting multiple channels (or portions of channels) of one or more substrates. Connection of multiple channels using more than one fluid connector may be performed simultaneously or serially.

In certain embodiments, a fluidic connector may be used to connect two (or more) portions of a single microfluidic channel of a substrate. It should be understood that where at least first and second separate (independent) channels of a substrate are described herein, a fluidic connector may be used to connect similar embodiments but where at least a portion of the first channel is in fluid communication with at least a portion of the second channel (e.g., to form a single interconnected channel) prior to connection using the fluidic connector.

Optionally, and as described in more detail below, fluidic connector 40 may include at least one non-fluidic feature 52 complementary to a feature 54 of the substrate so as to form a non-fluidic connection between the fluidic connector and the substrate upon connection of the fluid path. This non-fluidic connection can help to stabilize the connection between the fluidic connector and substrate.

In some embodiments, fluidic connector 40 can be used to introduce a fluid (e.g., a sample such as blood, serum, plasma, tear fluid, saliva, urine, sperm, sputum, or any other fluid of interest) into the microfluidic system of substrate 20. This can allow the sample to bypass at least one channel of the substrate. For example, if a sample is first introduced into fluid path 42 and then fluidic connector 40 is connected to substrate 20 as shown in FIG. 1B, flow of the fluids in the direction of arrow 56 allows the sample contained in fluid path 42 to flow into channel 24, but not channel 34. Such a design may be useful for cases in which the sample to be delivered via fluid path 42 contaminates or otherwise undesirably affects one or more components within channel 34.

As described above, a fluid may be introduced into fluid path 42 via inlet 46 (or outlet 44, which may act as an inlet for purposes of fluid introduction). All or a portion of fluid path 42 may be filled with the fluid. Optionally, fluidic connector 40 may include a secondary flow path 48, which connects inlet 50 to flow path 42. This design can allow, for example, the introduction of a fluid into fluid flow path 42 via inlet 50 and secondary path 48 before or after the fluidic connector has been connected to the substrate (e.g., as shown in FIG. 1B). Alternatively, a fluid can be introduced into fluid path 42 via inlet 50 prior to connection of the fluidic connector and the substrate. In some embodiments, inlet 50 and secondary fluid path 48 can be blocked (e.g., with a plunger or using any other suitable method) after introducing fluid into fluid path 42 via inlet 50 and secondary fluid path 48. This blocking can decrease the number of channel intersections of the microfluidic system during operation of the device, and may be advantageous for reasons described below.

Some embodiments of the invention are in the form of a kit that may include, for example, a microfluidic system, a source for promoting fluid flow (e.g., a vacuum), and/or one, several, or all the reagents necessary to perform an analysis except for the sample to be tested. In some embodiments, the microfluidic system of the kit may have a configuration similar to one or more of those shown in the figures and/or as described herein.

The kit may include reagents and/or fluids that may be provided in any suitable form, for example, as liquid solutions or as dried powders. In some embodiments, a reagent is stored in the microfluidic system prior to first use, as described in more detail below. When the reagents are provided as a dry powder, the reagent may be reconstituted by the addition of a suitable solvent, which may also be provided. In embodiments where liquid forms of the reagent are provided, the liquid form may be concentrated or ready to use. The fluids may be provided as specific volumes (or may include instructions for forming solutions having a specific volume) to be flowed in the microfluidic system.

A kit described herein may further include a set of instructions for use of the kit. The instructions can define a component of instructional utility (e.g., directions, guides, warnings, labels, notes, FAQs ("frequently asked questions"), etc., and typically involve written instructions on or associated with the components and/or with the packaging of the components for use of the microfluidic system. Instructions can also include instructional communications in any form (e.g., oral, electronic, digital, optical, visual, etc.), provided in any manner such that a user will clearly recognize that the instructions are to be associated with the components of the kit.

Optionally, in some embodiments, microfluidic systems described herein contain stored reagents prior to first use of the device and/or prior to introduction of a sample into the device. In some cases, one or both of liquid and dry reagents may be stored on a single microfluidic substrate. Additionally or alternatively, the reagents may also be stored in separate vessels such that a reagent is not in fluid communication with the microfluidic system prior to first use. The use of stored reagents can simplify use of the microfluidic system by a user, since this minimizes the number of steps the user has to perform in order to operate the device. This simplicity can allows microfluidic systems described herein to be used by untrained users, such as those in point-of-care settings, and in particular, for devices designed to perform immunoassays. It has been demonstrated previously that the storage of the reagents in the form of liquid plugs separated by air gaps were stable for extended periods of time (see, for example, International Patent Publication No. WO2005/072858 (International Patent Application Serial No. PCT/US2005/003514), filed Jan. 26, 2005 and entitled "Fluid Delivery System and Method," which his incorporated herein by reference in its entirety). In other embodiments, however, microfluidic devices described herein do not contain stored reagents prior to first use of the device and/or prior to introduction of a sample into the device.

As used herein, "prior to first use of the device" means a time or times before the device is first used by an intended user after commercial sale. First use may include any step(s) requiring manipulation of the device by a user. For example, first use may involve one or more steps such as puncturing a sealed inlet to introduce a reagent into the device, connecting two or more channels to cause fluid communication between the channels, preparation of the device (e.g., loading of reagents into the device) before analysis of a sample, loading of a sample onto the device, preparation of a sample in a region of the device, performing a reaction with a sample, detection of a sample, etc. First use, in this context, does not include manufacture or other preparatory or quality control steps taken by the manufacturer of the device. Those of ordinary skill in the art are well aware of the meaning of first use in this context, and will be able easily to determine whether a device of the invention has or has not experienced first use. In one set of embodiments, devices of the invention are disposable after first use, and it is particularly evident when such devices are first used, because it is typically impractical to use the devices at all after first use.

Figure 2:
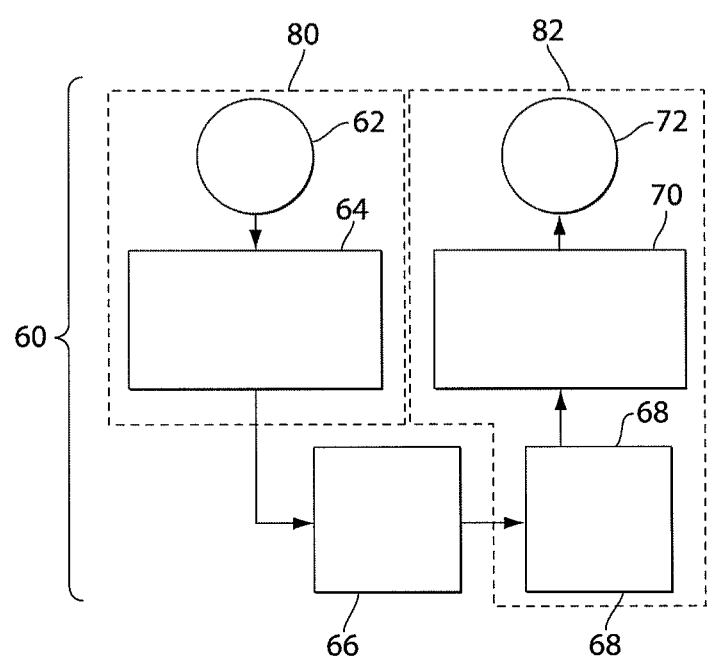
FIG. 2 is a block diagram of a microfluidic system that may contain stored reagents and can be used for performing an a chemical and/or biological reaction according to an embodiment of the invention.

FIG. 2 shows a block diagram 60 of a microfluidic device that may contain stored reagents and can be used for performing an a chemical and/or biological reaction (e.g., an immunoassay). The microfluidic device includes a reagent inlet 62 in fluid communication with a reagent storage area 64, which may include, for example, one or more channels and/or reservoirs. The device may also include a sample loading area 66, such as a fluidic connector that can connect reagent storage area 64 to reaction area 68. The reaction area, which may include one or more areas for detecting a component in a sample (e.g., detection zones), may be in fluid communication with waste area 70 and coupled to outlet 72. In some embodiments, reaction area 68 is an immunoassay area. Waste areas may be in the form of liquid containment regions, which are described in more detail below.

In the exemplary embodiment shown in FIG. 2, section 80 comprises the reagent inlet and reagent storage area, and section 82 comprises the reaction area, waste area, and outlet. Reagents may be stored in one or both of sections 80 and 82. For example, in one particular embodiment, a reagent is stored in the form of a fluid (e.g., a liquid or a gas) in reagent storage area 64 of section 80, and a reagent in the form of a dry film is stored in reaction area 68 of section 82.

In some embodiments, sections 80 and 82 are in fluid communication with one another (e.g., via sample loading area 66) prior to introduction of a sample into the device. For example, if sample loading area 66 included fluidic connector 40 of FIG. 1, the fluidic connector can be connected to the substrate to cause fluid communication between sections 80 and 82. Subsequently, a sample may be introduced into the device via inlet 50 and secondary fluid path 48.

In other embodiments, sections 80 and 82 are not in fluid communication with one another prior to introduction of a sample into the device. For example, if sample loading area 66 included fluidic connector 40 of FIG. 1 which did not have inlet 50 or secondary fluid path 48, the fluidic connector may first be filled with a sample and then connected to the substrate to cause fluid communication between sections 80 and 82. In this example, the sample is introduced into the channels of the substrate at the time when (or shortly after) fluid communication is formed between sections 80 and 82. In such instances, sections 80 and 82 are not in fluid communication with one another prior to first use of the device, wherein at first use, the sections are brought into fluid communication with one another.

It should be understood that while the microfluidic system presented by block diagram 60 includes only two sections 80 and 82, a microfluidic device may include additional sections in other embodiments. Additionally, the sequence of fluid flow between reagent storage area 64, sample loading area 66, and reaction area 68 may be different in some devices. For example, fluid flow may be directed from a reagent storage area to reaction area followed by fluid flow from a sample loading area to the reaction area. Other arrangements are also possible.

As described herein, one or more reagents that may be used in a chemical and/or biological reaction may be stored in the device prior to first use and/or prior to introduction of a sample into the device. Such reagents may be stored in fluid, gel, and/or dry form, and the method of storage may depend on the particular application. Reagents can be stored, for example, as a liquid, a gas, a gel, a plurality of particles, or a film. The reagents may be positioned in any suitable portion of a device, including, but not limited to, in a channel, reservoir, on a surface, and in or on a membrane, which may be part of a reagent storage area. A reagent may be associated with a microfluidic system (or components of a system) in any suitable manner. For example, reagents may be crosslinked (e.g., covalently or ionically), absorbed, or adsorbed (physisorbed) onto a surface within the microfluidic system. In some cases, a liquid is contained within a channel or reservoir of a device.

In some embodiments, dry reagents are stored in one section of a microfluidic device and wet reagents are stored in a second section of a microfluidic device. Alternatively, two separate sections of a device may both contain dry reagents and/or wet reagents. The first and second sections may be in fluid communication with one another prior to first use, and/or prior to introduction of a sample into the device, in some instances. In other cases, the sections are not in fluid communication with one another prior to first use and/or prior to introduction of a sample into the device. During first use, a stored reagent may pass from one section to another section of the device. For instance, a reagent stored in the form of a fluid can pass from a first section to a second section of the device after the first and second sections are connected via a fluid path (e.g., a fluidic connector). In other cases, a reagent stored as a dried substance is hydrated with a fluid, and then passes from the first section to the second section upon connection of the sections. In yet other cases, a reagent stored as a dried substance is hydrated with fluid, but does not pass from one section to another section upon connection of the sections.

As mentioned, in some cases a liquid is stored within a reservoir (e.g., a microfluidic channel) of a device. The device may include, for example, a reservoir associated with a device (e.g., formed in or on a substrate of the device), the reservoir containing a first liquid reagent stored therein prior to use of the device. Optionally, the reservoir may be, or may be in fluid communication with, a first microfluidic channel. A reaction area may be in fluid communication with the first microfluidic channel during use of the device. The device may also include an absorbent material associated with (e.g., contained in) a liquid containment region positioned downstream of the reaction area and in fluid communication with the reaction area during use of the device. In some embodiments, the device further comprises a second microfluidic channel containing a second reagent disposed therein prior to use of the device. In one embodiment, the first and second microfluidic channels are in fluid communication with each other prior to use of the device. In other embodiments, the first and second microfluidic channels are not in fluid communication with one another prior to use of the device, but during use of the device, the first and second microfluidic channels are brought into fluid communication with one another, e.g., via a fluid connector. In some such embodiments, the absorbent material and stored liquid may be kept in separate channels prior to use of the device to enhance long-term storage of the device. Optionally, a second reagent, such as a dried reagent, may be disposed in the reaction area. Upon causing fluid communication between the first and second channels, the stored liquid may interact with the reagent at the reaction area. Methods of storing reagents and conducting interactions between stored reagents are described in further detail below.

As described herein, in some embodiments, fluids are stored in a microfluidic channel prior to use. Storing a fluid in a microfluidic channel, e.g., a reservoir having an aspect ratio (length to average cross sectional dimension) of at least 2:1, or, in other embodiments, at least 3:1, 5:1, or 10:1, may have certain advantages over storing a fluid in a reservoir that is not in the form of a channel. For instance, because of the large aspect ratio of a microfluidic channel, multiple fluids and different types of fluids can be stored in the channel simultaneously. This configuration can allow storage of alternating fluids such as two plugs of an aqueous liquid separated by an immiscible fluid (e.g., a hydrophobic liquid or a gas), which may be useful for physically separating stored fluids in a device and/or for positioning particular fluids in a sequence for carrying out specific tasks. For example, as described in more detail below, a first liquid plug may include a reagent for amplifying a signal and a second liquid plug may include a washing reagent; the first and second plugs may be flowed over a reaction area to allow sequential interaction of the liquids with one or more species at the reaction area. Fluids may be stored in a microfluidic channel (e.g., as plugs) in series and/or in parallel.

In some instances, a microfluidic channel used as a storage reservoir can allow a device to have a relatively smaller height (and/or width) compared to a storage reservoir that is not in the form of a microfluidic channel. A small height and/or width may have certain advantages, in some embodiments, such as reducing the amount of materials required to fabricate the device, increasing the compactness of the device (which may be useful for portability, storage, and/or for stacking a plurality of devices, for example), and/or facilitating integration of a detector with the device (e.g., as a signal or light source may have less material to penetrate).

Storing fluids in one or more microfluidic channels can also be advantageous for performing on-chip mixing of reagents (e.g., mixing a substrate with an enzyme, a reagent with its corresponding catalyst, or individual components of a reagent kit) before their use in an analysis or test. In addition, a fluid stored in a microchannel can be used to dilute a sample positioned in another microfluidic channel, e.g., by flowing these fluids through a intersection. The dilution ratio can be conveniently controlled by the hydrodynamic resistance of each microfluidic channel.

The use of microfluidic channels for storage of reagents can also facilitate automation of various tasks for performing an analysis such as automation of mixing, dilution, and incubation. For example, storing fluids in channels may eliminate or reduce the number of processes involving introducing fluids into a channel and/or combining particular fluids to be used in a reaction.

In addition, storing fluids in one or more microfluidic channels can allow the device to withstand handling, manipulation, and/or mechanical shock during shipment and/or use of the device. For example, when multiple aqueous reagents are stored in the form of a sequence of plugs separated by plugs of an immiscible fluid, the device may be designed such that the channel containing the stored sequence of plugs has a small cross-sectional dimension. For instance, in certain embodiments, one or more cross-sectional dimensions of a channel containing a stored sequence of plugs may be less than 700 microns, less than 500 microns, less than 400 microns, less than 300 microns, 250 microns, less than 200 microns, less than 150 microns, less than 100 microns, less than 75 microns, less than 50 microns, or less than 30 microns. In one embodiment, a channel used for storing fluids has a first cross-sectional dimension at a first position and a second cross-sectional dimension at a second position. For example, channel 112 of storage area 110 of FIG. 3 may have a larger cross-sectional dimension near inlet 116 or outlet 118, and a smaller cross-sectional dimension away from the inlet and outlet. In some cases, one or more cross-sectional dimensions of a channel containing a stored fluid (e.g., a sequence of plugs) is smaller than a cross-sectional dimension of a channel of the device that is not used to store fluids (e.g., in certain embodiments, a channel associated with a reaction area, a sample introduction area, a fluid connector, a waste area, an inlet and/or an outlet). (Of course, in other embodiments, a fluid storage channel having a cross-sectional dimension larger than that of a non-fluid storage channel is also possible.) If the device is dropped during shipment, storage, and/or use, a storage channel having a small cross-sectional dimension may reduce the tendency of a plug of liquid to break up into multiple, smaller plugs, each separated by a small air bubble. In such an instance, there may be no loss of liquid from the device, but the specific sequence of immiscible fluids may change, which can impact performance of the device. Accordingly, using microfluidic channels having certain dimensions for storing fluids can improve the stability of the sequence of fluids being stored, as well as the stability of the test being performed during use.

It should be understood that in some embodiments, microfluidic devices described herein may include reservoirs that are not in the form of microfluidic channels, the reservoirs having stored fluids contained therein.

FIGS. 3A-3D show an example of a microfluidic device including a fluidic connector and containing stored reagents that can be used in a chemical and/or biological reaction. Device 100 includes a first section 106 including reagent storage area 110, which is in the form of a channel 112 and includes an inlet 116 and an outlet 118. Different reagents may be stored in channel 112 depending on the particular application. For example, if the device were used to perform an immunoassay, the channel may have stored therein, in series, a rinse fluid 120, an antibody fluid 122, a rinse fluid 124, a labeled-antibody fluid 126, and a rinse fluid 128. Additional reagents and rinse fluids may also present as needed. These reagents may be in the form of plugs (e.g., liquid plugs) that are separated from one another by immiscible fluid plugs 130 (e.g., a separation fluid such as a gas (e.g., air, nitrogen, or argon) or an oil (e.g., a fluorocarbon or hydrocarbon)). In FIG. 3A, inlet 116 and outlet 118 are sealed so as to prevent evaporation and contamination of the stored reagents.

Device 100 also includes a second section 150 having an inlet 154, an outlet 156, a channel 158, reaction area 160, and a waste area 174. The waste area may be in the form of a liquid containment region, which is described in more detail below. The reaction area may include several detection zones 162, 164, 166, and 168. The detection zones may have any suitable configuration and/or arrangement. In one embodiment, each of the detection zones is in the form of a meandering (serpentine) channel, as described in more detail below and in International Patent Publication No. WO2006/113727 (International Patent Application Serial No. PCT/US06/14583), filed Apr. 19, 2006 and entitled "Fluidic Structures Including Meandering and Wide Channels," which is incorporated herein by reference in its entirety. The detection zones may be arranged to detect, for example, different components of sample, or may be used as positive and/or negative controls. In some cases, one or more of the detection zones contains a reagent stored therein. In one particular embodiment, a device used for performing an immunoassay includes a series of stored dry reagents. The reagents may be physisorbed onto a surface of the meandering channel. For example, detection zone 162 may include a negative control (e.g., a detergent known to prevent adhesion of proteins), detection zones 164 and 166 may include different concentrations of antibodies that may bind to a component in a sample (or two different antibodies that can bind to different components in the sample), and detection zone 168 may include a positive control (e.g., the same antigen expected to be determined from a sample). The positive control may be used as a qualitative control; for example, if a signal reaches a certain threshold, the test can be considered valid. Additionally and/or alternatively, the positive control can also be as a quantitative tool; for example, the intensity of the signal can be can be part of an on-chip calibration process.

As shown in the embodiment illustrated in FIG. 3A, each of the areas within section 150 are in fluid communication with one another, but none are in fluid communication with any of the components of section 106. In certain embodiments, section 150 containing stored dry reagents and section 106 containing stored wet reagents are configured to not be in fluid communication with one another prior to first use because this configuration can promote long-term storage of each of the reagents in their respective sections, as described further below.

As shown in FIG. 3B, sections 106 and 150 can be connected using fluidic connector 178, causing sections 106 and 150 to be in fluid communication with one another. If outlet 118 and inlet 154 are covered with a seal (e.g., a biocompatible tape, membrane, or a septum) in FIG. 3A, this connection can cause the sealings over the outlet and inlet to be pierced, broken, or removed.

Fluidic connector 178 may be used for sample loading and may include sample 180 contained therein. As described herein, sample 180 may be introduced into fluidic connector 178 by an suitable method, and, in some cases, is introduced into the fluidic connector prior to there being fluid communication between sections 106 and 150.

As shown in the embodiment illustrated in FIG. 3C, fluids in reagent storage area 110 and sample 180 may flow from section 106 towards section 150. Fluid flow may take place, for example, by applying a positive pressure to inlet 116 (e.g., using a plunger, gravity, or a pump) or by applying a vacuum source to outlet 156. In some such embodiments, a source of positive pressure and/or vacuum may be connected to one or more inlet(s) and/or outlet(s), respectively.

Sample 180 first flows into reaction area 160 (FIG. 3C), and then into waste area 174 (FIG. 3D). The passing of the sample through the detection zones allows interaction (e.g., binding) between one or more components of the sample (e.g., an antigen) and one or more components in the reaction area (e.g., an antibody). As described herein, the component(s) of the reaction area may be in the form of dried reagents stored in the reaction area prior to first use. In some such cases, the reaction area is not associated with an absorbent material. This interaction may form a product such as a binding pair complex. In some cases, this interaction alone causes a signal to be determined (e.g., measured) by a detector coupled to the microfluidic system. In other cases, in order for an accurate signal to be determined by the detector, the product is treated by one or more reagents from reagent storage area 110. For example, a reagent stored in reagent storage area 110 may be a labeled-antibody that interacts with an antigen of the sample. This interaction can allow the product to be labeled or the signal from the product to be amplified.

In one particular embodiment involving an immunoassay, the stored reagents in the storage area include an enzyme amplification solution and a precipitating dye (e.g., diaminobenzidine, DAB). The one or more reagents from reagent storage area 110 is allowed to pass through each of the detection zones. These reagents may interact further with a binding pair complex, e.g., to amplify the signal and/or to label the complex, as depicted in detection zones 164 and 168 of FIG. 3D.

By maintaining an immiscible fluid (a separation fluid) between each of the reagents in the reagent storage area, the stored fluids can be delivered in sequence from the reagent storage area while avoiding contact between any of the stored fluids. Any immiscible fluid that separates the stored reagents may be applied to the reaction area without altering the conditions of the reaction area. For instance, if antibody-antigen binding has occurred at one of the detection zones of the reaction area, air can be applied to the site with minimal or no effect on any binding that has occurred.

Different types of separation fluids can be used to separate fluids in a device. Separation fluids can be in the form of a liquid that is hydrophilic (e.g., aqueous) or hydrophobic (i.e., an oil), or in the form of a gas (e.g., air, nitrogen, oxygen, argon, mixtures thereof, etc.). The type of separation fluid may be chosen, at least in part, depending on the type of fluids that are to be separated (e.g., aqueous or oil-based), the type of process to be carried out in the device, and/or the length of time the fluids are separated. For instance, in some embodiments, if fluids that require separation are stored in a device for greater than 24 hours, for example, it may be desirable in some embodiments to use a separation fluid that is completely immiscible with a liquid in the device (e.g., a stored reagent). In certain embodiments, if fluids are not stored in the device but are introduced into the device during use, a separation fluid that is slightly miscible with a stored reagent may be used. In some cases, a separation fluid comprises a fluorocarbon. Sometimes, a hydrophobic fluid, which is immiscible with an aqueous reagent, is slightly water soluble. For example, oils such as PDMS and poly(trifluoropropylmethysiloxane) are slightly water soluble. Those of ordinary skill in the art can determine appropriate combinations of liquids and separation fluids based on their solubility parameters, by simple experimentation, e.g., mixing the fluids and observing the degree of separation, and the like.

A separation fluid may have any suitable volume and/or length in a microfluidic channel for separating fluids. For instance, in one embodiment a separation fluid may have a volume of at least 10 pL, or in other embodiments, at least 0.1 nL, at least 1 nL, at least 10 nL, at least 0.1 µL, at least 1 µL, at least 10 µL, or at least 100 µL.

As described herein, storing reagents in a microfluidic system can allow the reagents to be dispensed in a particular order for a downstream process (e.g., amplifying a signal in a reaction area). In cases where a particular time of exposure to a reagent is desired, the amount of each fluid in the microfluidic system may be proportional to the amount of time the reagent is exposed to a downstream reaction area. For example, if the desired exposure time for a first reagent is twice the desired exposure time for a second reagent, the volume of the first reagent in a channel may be twice the volume of the second reagent in the channel. If a constant pressure differential is applied in flowing the reagents from the channel to the reaction area, and if the viscosity of the fluids is the same or similar, the exposure time of each fluid at a specific point, such as a reaction area, may be proportional to the relative volume of the fluid. Factors such as channel geometry, pressure or viscosity can also be altered to change flow rates of specific fluids from the channel.

Additionally, this strategy of storing reagents in sequence, especially amplification reagents, can be adapted to a wide range of chemistries. For example, various amplification chemistries that produce optical signals (e.g., absorbance, fluorescence, glow or flash chemiluminescence, electro-chemiluminescence), electrical signals (e.g., resistance or conductivity of metal structures created by an electroless process) or magnetic signals (e.g., magnetic beads) can be used to allow detection of a signal by a detector.

The use of gaseous (e.g., air) plugs to separate reagents requires the overall microfluidic device to be compatible with many air bubbles. Although air bubbles may be stabilized and/or controlled within microfluidic devices using a variety of methods, one particular method used in certain embodiments described herein includes limiting the number of channel intersections in the system. Accordingly, microfluidic devices described herein may be designed to have few (e.g., less than 5, 4, 3, or 2), one, or no channel intersections. As used herein, a channel intersection includes at least three channels (or portions of one or more channels) intersecting at a single point (e.g., forming a "Y"). For example, device 100 of FIG. 3 does not have any channel intersections and device 200 of FIG. 4 has only one channel intersection 219. Devices that do not have any channel intersections may be useful, for example, for performing reactions that do not require mixing of reagents (e.g., stored reagents).

FIGS. 4A-4D show another example of a microfluidic device including a fluidic connector and containing stored reagents that can be used in a chemical and/or biological reaction. As shown in these illustrative embodiments, device 200 includes a first section 202 comprising reagent storage area 204. The reagent storage area has two parts: upper portion 205 and lower portion 206. The upper portion includes channel 208 having inlet 216 connected thereto and channel 209 having inlet 217 connected thereto. Channels 208 and 209 are separated in the upper portion and meet at intersection 219, which is connected to channel 212 of the lower portion. Channel 212 is connected to an outlet 218. Device 200 having two inlets 216 and 217, each connected to a different channel, may be useful, for example, for performing reactions in which two reagents need to be stored separately on the device, but which require mixing during use or immediately before use.

In one particular embodiment, device 200 is used to perform an immunoassay for human IgG, which uses sliver enhancement for signal amplification. A solution of silver salts is stored in channel 208 and a solution of hydroquinone is stored in channel 209. Because these two components, which can produce signal amplification upon mixing, are located in separate channels, they cannot mix with each other until the flow drives both solutions towards intersection 219.

Reagents that do not have to be mixed with one another can be stored in lower portion 206 of the reagent storage area. These reagents can include, for example, rinse fluids, antibody fluids, and other fluids as needed. The reagents may be in the form of plugs that are separated from one another by immiscible fluid plugs 230 (e.g., a separation fluid such as a gas (e.g., air) or an oil). In FIG. 4A, inlets 216 and 217, and outlet 218 are sealed so as to prevent evaporation and contamination of the stored reagents.

Device 200 also includes a second section 250 having an inlet 254, an outlet 256, a channel 258, a reaction area 260, and a waste area 274. Examples of waste areas, which may be in the form of liquid containment regions, are described in more detail below. The reaction area may include several detection zones 262, 264, 266, and 268. Optionally, one or more detection zones may be in the form of a meandering channel region, as described herein. The detection zones may be arranged to detect, for example, different components of sample, or used as positive and/or negative controls. In some cases, one or more of the detection zones contains a reagent stored therein. In one embodiment, a device used for performing an immunoassay includes a series of stored dry reagents. The reagents may be physisorbed onto a surface of a meandering channel of a detection zone. In some such embodiments and/or in other embodiments, the reaction area is not associated with an absorbent material used for storing the reagents; that is, an absorbent material is not positioned in the reaction area.

In one particular embodiment, wherein device 200 is used for performing an immunoassay for human IgG and uses sliver enhancement for signal amplification, one or more surfaces of the meandering channels of the reaction area is modified by biomolecules such as BSA (bovine serum albumin) or Tween, a negative control (e.g., a detergent known to prevent adhesion of proteins), different concentrations of antibodies (e.g., anti-human IgG) that may bind to a component in a sample, and human IgG, a positive control (e.g., the same antigen expected to be determined from a sample). These reagents are stored in section 250 prior to use by sealing inlet 254 and outlet 256.

As shown in FIG. 4B, sections 202 and 250 can be connected using fluidic connector 278, causing sections 202 and 250 to be in fluid communication with one another. Fluidic connector 278 may be used for sample loading and may include sample 280 (e.g., blood) contained therein. As described herein, sample 280 may be introduced into fluidic connector 278 by an suitable method, and, in some cases, is introduced into the fluidic connector prior to there being fluid communication between sections 202 and 250.

As shown in the embodiment illustrated in FIG. 4C, fluids in reagent storage area 204 and sample 280 may flow towards section 250. Fluid flow may take place, for example, by applying a positive pressure to inlets 216 and 217 (e.g., using a plunger, gravity, or a pump) or by applying a vacuum source to outlet 256. Sample 280 first flows into reaction area 260 (FIG. 4C), and then into waste area 274 (FIG. 4D). The passing of the sample through the detection zones allows interaction (e.g., binding) between one or more components of the sample and one or more components stored in the reaction area. This interactions may form, for example, a product such as a binding pair complex. Subsequent flow of fluids from the reagent storage area over the detection zones can cause labeling of the product and/or signal amplification.

In one particular embodiment, device 200 is used for performing an immunoassay for human IgG and uses sliver enhancement for signal amplification. After delivery of a sample containing human IgG from the fluidic connector to the reaction area, binding between the human IgG and a stored dry reagent, anti-human IgG, can take place. This binding can form a binding pair complex in a detection zone. Stored reagents from lower portion 206 of reagent storage area 204 can then flow over this binding pair complex. One of the stored reagents may include a solution of metal colloid (e.g., a gold conjugated antibody) that specifically binds to the antigen to be detected (e.g., human IgG). This metal colloid can provide a catalytic surface for the deposition of an opaque material, such as a layer of metal (e.g., silver), on a surface of the detection zone. The layer of metal can be formed by using a two component system as described above: a metal precursor (e.g., a solution of silver salts), which can be stored in channel 208, and a reducing agent (e.g., hydroquinone), which can be stored in channel 209. As a positive or negative pressure differential is applied to the system, the silver salt and hydroquinone solutions eventually merge at intersection 219, where they mix slowly (e.g., due to diffusion) along channel 212, and then flow over the reaction area. Therefore, if antibody-antigen binding occurs in the reaction area, the flowing of the metal precursor solution through the area can result in the formation of an opaque layer, such as a silver layer, due to the presence of the catalytic metal colloid associated with the antibody-antigen complex. The opaque layer may include a substance that interferes with the transmittance of light at one or more wavelengths. Any opaque layer that is formed in the microfluidic channel can be detected optically, for example, by measuring a reduction in light transmittance through a portion of the reaction area (e.g., a meandering channel) compared to a portion of an area that does not include the antibody or antigen. Alternatively, a signal can be obtained by measuring the variation of light transmittance as a function of time, as the film is being formed in a detection zone. The opaque layer may provide an increase in assay sensitivity when compared to techniques that do not form an opaque layer.

FIGS. 5A-5F show images of a device used to perform a human IgG immunoassay according to one embodiment of the invention, and is described in more detail in the Examples section.

Although immunoassays are primarily described, it should be understood that devices described herein may be used for any suitable chemical and/or biological reaction, and may include, for example, other solid-phase assays that involve affinity reaction between proteins or other biomolecules (e.g., DNA, RNA, carbohydrates), or non-naturally occurring molecules.

Moreover, although many embodiments described herein include the use of a fluidic connector to connect two channels or two portions of a channel, embodiments herein also include articles and methods for introducing a sample into a microfluidic system without using a fluidic connector. For example, in some embodiments, an open-ended fluidic device (i.e., a device where only one end is connected to a microfluidic system) may be used to introduce a sample into the microfluidic system.

Figure 6:
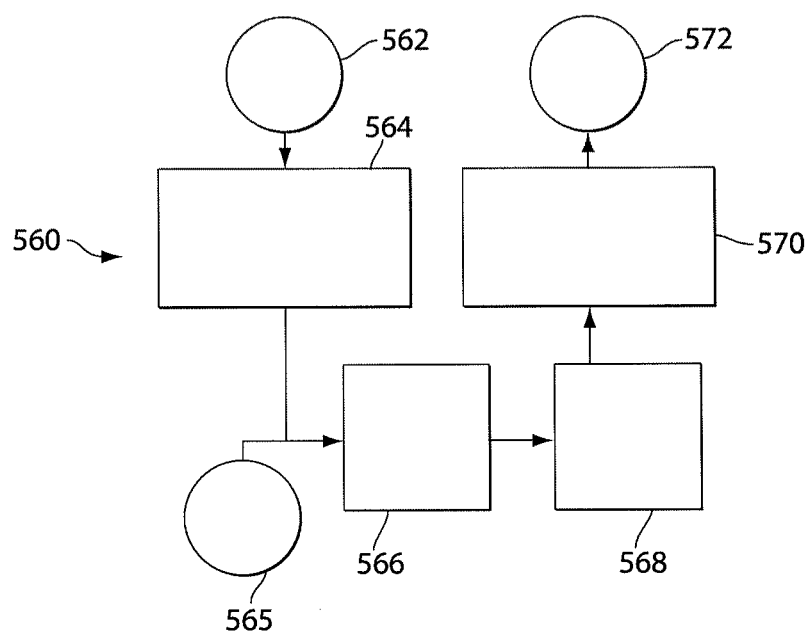
FIG. 6 is a block diagram of a microfluidic system according to an embodiment of the invention.

FIG. 6 shows a block diagram 560 of a microfluidic device that is compatible with using an open-ended device for sample introduction. The microfluidic device may contain stored reagents and can be used for performing an a chemical and/or biological reaction (e.g., an immunoassay). The microfluidic device includes a reagent inlet 562 in fluid communication with a reagent storage area 564, which may include, for example, one or more channels and/or reservoirs. The device may also include a sample inlet 565, sample loading area 566, and reaction area 568. The reaction area, which may include one or more areas for detecting a component in a sample, may be in fluid communication with waste area 570, and may be coupled to outlet 572. In some embodiments, reaction area 568 is an immunoassay area. The waste area may be in the form of a liquid containment region, which is described in more detail below.

Figure 7A:
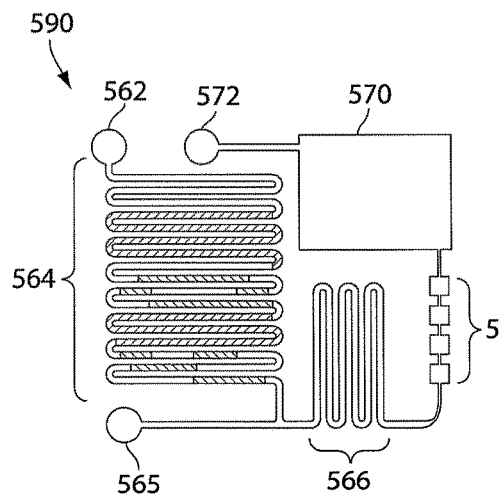
FIGS. 7A-7D are schematic diagrams of a microfluidic device that can be used with an open-ended fluidic device to perform a chemical and/or biological reaction according to an embodiment of the invention.
Figure 7B:
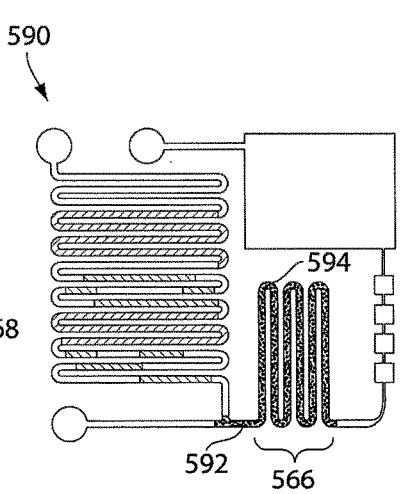
Figure 7C:
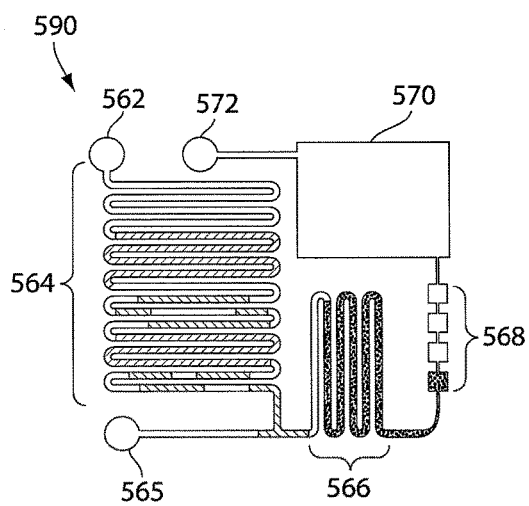
Figure 7D:
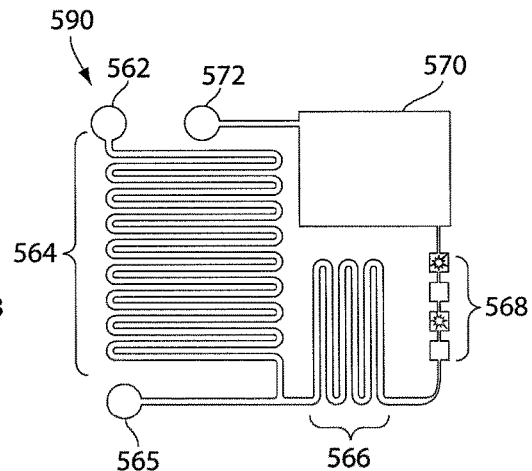

FIGS. 7A-7D show an example of a microfluidic system having the features described in FIG. 6. Microfluidic system 590 is compatible with an open-ended fluidic device for introducing a sample into the system. In FIG. 7A, fluid reagents are stored in reagent storage area 564 and dry reagents are stored in reaction area 568. Inlets 562 and 565, and outlet 572 are sealed prior to use. As shown in the embodiment illustrated in FIG. 7B, a seal over sample inlet 565 can be pierced, removed, or broken to allow a sample 592 to be introduced into sample inlet 565, which can flow into sample loading area 566, which may include an empty meandering channel 594. Flow of the sample may take place initially by capillary forces. Optionally, a seal may be placed over sample inlet 565 and a vacuum can be applied to outlet 572 to cause fluid flow towards the outlet (FIG. 7C). The sample flows into reaction area 568, followed by the stored fluid reagents from reagent storage area 564. As shown in FIG. 7D, after all of the reagents have passed through the reaction area, they may be contained in waste area 570 (or, optionally, may exit out of the device via the outlet).

As described herein, fluids (e.g., samples) can be introduced into a microfluidic device using a variety of devices such as an open-ended fluidic device and/or a fluidic connector. Although several configurations of such devices are shown in FIGS. 8-13, it should be understood that the invention is not limited to these configurations and that other configurations and/or arrangements are possible. Additionally, although descriptions herein involving sample introduction components (e.g., open-ended fluidic devices and fluidic connectors) primarily describe introduction of samples to microfluidic substrates, such components can be used to introduce any suitable substance such as reagents (e.g., buffers, amplification reagents, a component of a two-part system), gases, and particles.

For devices used in point-of-care settings, the sample introduction components may be designed to protect the user from occupational hazards. Additionally, the complexity of the sample-handling step may be minimized to allow the use of the device outside medical laboratories. These factors may be considered when choosing a particular design for a sample introduction component.

Sample introduction components such as open-ended fluidic devices and fluidic connectors may include any suitable article having a fluid path disposed therein. The sample introduction component may have a consistent or variable inner diameter and may have a length-to-internal diameter ratio of, for example, greater than 10 to 1, greater than 50 to 1, or greater than 100 to 1. Depending upon the application, sample introduction components of any diameter may be used, and in many applications it may have an inner diameter of, for example, less than 1 cm, less than 5 mm, less than 1 mm, less than 500 microns, less than 200 microns, less than 100 microns, or less than 50 microns. A sample introduction component with a greater length-to-internal diameter ratio may be useful in visually indicating the amount of each fluid contained in the component. For instance, a linear measurement of a fluid plug in a fluidic device or fluidic connector of known inner diameter may give an accurate indication of the volume or the relative volume of the fluid. In some embodiments, the sample introduction component comprises a tube. Tubes are readily available in different diameters, lengths and materials. Tubes may be flexible and may be translucent or transparent. Fluid plugs in a tube may be measured linearly as an indication of the volume of the plug.

The sample introduction component, if a tube or another shape, may include two or more branches or sections that may be in fluid communication with each other and with the remaining interior of the component. In some embodiments, a tube may have two, three, four or more branches that may be interconnected. The branches and branch junctions may or may not include valves. Valves may be used to temporarily segregate one or more branches, and any liquid contained therein, from the remainder of the tube.

In some embodiments, a sample introduction component such as an open-ended fluidic device or a fluidic connector includes a volume control element. The volume control element can allow a fluid to fill a portion, but not all, of a fluid path of a sample introduction component. The volume control element can be used to meter a particular volume of fluid for introduction into a microfluidic system. In one embodiment, a volume control element is a frit, which can be placed inside a fluid path of a sample introduction component to stop further fluid from being introduced inside the fluid path after the fluid reaches a particular volume. The volume of fluid (e.g., sample) in the sample introduction component can be defined by the volume of the fluid path between the entry point (e.g., an inlet) for fluid introduction and the frit; the remaining volume may be occupied by air.

In another embodiment, a volume control element includes one or more metering marks that indicate up to which point(s) a fluid should be introduced into the fluid path. The volume of fluid in the fluid path may be controlled by the user.

In yet another embodiment, a volume control element includes a change in diameter (e.g., widening) of a fluid path within the sample introduction component. For instance, an open-ended fluidic device or a fluidic connector may include a first end (e.g., an opening), a first portion of a fluid path having a first diameter, a second portion of the fluid path having a second diameter, followed by a second end (e.g., an opening). The second diameter may be greater than the first diameter. The first diameter may be favorable for causing fluid to flow into the fluid path via capillary forces, while the second diameter may be less favorable (or unsuitable) for capillary action. Accordingly, a fluid may enter the first portion of the fluid path via the first end and the fluid may stop entering the fluid path when it reaches the second portion of the fluid path. In this embodiment, the volume of fluid (e.g., sample) in the sample introduction component can be defined by the volume of the first portion of the fluid path; the remaining volume (e.g., the second portion of the fluid path) may be occupied by air. Those of ordinary skill in the art know how to determine diameters of fluid paths that are favorable or less favorable for capillary action.

In yet another embodiment, a volume control element includes a patterned surface within a fluid path of the sample introduction component. For instance, a sample introduction component may include a first end (e.g., an opening), a first portion of a fluid path having a first, hydrophilic surface, a second portion of the fluid path having a second, hydrophobic surface, followed by a second end (e.g., an opening). The first, hydrophilic surface can cause a hydrophilic fluid (e.g., an aqueous fluid) to flow into the fluid path via capillary forces, while the second, hydrophobic surface is less favorable for capillary action. Accordingly, a fluid may enter the first portion of the fluid path via the first end and the fluid may stop entering the fluid path when it reaches the second portion of the fluid path. In this embodiment, the volume of fluid (e.g., sample) in the sample introduction component can be defined by the volume of the first portion of the fluid path; the remaining volume (e.g., the second portion of the fluid path) may be occupied by air. In one particular embodiment, a hydrophilic portion of the fluid path is defined by the presence of an anti-coagulant (e.g., heparin, a chelator (e.g., ethylenediamine tetraacetic acid, EDTA) or citrate), and a hydrophobic portion of the fluid path is defined by the absence of an anti-coagulant (or the presence of one or more hydrophobic molecules). Methods and materials for patterning surfaces of fluid paths are known by those of ordinary skill in the art.

In some embodiments, a sample introduction component such as an open-ended fluidic device or fluidic connector can include a combination of volume control elements such as the ones described above. A sample introduction component including one or more volume control elements can be filled using any suitable method such as by capillary forces, application of a vacuum, application of a positive pressure, and by use of valves.

As described in more detail below, sample introduction components can be connected to a substrate using a variety of methods. For example, a sample introduction component and/or substrate may include one or more of the following: pressure-fittings, friction-fittings, threaded connectors such as screw fittings, snap fittings, adhesive fittings, clips, magnetic connectors, or other suitable coupling mechanisms.

FIG. 8A shows an example of an open-ended capillary tube 700 (e.g., open-ended fluidic device) that can be used for introducing a sample into an inlet of a device (e.g., sample inlet 565 of FIG. 7A). Tube 700 may have an open end 704 (e.g., for inserting into an inlet of a device); end 702 may either be opened or closed. As shown in FIG. 8B, a capillary tube 710 can also be used as a fluidic connector to connect two channels (or portions of a channel) of a microfluidic system, e.g., as described in connection with FIG. 3.

Tube 710 can include opened ends 712 and 714. The use of a capillary bent to form a "U"-shape is one of many possible devices that can be used to connect two channels (or portions of a channel).

The devices of FIGS. 8A and 8B can be made of any suitable material (e.g., a polymer or ceramic) and may be rigid or flexible. Non-limiting examples of such materials include glass, quartz, silicon, a metal (e.g., stainless steel), PTFE (Teflon), polyethylene, polycarbonate, poly(dimethylsiloxane) (PDMS), PMMA, polystyrene, a cyclo-olefin copolymer (COC) and cyclo-olefin polymer (COP). In certain embodiments where the tubes are formed of a flexible material, the tube may be placed in a holder of a sufficiently rigid material to maintain the tube in its final shape. For example, as shown in the embodiment illustrated in FIG. 8C, tube 720 may be positioned in groove 732 of holder 730 to maintain the shape of the tube. Optionally, a cover 734 may be used to cover the holder and may be attached to the holder, for example, by sealing, gluing, bonding, using adhesives, or by mechanical attachment (e.g., clipping into the holder). In other embodiments, instead of positioning the tube in a groove, the holder may include raised features (e.g., clips) for securing the tube. Ends 722 and 724 may be exposed to allow connection to one or more channels of a microfluidic system (FIG. 8D).

In another embodiment, an open-ended fluidic device (e.g., a capillary tube) or a portion of a fluidic connector can be made of a radiation-sensitive material such as a flexible plastic that hardens upon exposure to heat or UV light. After folding or bending the device in the desired shape (e.g., a "U"-shape), exposure to the appropriate radiations can cause the capillary to maintain its new shape.

In yet another embodiment, instead of bending straight capillaries to form a U-shape design, the open-ended fluidic device or fluidic connector can be manufactured directly in its final form. One example includes a capillary made of glass blown in the curved shape, which can allow sample loading onto the microfluidic device and/or fluid connection between channels or portions of a channel. Other manufacturing techniques and materials, including injection molding or extrusion of plastics, can also be used.

As shown in the embodiments illustrated in FIGS. 9A-9F, monolithic devices 800 and 830 having hollow, elongated volumes (e.g., microchannels 804) may be used as fluidic connectors. The devices may be rigid (e.g., for avoiding the need for the user to bend a capillary) and may optionally include a handle for simple handling (e.g., a vertical handle 810 as shown in FIG. 9B or a lateral handle 812 as shown in FIG. 9E). In some such embodiments, a loop of tubing of an U-shaped capillary can be replaced by microchannels 804 having any suitable dimensions formed in a substrate 816. The dimensions of the microchannels can be tuned to accommodate a wide range of volumes of fluid (e.g., 1-1000 µL). Such devices can be filled entirely with a fluid (e.g., sample) or may be filled partially with fluid (e.g., using a volume control element to meter the amount of fluid in the fluid path). Moreover, the dimensions of the microchannels can also be chosen to allow the introduction of the fluid in the channels with capillary forces, or alternatively, the fluid can be aspirated using vacuum.

The channels may be covered by a cover (e.g., covers 820 and 822), which may be, for example, a block, an adhesive film, or a tape. The device presented in FIGS. 9A-9C may require a bonding step (e.g., by use of an adhesive) between cover 820 and substrate 816. In some embodiments, such a bonding step may avoided by applying a cover 822 such as an adhesive film (e.g., tape) over the surface of the device (FIGS. 9D-9F).

As illustrated in FIGS. 9A and 9D, devices 800 and 830 may include access ports 806 and 808 (e.g., inlets and outlets) that can allow a fluid to be introduced into the fluid path and/or to enable fluid communication between channels (or portions of a channel) of a microfluidic system. The access ports can have any suitable shape to allow formation of a tight seal with the ports of the microfluidic system. As shown in the embodiments illustrated in FIG. 9, the ports may have a conical shape that are complementary to conical apertures of a microfluidic device.

In some embodiments, once a fluidic connector is connected to a microfluidic device (e.g., the devices shown in FIGS. 1, 3, and 4), a vacuum is applied to an outlet of the device to cause fluid flow in the system. In these embodiments, the vacuum may strengthen the quality of the seal between the complementary ports.

Figures 10A, 10B:
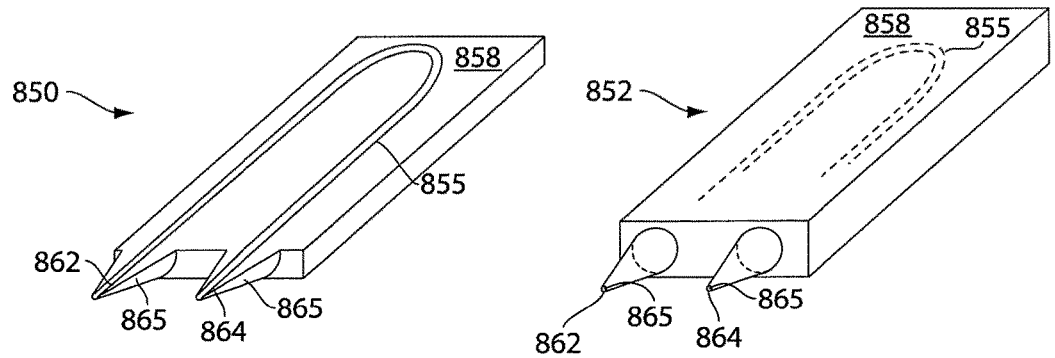
FIGS. 10A and 10B are schematic diagrams of another fluidic connector according to an embodiment of the invention.

Another example of a fluidic connector is shown in FIGS. 10A and 10B. In the embodiments illustrated in FIGS. 10A and 10B, fluidic connector 852 is prepared by assembling two parts 850. Fluidic connector 852 shows the implementation of a fluid path 855 within a rigid substrate 858, although in other embodiments, any arbitrary geometry can be used including a meandering channel configuration. The inlet and outlet ports 862 and 864 may be part of a conical protrusion 865 to form an air-tight seal with the conical apertures of the microfluidic chip. As described in more detail below, a more elaborate connection system can be implemented, such as snapping mechanisms or non-conical fittings. The fluidic connector can be optimized to allow simple handling for the user (including the addition of a handle to the design), if desired.

Figures 11A, 11B:
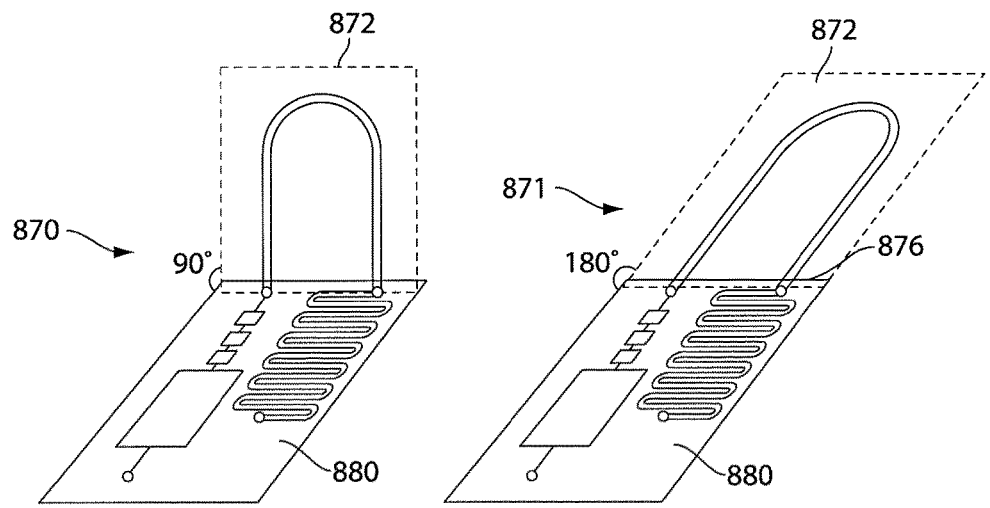
FIGS. 11A and 11B are schematic diagrams of fluidic connectors that can be connected orthogonally or on the same plane as the channels of a microfluidic system according to an embodiment of the invention.

In some embodiments described herein, the fluidic connector is connected to a microfluidic device (e.g., a substrate including microfluidic channels disposed therein), by inserting the ports of the fluidic connector in access holes located directly above the microchannel(s) of the substrate. As a result, the fluid path of the fluidic connector may be in a plane orthogonal to the plane of the microchannels of the substrate, as shown in FIG. 11A. In some applications, however, there are advantages to placing the fluidic connector in the same plane as the microchannel network (e.g., using a lateral connection). One advantage of this configuration may be to maximize the area available for observation of the microfluidic device (e.g., for highly parallel assays). Another advantage may be to allow stacking of a large number devices on top of each other while allowing each device to be accessible to fluid dispensers or other instruments, which can save storage space in an instrument. In some such embodiments, a fluidic connector 872 may be connected to an end portion 876 of a substrate 880. In other cases, the fluidic connector may be connected to a substrate at an angle between 90 and 180 degrees or between 0 and 90 degrees. Accordingly, fluidic connectors described herein may be connected to a substrate in any suitable configuration.

The reliability and simplicity of forming a good (e.g., fluid-tight) seal between a fluidic connector and a microfluidic substrate is a critical design aspect of a device for its use in point-of-care settings. In that regard, the fluidic connector can include additional features to help the user insert the device onto the microfluidic substrate. For instance, in one embodiment, the fluidic connector includes at least one non-fluidic feature complementary to a feature of the substrate so as to form a non-fluidic connection between the fluidic connector and the substrate upon attachment. The non-fluidic complementary feature may be, for example, a protruding feature of the fluidic connector and corresponding complementary cavities of the microfluidic substrate, which can help the user align the fluidic connector with the substrate. Moreover, these guiding features can also help maintain the device in place. In other instances, the substrate includes protruding features complementary to cavities of the fluidic connector.

FIGS. 12A-12E illustrate embodiments that enable attachment of a fluidic connector to a microfluidic substrate by snapping the two components together to form a connection. This configuration may be especially useful for applications involving point-of-care diagnostics, since the snapping mechanism may enable a good seal between the components, and may decrease the chance of the user mishandling the diagnostic test. The noise and/or feel experienced by the user while snapping the fluidic connector into the substrate can be used as a guide or control for successful attachment of the components.

Figure 12A:
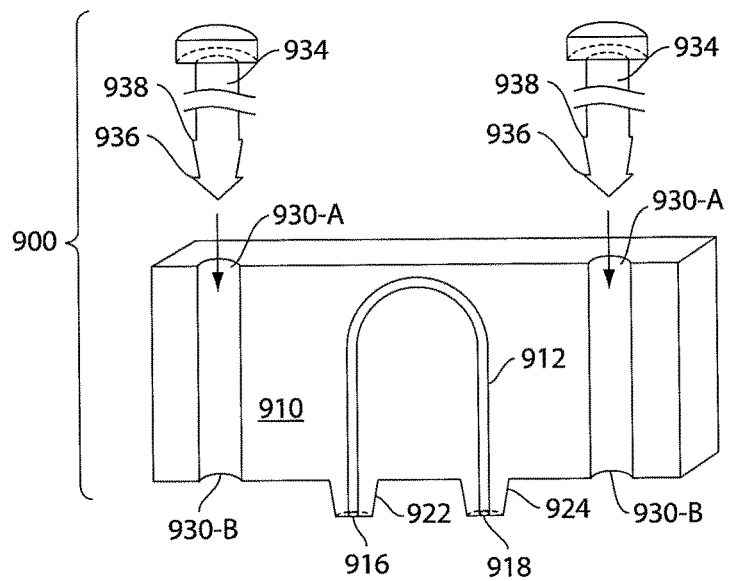
FIGS. 12A-12E are schematic diagrams of a fluidic connector including clips that can be used to attach the fluidic connector to a substrate according to an embodiment of the invention.
Figure 12B:
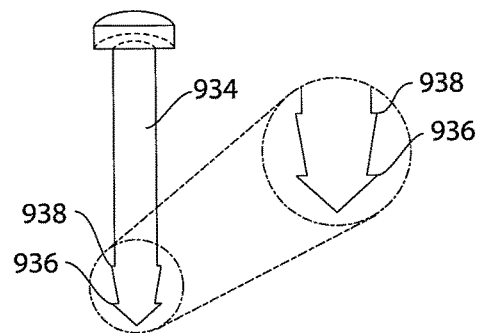

As illustrated in FIG. 12A, a fluidic connector 900 can include two identical first portions 910 (only one is shown) that form a fluid path 912 upon closing both halves against each other. In other instances, the fluidic connector includes a single integral piece including a fluid path 912 disposed therein. End portions 916 and 918 (e.g., an inlet and outlet) of the fluid path may be connected to a microfluidic substrate (not shown) via features 922 and 924, which may be complementary to features of the substrate. The fluidic connector may also include openings 930 for inserting clips 934. The clips may include two or more snap features (e.g., indentations) 936 and 938; these features may be formed of any suitable material (e.g., a polymer) and may be formed of the same or a different material than that of the clip and/or the substrate. Feature 938 may be used to connect the clip to first portion 910, and feature 936 may be used to connect the clip to the microfluidic substrate. Such features may allow the clip to be irreversibly attached to the fluid connector and/or to the substrate. FIG. 12B illustrates a magnified view of the clip. In other embodiments, the fluidic connector can be manufactured with the snap features, which can be directly a part of 910; for example, the fluidic connector may include feature 936 without the use of clip 934 (not shown).

Figure 12C:
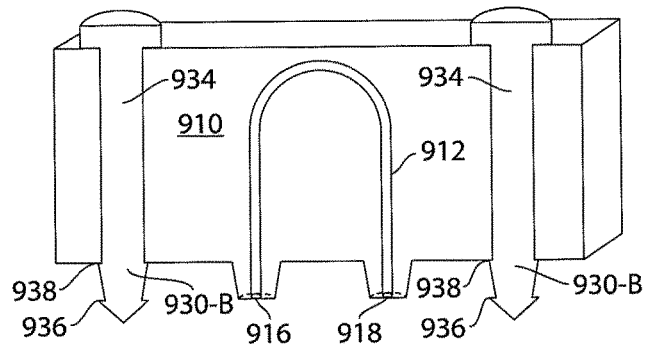
Figure 12D:
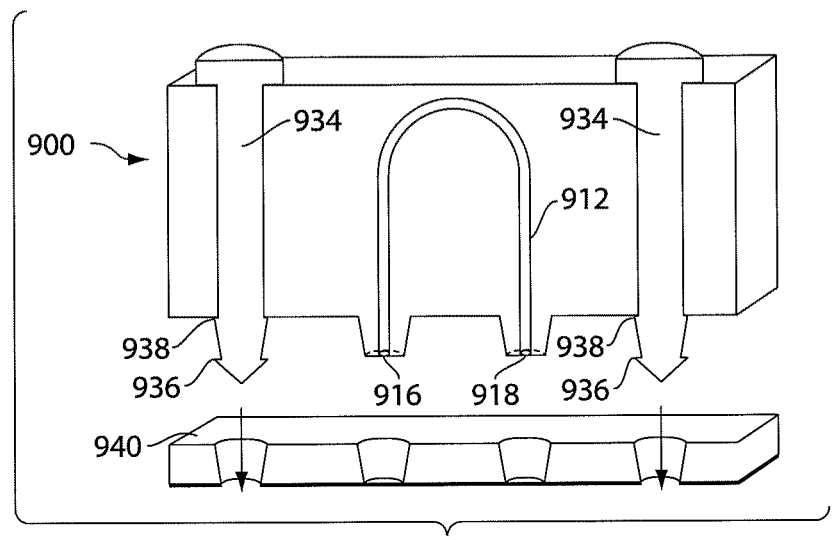
Figure 12E:
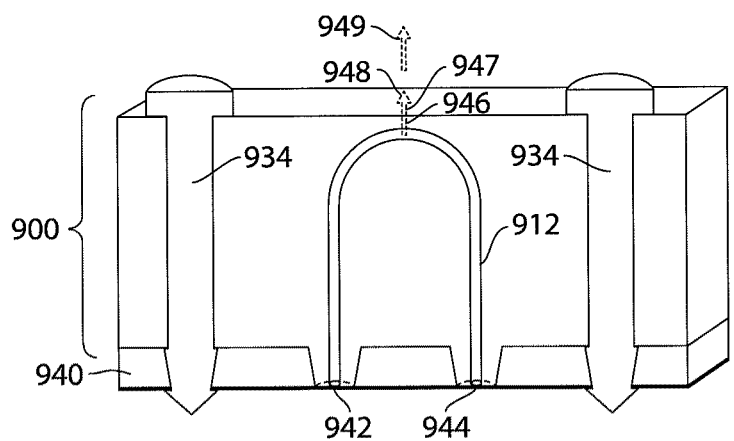

As shown in the embodiment illustrated in FIG. 12C, once a clip is inserted into openings 930 (e.g., when feature 938 meets opening 930-B), the clip may be attached to portion 910 of the fluidic connector. Likewise, as illustrated in FIG. 12D, the fluidic connector may be inserted into a portion of a microfluidic substrate 940 to cause attachment of the fluidic connector to the substrate (FIG. 9E). The snap features can guide the fluidic connector to the correct position in the microfluidic substrate. As described in more detail below, the attachment of a fluidic connector to a substrate may be reversible or irreversible. This attachment can cause fluid communication between a first channel at position 942 of the substrate and a second channel (or a portion of the first channel) at position 944 of the substrate via fluid path 912. As described herein, the fluidic connector may be loaded with a sample (e.g., via end portion 916 or 918) before or after attachment.

Figure 13:
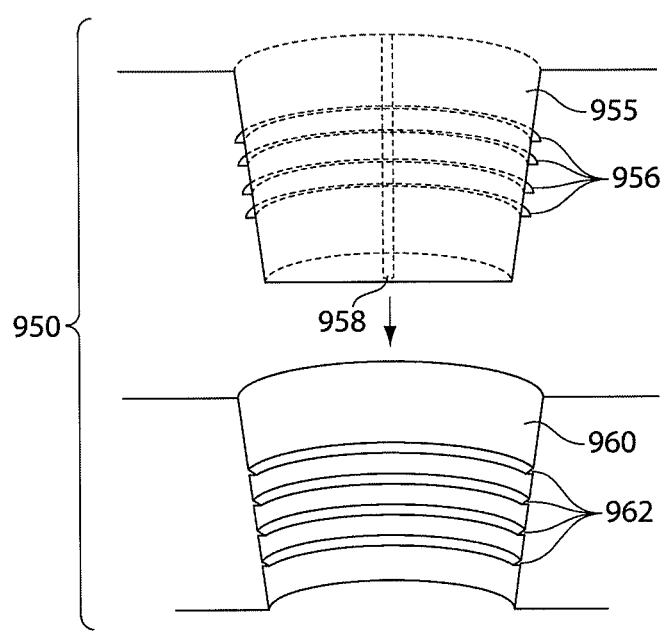
FIG. 13 is a schematic diagram of features that can be included on, for example, a fluidic connector and/or a substrate to secure attachment between the connector and substrate according to an embodiment of the invention.

As an alternative to the snapping mechanism described in connection with FIGS. 12A-12E, a fluidic connector can be attached to a microfluidic substrate using a zip-tie mechanism, as illustrated in FIG. 13. FIG. 13 shows a component 955 including features 956 (e.g., protrusions) that are complementary to portion 960, which includes features 962 (e.g., indentations). Component 955 may be a part of a fluidic connector and portion 960 may be part of a microfluidic substrate. In some instances, component 955 includes a fluid path 958 disposed therein.

Although features for connecting an article and a substrate, such as those shown in FIGS. 9, 10, 12 and 13, are described in reference to fluidic connectors and substrates, such features may also be used for connecting other articles of a device. For instance, such features may be used for connecting components such as an open-ended fluidic device and a substrate, a substrate and a cover, and/or multiple substrate layers of a device.

In embodiments described herein involving an article (e.g., a fluidic connector) comprising at least one feature complementary to a feature of the substrate, the features may be designed to form a reversible connection between the article and the substrate. Such embodiments may be useful, for example, for reusable devices. In other embodiments, such complementary features form an irreversible connection between the article and the substrate. The irreversible connection may cause the article and the substrate to be integrally connected. As used herein, the term "integrally connected," when referring to two or more objects, means objects that do not become separated from each other during the course of normal use, e.g., cannot be separated manually; separation requires at least the use of tools, and/or by causing damage to at least one of the components, for example, by breaking, peeling, or separating components fastened together via adhesives or tools. Devices including features forming an irreversible connection may be useful, for example, for one-time-use (e.g., disposable) devices. Such devices may form an irreversible connection so that the user cannot interfere with a chemical and/or biological reaction being performed in the device after connection.

The examples illustrated in FIGS. 12 and 13 include more than two connections (e.g., fluidic or non-fluidic connections) between a fluidic connector and a microfluidic substrate. This characteristic may be useful because additional points of connection (e.g., non-fluidic connections) can increase the stability of the attachment against mechanical stress (e.g., due to handling by the user) and shocks (e.g., improper use of the device). Additionally, each additional point of connection can increase the area of contact between the fluidic connector and the substrate, while the area associated with forming the fluid-tight seal between the fluidic connector and the substrate can remain unchanged. Alternatively, a single non-fluidic connection may be sufficient to yield good sealing properties.

Although many embodiments described herein include sample introduction components (e.g., fluidic connectors) having a single fluid path, it should be understood that a sample introduction component may include more than one fluid path and/or branching fluid paths. For example, as shown in the embodiment illustrated in FIG. 12E, fluidic connector 900 may optionally include a secondary flow path 946, which connects inlet 947 to flow path 912. This design can allow, for example, the introduction of a fluid into fluid flow path 912 via inlet 947 and secondary path 946 after fluidic connector 900 has been connected to a substrate. Alternatively, a fluid can be introduced into fluid path 912 via inlet 947 prior to connection of the fluidic connector and substrate.

In addition, sample introduction components such as fluid connectors described herein may include one or more sampling elements used to receive a fluid sample from a biological entity. The sampling element may be in the form of a needle or swab, for example. The sampling element may be reversibly or irreversibly attached to a sample introduction component. In some instances, the sampling element can puncture a biological component. For instance, as shown in the embodiment illustrated in FIG. 12E, fluidic connector 900 may include a (sterilized) sampling element 948, e.g., in the form of a hollow, sharp point (e.g., a needle), that may be used to puncture a component such as human skin. This configuration can allow the sampling element to receive a fluid sample from the biological component and can enable transfer of a fluid from the biological entity to fluid path 912 (e.g., by capillary forces). After fluid has been introduced into inlet 947, secondary fluid path 946 can be blocked, e.g., using component 949, which may have a shape complementary to that of fluid path 946. This blocking can prevent fluid from re-entering the secondary fluid path such that there is only one fluid path for flow. This arrangement can also prevent the user from being exposed further to sampling element 948.

In another embodiment, component 949 (optionally including a fluid path) can be used to obtain a sample, and upon insertion of the component into secondary fluid path 946, the sample can be transferred from the component to fluid path 912. In certain embodiments, insertion of the component prevents fluid from re-entering the secondary fluid path such that there is only one fluid path for flow.

In some embodiments, a sample introduction component includes a sampling element connected directly to a primary fluid path. For instance, in the embodiment illustrated in FIG. 10, conical protrusions 865, which may be complementary to a feature of a microfluidic substrate, may include sampling elements at the ends that can allow puncture of a biological component. Sampling elements may also be present as part of an open-ended fluidic device (e.g., as shown in FIG. 8A) and/or other fluidic connectors described herein (e.g., FIG. 8B).

There are several advantages of using microfluidic devices with fluidic connectors, especially when performing chemical and/or biological reactions (e.g., immunoassays) in the device. Accordingly, devices described herein may have one or more advantages such as: (a) use of small amounts of sample with little or no sample waste, (b) long-term stability of chemical and/or biological reagents stored in the device, (c) reduction of cross-contamination between stored reagents and/or between sample and reagent, (d) sample metering, (e) ease of use to untrained users for introducing a sample into the device, (f) efficient mixing of reagents, and (g) assay reliability. In some embodiments, the devices have all of the advantages listed above.

Small amounts of sample can be used with little or no sample waste because fluidic connectors (as well as open-ended fluidic devices) can be designed to have an internal volume matching the volume of sample required for performing the chemical and/or biological reaction. This can reduce the amount of dead volume in a system. Optionally, as described above, fluidic connectors and open-ended fluidic devices can include one or more volume control elements to allow collection of a particular volume of sample.

Devices described herein may be used for point-of-care applications, and can be manufactured several months (or years) prior to first use. In some embodiments requiring storage of components in the device prior to first use, it is important that all biomolecules and reagents introduced at the time of manufacturing remain stable for extended periods of time. For example, in a reaction area, capture antibodies can be physisorbed to the surface of the microchannels, and can be stabilized in a dry form using stabilizers (e.g., trehalose).

It has been demonstrated previously that the storage of the reagents in the form of liquid plugs separated by air gaps were stable for extended periods of time (see, for example, International Patent Publication No. WO2005/072858 (International Patent Application Serial No. PCT/US2005/ 003514), filed Jan. 26, 2005 and entitled "Fluid Delivery System and Method," which his incorporated herein by reference in its entirety).

Both liquid and dry reagents may be stored on a single microfluidic substrate. As described herein, in some embodiments, a channel containing a liquid reagent is not in fluid communication with a channel containing a dry reagent since, depending on the particular environmental (e.g., storage) conditions, if the channels containing the reagents are in fluid communication with one another, transport of water vapors can result in the wet reagent drying out and dry molecules being hydrated. This can affect the long-term stability of all reagents stored on certain devices. Likewise, in some embodiments, prior to use of the device, a stored liquid reagent is not in fluid communication with an absorbent material associated with a liquid containment region. A system involving the use of a fluidic connector and a microfluidic substrate including dry reagents and/or an absorbent material physically separated (e.g., in different channels) and not in fluidic communication with the wet reagents can allow fluid communication only at the time of use of the microfluidic device. This configuration can enhance the stability of the reagents for long-term storage. In other embodiments, however, liquid and dry reagents can be stored in fluid communication with one another and/or a liquid reagent can be in fluid communication with an absorbent material prior to use of the device (e.g., for short-term storage).

Another advantage of microfluidic devices described herein may be reduction of cross-contamination between stored reagents and/or between sample and reagent. Cross contamination may occur, in certain embodiments, at intersections between microfluidic channels, where plugs of reagents can get caught. These reagents can contaminate subsequent reagents flowing past the same intersection. The use of a fluidic connector can greatly simplify a microchannel network, reducing or obviating the number of intersection(s) on a device, and thus any potential cross-contamination problems.

Sample metering is another important requirement for many microfluidic applications. Often this is performed off-chip and an accurate sample volume is loaded onto the chip with the hope that the entire volume will flow inside the device. With fluidic connectors described herein, the volume of sample that can be introduced inside the microfluidic device can be accurately measured, and the entire volume of sample can be sent to a reaction area of the device.

As described herein, several designs of sample introduction components (e.g., fluidic connectors and open-ended fluidic devices) can be used by untrained users (see, for example, the embodiments described in connection with FIGS. 8-13). These components can be designed to facilitate the sample loading procedure and to allow simple attachment of a fluidic connector to a microfluidic substrate. Such devices may be especially useful in point-of-care settings by untrained users.

Another advantage of systems and methods described herein may include efficient mixing of reagents on a device. An example of efficient mixing has been described herein in connection with silver enhancement chemistry based on the reduction of silver ions by a reducing agent (e.g., hydroquinone) by a catalyst (e.g., a noble metal). In embodiments involving immunoassays, secondary antibodies can be labeled with gold colloids (catalyst). In the presence of a mixture of silver ions and hydroquinone, multiple layers of silver can be created at the surface of the gold colloid, increasing the size of the colloid. After about 10 minutes of amplification, the size of the colloid can increase by a factor of, for example, about 1000, yielding on the surface grains of silver that can be observed with an optical setup. To achieve good amplification results (e.g., a large signal amplification with little amplification of background), the amplification reagent can be stored separately, e.g., in separated channels or containers, and mixed only immediately before use. In microfluidic devices, the cross-sectional dimensions of the channel may be small and flows may be laminar, meaning mixing occurs primarily by diffusion, which is typically inefficient and slow. However, the laminar character of the flow of reagents may be decreased when traveling through a fluid path of a fluid connector, since the fluid path may have a relatively larger cross-sectional dimension (and, therefore, a relatively larger volume) than the that of the microchannels of the substrate. Accordingly, in certain embodiments, each fluid connector can act as a chaotic mixer and can significantly improve the mixing of two or more reagents. In the example described above, this mixing can improve the reproducibility of the amplification chemistry.

In some embodiments described herein, microfluidic devices include only a single interconnected channel with, for example, less than 5, 4, 3, 2, or 1 channel intersection(s) when in use (e.g., upon attachment of a fluidic connector and a substrate). A layout based on a single channel with minimal or no intersections may be reliable because there is only one possible flow path for any fluid to travel across the microfluidic chip. In these configurations, the reliability of a chemical and/or biological reaction to be performed in the device is greatly improved compared to designs having many intersections. This improvement occurs because at each intersection (e.g., a 3-way intersection or more), the fluid has the potential to enter the wrong channel. The ability to load a sample without channel intersections can eliminate risk of fluid entering the wrong channel. Because an intersection may represent a risk factor that must be taken into account in product development, controls (either on-chip or based on external inspection) must be set up to insure correct fluid behavior at each interconnection. In certain embodiments described herein, the need for such additional controls can be alleviated.

As described above, reagents can be stored in a microfluidic device using a variety of methods. Such methods may depend at least in part on the form in which the reagent is stored (e.g., dried or wet), the configuration of the channels within microfluidic system (e.g., whether the channels are interconnected or unconnected), the length of time of storage, and/or the particular application.

Referring back to FIG. 2, in some embodiments, a first reagent (or series of reagents) is positioned in a first channel formed in a substrate, such as in a channel or reservoir of reagent storage area 64. A second reagent (or series of reagents) may be positioned in a second channel formed in a substrate, such as a channel or reservoir of immunoassay area 68. In some cases, the first and second channels are not in fluid communication with one another during the positioning of the reagents. The first and/or second reagent may be positioned in their respective channels by first flowing the reagents in the channels and then sealing any inlet(s) and/or outlet(s) of the channels.

The first and/or second reagents may be substantially altered after being positioned in their respective channels. For instance, in some cases the first and/or second reagents is dried after flowing the reagent(s) in a channel. Optionally, the dried reagents may be treated with a third reagent (e.g., a blocking agent) which may, for example, reduce non-specific adsorption during carrying out of an assay. The dried reagent(s) may be stored in a channel by sealing one or more inlets and/or outlets of the microfluidic channel.

In some instances, a reagent is positioned in a channel prior to complete fabrication of a microfluidic channel system. A microfluidic channel system is not complete if, for example, a system that is designed to have enclosed channels has channels that are not yet completely enclosed. A channel is enclosed if at least one portion of the channel has a cross-section that is completely enclosed, or if the entire channel is completely enclosed along its entire length with the exception of its inlet(s) and/or outlet(s).

In some embodiments, one or more reagents is positioned on a detection zone of a substrate by placing a droplet of the reagent at the detection zone (e.g., detection zones 162, 164, 166, and 168 of FIG. 3). The substrate may be formed of a hydrophobic material, which can prevent spreading of aqueous reagents across adjacent detection zones. The reagents at the detection zones may be dried and a cover may be placed adjacent the substrate to complete fabrication of the channel system. Subsequently, any inlet(s) and/or outlet(s) of the channel can be sealed.

In another embodiment, one or more reagents is positioned (e.g., patterned) on a cover, and then the cover is used to enclose a microfluidic channel system formed in a substrate. The reagents on the cover may be aligned with certain areas within the microfluidic system. For instance, in one particular embodiment, reagents (e.g., antibodies) are patterned in an arrangement (e.g., shape and dimension) that is matched with detection zones 162, 164, 166, and 168 of FIG. 3. The reagents can be dried, and then the cover can be sealed against the substrate such that the reagents are positioned in the detection zones of the microfluidic system. The cover can be, for example, a biocompatible adhesive (e.g., prepared on a substrate) and can be made of a polymer (e.g., PE, COC, PVC) or an inorganic material. For some applications, the material and dimensions of a cover are chosen such that the cover is substantially impermeable to water vapor. In other embodiments, the cover can be non-adhesive, but may bond thermally to the microfluidic substrate by direct application of heat, laser energy, or ultrasonic energy. Any inlet(s) and/or outlet(s) of the channel can be sealed (e.g., by placing an adhesive, membrane, or a septum over/in the inlet(s) and/or outlet(s)) after introducing reagents into the device.

Wet reagents are typically stored in a microfluidic system after channels of the system have been completely covered. A fluid reagent to be stored in the system may be introduced into an inlet of a channel, and after at least partially filling the channel with the fluid, the inlet(s) and/or outlet(s) of the channel can be sealed, for example, to retain the fluid and to prevent contamination from external sources.

In some instances, one or more fluids to be stored in a microfluidic system is transferred from a vessel (e.g., a cartridge or tube) to the microfluidic system. The vessel may contain, for example, two or more distinct fluids separated by a third fluid that is immiscible with both. Any number of distinct fluids may be contained in a vessel. For example, in one embodiment, the vessel is a tube that includes a reagent solution plug followed by an air plug, followed by a rinse solution plug. An additional air plug may separate the first rinse solution plug from a second rinse solution plug. The liquid plugs may retain their relative positions in the tube and may be prevented from contacting each other by the interspaced air plugs. Articles and methods for delivering fluids to a microfluidic system are described in more detail in International Patent Publication No. WO2005/072858 (International Patent Application Serial No. PCT/US2005/003514), filed Jan. 26, 2005 and entitled "Fluid Delivery System and Method," which his incorporated herein by reference in its entirety.

Using a vessel containing fluid plugs in linear order can allow introduction of fluid from the vessel to a microfluidic system in a particular sequence. These fluids can then be stored in the particular sequence in the microfluidic system (e.g., in a reagent storage area). The inlet(s) and/or outlet(s) of the channel containing the fluids can be sealed, for example, to retain the fluid and to prevent contamination from external sources.

Reagents can be stored in a microfluidic system for various amounts of time. For example, a reagent may be stored for longer than 1 hour, longer than 6 hours, longer than 12 hours, longer than 1 day, longer than 1 week, longer than 1 month, longer than 3 months, longer than 6 months, longer than 1 year, or longer than 2 years. Optionally, the microfluidic system may be treated in a suitable manner in order to prolong storage. For instance, microfluidic systems having stored reagents contained therein may be vacuum sealed, stored in a dark environment, and/or stored at low temperatures (e.g., below 0 degrees C.). The length of storage depends on one or more factors such as the particular reagents used, the form of the stored reagents (e.g., wet or dry), the dimensions and materials used to form the substrate and cover layer(s), the method of adhering the substrate and cover layer(s), and how the device is treated or stored as a whole.

As described herein, different sections of a microfluidic channel or reservoir, especially within a reaction area, can be each modified with a different species (e.g., capture molecule) that can be stored in the channel or reservoir, so that a sample traveling throughout the microchannel channel can travel successively over each of the species. The sections of the microfluidic channel may be, for example, detection zones (e.g., meandering channel regions) as described herein in connection with FIGS. 2-7 and 14-17. In some embodiments, these sections are connected in series. In other embodiments, the sections are connected in parallel. In yet other embodiments, a device may include a combination of sections connected in series and parallel. In embodiments including detection zones connected in series (and/or in parallel), multiple components of the sample can be tested individually in each of the detection zones of the channel. The detection zones may have different configurations depending on the application; for example, a detection zone may be in the form of a reservoir (which may be supported by an array of pillars) or a meandering channel region, as described in further detail below. In certain embodiments, a device includes a plurality (e.g., at least 2, 4, 6, 8, 10, or more) of sections, each section comprising a single chemical and/or biological species that can undergo a chemical and/or biological reaction (or which may be unreactive towards particular components of a sample, as in a negative control). The chemical and/or biological species in one section may be the same (e.g., same species and concentration) or different (e.g., different species and/or concentration) as the species of another section.

To simplify signal quantification, each detection zone (e.g., meandering channel region) may have a relatively large area compared to a cross-sectional dimension of a microfluidic channel of the system. For example, the detection zone may have an area of greater than 0.1 mm$^2$, greater than 0.2 mm$^2$, greater than 0.4 mm$^2$, greater than 0.6 mm$^2$, greater than 0.8 mm$^2$, or greater than 1 cm$^2$. The area may be, for example, between 0.1 mm$^2$ to 0.3 mm$^2$, between 0.2 mm$^2$ to 0.4 mm$^2$, between 0.4 mm$^2$ to 0.6 mm$^2$, or between 0.5 mm$^2$ to 1 cm$^2$. Different proportions of the detection zone may comprise an optical detection pathway. For example, at least 20%, at least 40%, at least 50%, at least 60%, or at least 80% of the area of the detection zone may comprise an optical detection pathway. The area spanned by the detection zone may be defined by the rectangular area bound by outermost points of the detection zone along each axis. A signal produced in the detection zone may be homogeneously spread over a large area, thus simplifying the alignment of an optical readout device.

Figure 14A:
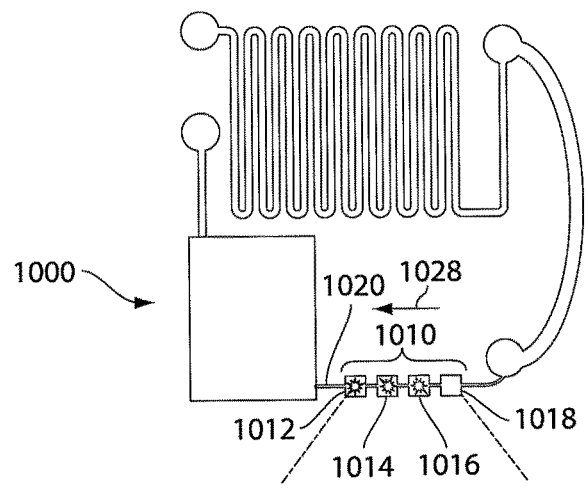
FIGS. 14A-14C are schematic diagrams of a device including detection zones in the form of meandering regions according to an embodiment of the invention.
Figure 14B:
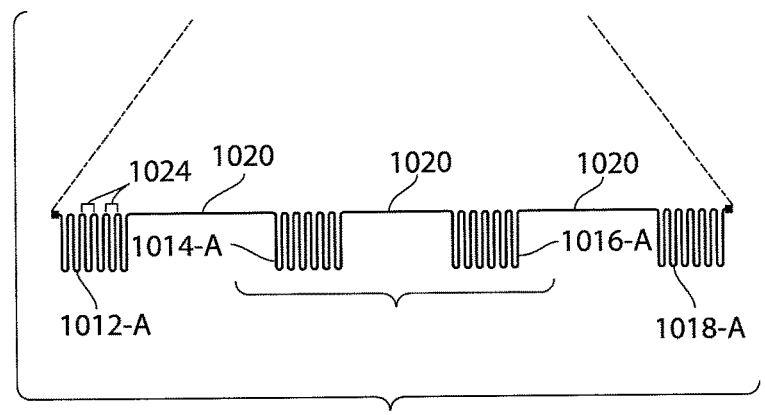
Figure 14C:
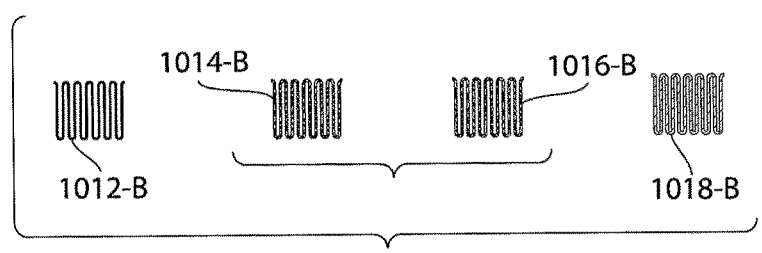

As shown in the embodiments illustrated in FIGS. 14A-14C, device 1000 may include a reaction area 1010 having several detection zones 1012, 1014, 1016, and 1018. Each of these detection zones may be in the form of a meandering region 1012-A, 1014-A, 1016-A, and 1018-A, respectively (FIG. 14B). The meandering regions include several channel segments 1024. The meandering regions can be connected to one another (i.e., in fluid communication with one another) via microfluidic channel 1020. Fluid flowing in channel 1020, e.g., in the direction of arrow 1028, can flow through the meandering regions sequentially.

As described herein, a surface of the meandering channel in each meandering region can be modified with one or more biomolecules (e.g., in the form of a stored reagent) for a particular application. To provide on-chip quality control, meandering region 1018-A can be modified with a blocking solution such as BSA or Tween 20 to provide a negative reference for the assay. In a similar fashion, meandering region 1012-A can be modified with a positive control. The choice of these standards may be such that after successful assay completion, the negative standard should indicate no signal (or very weak background signal), and the positive signal should indicate a clear signal. In general, the choice of the reagent/biomolecule to be immobilized in each meandering region can be governed by the particular test to be performed; for example, for the measurement of total human IgG in serum, anti-human antibodies can be physisorbed in meandering regions 1014-A and 1016-A.

FIG. 14C is a schematic diagram showing the meandering regions after performing a chemical and/or biological reaction in the meandering regions. Meandering region 1018-B used as a negative control has a weak signal and appears light grey. Meandering regions 1014-B and 1016-B that included physisorbed reagents that can be used for determining a component in the sample may include a detectable signal (e.g., a gray film). Meandering region 1018-B used as a positive control may include a strong signal (e.g., a black film).

FIGS. 14A-14C show an example of a multiplex assay that can be performed in a microfluidic device described herein. In other embodiments, additional meandering regions (e.g., greater than 5, 8, 10, 15, or 20 meandering regions, which may be connected in series and/or parallel), can be included on a device to allow detection of additional components in a sample.

After performing a chemical and/or biological reaction in a detection zone (e.g., meandering region), a signal may appear in the detection zone. The type and strength of the signal may depend on the choice of label and/or amplification chemistry used. For example, in one embodiment, silver enhancement chemistry can be used to produce a signal that can be detected by a simple detector, such as the one described in International Patent Publication No. WO2005/066613 (International Patent Application Serial No. PCT/US2004/043585), filed Dec. 20, 2004 and entitled "Assay Device and Method", which is incorporated herein by reference in its entirety.

Figure 15A:
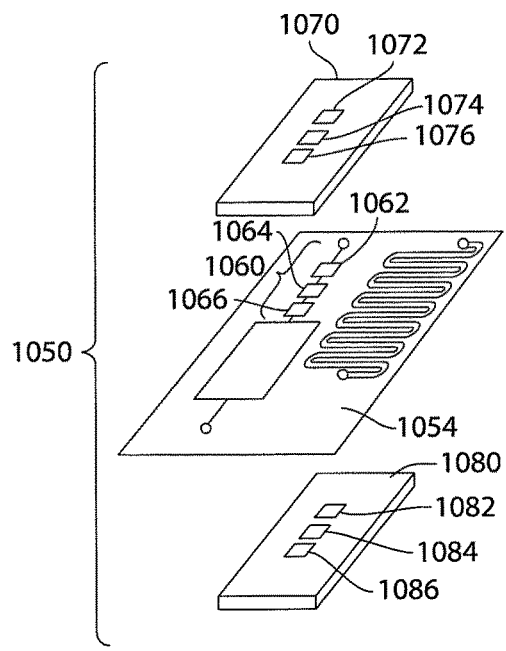
FIGS. 15A and 15B are schematic diagrams of an optical system for detecting a component in a detection zone of a device according to an embodiment of the invention.
Figure 15B:
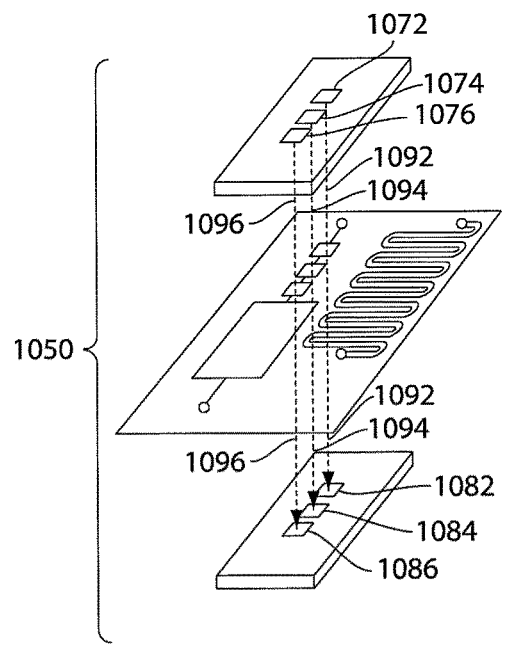
Figure 16:
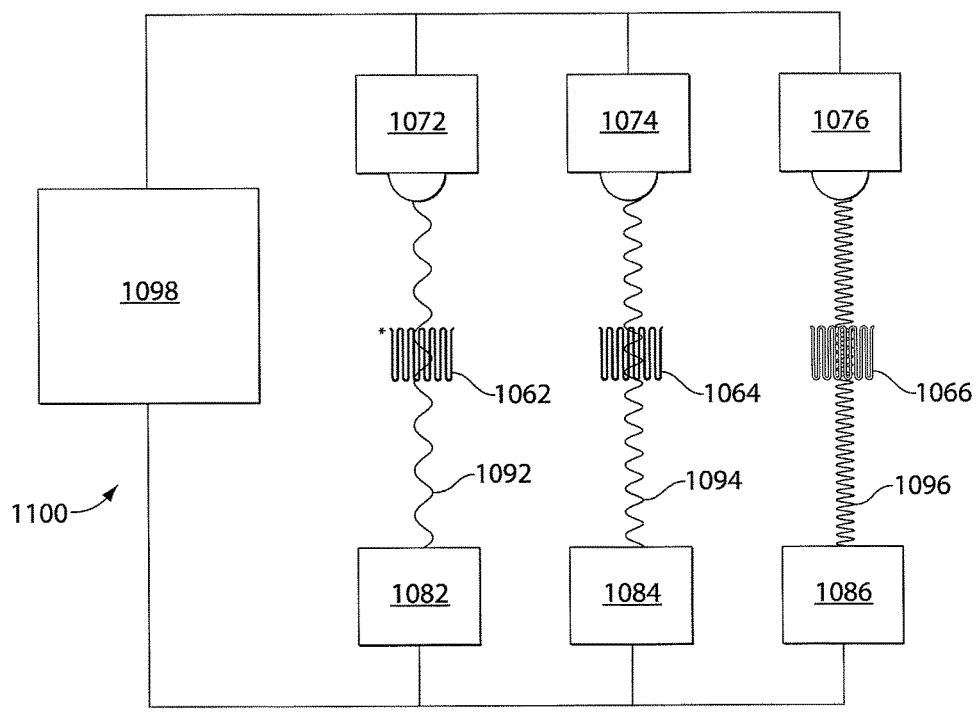
FIG. 16 is a schematic diagram of an optical system for detecting components in different detection zones of a device according to an embodiment of the invention.
Figure 17:
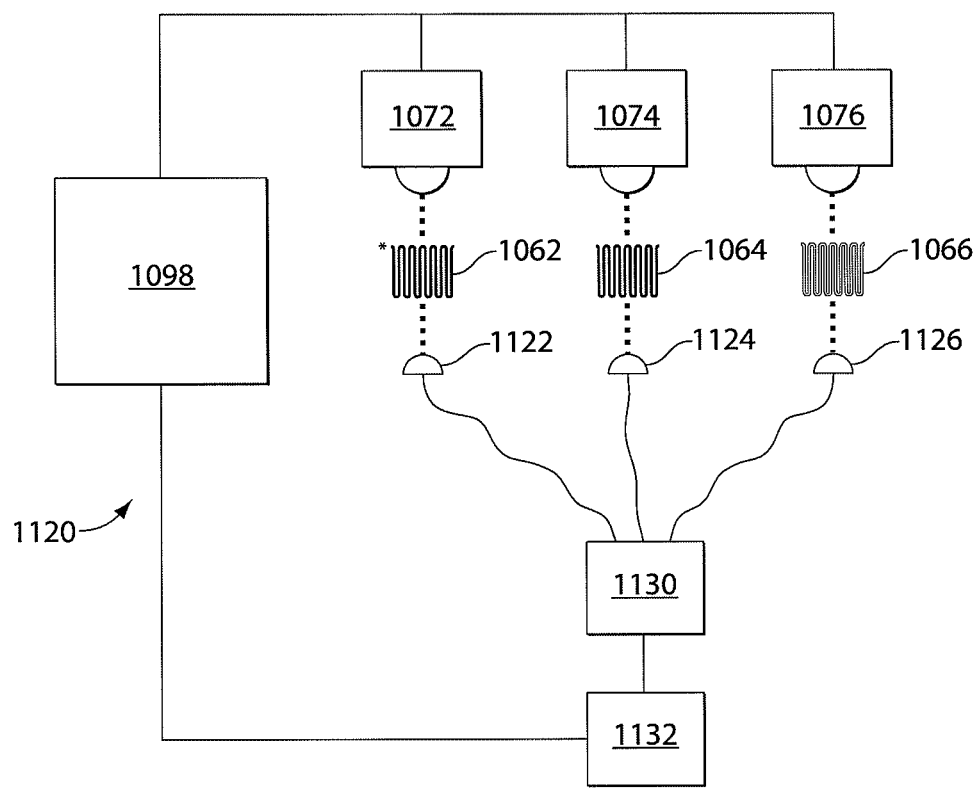
FIG. 17 is a schematic diagram of an optical system including an optical light source and a detector aligned with each detection zone of a device according to an embodiment of the invention.

When more than one chemical and/or biological reaction (e.g., a multiplex assay) is performed on a device, the signal acquisition can be carried out by moving a detector over each detection zone. In an alternative approach, a single detector can detect signal(s) in each of the detection zones simultaneously. In another embodiment, an analyzer can include, for example, a number of parallel optical sensors/detectors, each aligned with a detection zone and connected to the electronics of a reader (e.g., FIGS. 15A and 15B). FIGS. 15A and 15B illustrate an optical system 1050 at rest (FIG. 15A) and during measurement (FIG. 15B). As shown in the embodiment illustrated in FIG. 15A, optical system 1050 includes a device 1054 having a detection area 1060 including detection zones 1062, 1064, and 1066. The optical setup also includes an article 1070 comprising an array of light sources 1072, 1074, and 1076, as well as an article 1080 comprising an array of detectors 1082, 1084, and 1086. In some embodiments, articles 1070 and 1080 are combined to form an analyzer. The light sources and detectors may be aligned with the detection zones of the device. During measurement, an optical pathway 1092 between optical light source 1072, detection zone 1062, and detector 1082 allows determination of a signal in the detection zone. Parallel optical pathways 1094 and 1096 can allow simultaneous determination of signals in detection zones 1064 and 1066, respectively.

The interior of an analyzer can be designed to allow simultaneous reading (e.g., detection or determination of a signal) in all detection zones without interference between each optical pathway in the system. For example, in the embodiment illustrated in FIG. 16, system 1100 includes light source 1072 and detector 1082 aligned with each other and detection zone 1062. Additionally, light source 1074 can be aligned with detection zone 1064 and detector 1084 and light source 1076 can be aligned with detection zone 1066 and detector 1086. The light sources and detectors may be in electronic communication with control unit 1098 (e.g., a microprocessor). In some embodiments, one or more optical filters can be positioned between a detector and a detection zone. Additionally and/or alternatively, each detector may include an electronic filter for filtering different wavelengths of light. To further reduce cross-talk between optical pathways, the light from each light source can be modulated at a frequency different for each optical pathway; that is, optical pathways 1092, 1094, and 1096 may each include light of different wavelengths. The electronic signal generated by light source 1072 can be differentiated from noise signal arising from by neighboring light sources 1074 and 1076 by using, for example, an electronic filter. In a different approach, the readout can be performed sequentially to avoid noise signal(s) arising from the neighboring light sources. Using a light source-detector pair for each detection zone may be advantageous when the optical components are relatively simple and/or inexpensive.

In some embodiments, one or more optical components can be shared between detection zones. For instance, in the embodiment illustrated in FIG. 17, a system 1120 includes a detector 1072 and an optical element 1122 (e.g., a collecting optic such as an optical fiber), which are aligned with each other and with detection zone 1062. Similarly, the system includes a detector 1074 and an optical element 1124 aligned with detection zone 1064, as well as a detector 1076 and an optical element 1126 aligned with detection zone 1066. The optical elements may all be connected to an optical switch 1130 and to a common light detector 1132, such as an avalanche photodiode or a photomultiplier tube. The common detector may be used to detect signals in each of the detection zones (e.g., sequentially). The light from each detection zone can be collected by the optical elements, which can be aligned underneath each detection zone.

A variety of determination (e.g., measuring, quantifying, detecting, and qualifying) techniques may be used. Determination techniques may include optically-based techniques such as light transmission, light absorbance, light scattering, light reflection and visual techniques. Determination techniques may also include luminescence techniques such as photoluminescence (e.g., fluorescence), chemiluminescence, bioluminescence, and/or electrochemiluminescence. Those of ordinary skill in the art know how to modify microfluidic devices in accordance with the determination technique used. For instance, for devices including chemiluminescent species used for determination, an opaque and/or dark background may be preferred. For determination using metal colloids, a transparent background may be preferred. Furthermore, any suitable detector may be used with devices described herein. For example, simplified optical detectors, as well as conventional spectrophotometers and optical readers (e.g., 96-well plate readers) can be used.

In some embodiments, determination techniques may measure conductivity. For example, microelectrodes placed at opposite ends of a portion of a microfluidic channel may be used to measure the deposition of a conductive material, for example an electrolessly deposited metal. As a greater number of individual particles of metal grow and contact each other, conductivity may increase and provide an indication of the amount of conductor material, e.g., metal, that has been deposited on the portion. Therefore, conductivity or resistance may be used as a quantitative measure of analyte concentration.

Another analytical technique may include measuring a changing concentration of a precursor from the time the precursor enters the microfluidic channel until the time the precursor exits the channel. For example, if a silver salt solution is used (e.g., nitrate, lactate, citrate or acetate), a silver-sensitive electrode may be capable of measuring a loss in silver concentration due to the deposition of silver in a channel as the precursor passes through the channel.

Different optical detection techniques provide a number of options for determining reaction (e.g., assay) results. In some embodiments, the measurement of transmission or absorbance means that light can be detected at the same wavelength at which it is emitted from a light source. Although the light source can be a narrow band source emitting at a single wavelength it may also may be a broad spectrum source, emitting over a range of wavelengths, as many opaque materials can effectively block a wide range of wavelengths. The system may be operated with a minimum of optical devices (e.g., a simplified optical detector). For instance, the determining device may be free of a photomultiplier, may be free of a wavelength selector such as a grating, prism or filter, may be free of a device to direct or columnate light such as a columnator, or may be free of magnifying optics (e.g., lenses). Elimination or reduction of these features can result in a less expensive, more robust device.

In one embodiment, the light source can be pulse modulated, for example, at a frequency of 1,000 Hz. To match the pulse modulated light source, a detector may include a filter operating at the same frequency. By using a pulse modulated light source it has been found that the system can be less sensitive to extrinsic sources of light. Therefore, an assay may run under various light conditions, including broad daylight, that might make it impractical to use existing techniques. Experimental results indicate that by using a pulse modulated light source and filter, results are consistent regardless of the light conditions under which the test is run.

The light source may be a LED (light-emitting diode) or a laser diode. For example, an InGaAlP red semiconductor laser diode emitting at 654 nm may be used. The photodetector may be any device capable of detecting the transmission of light that is emitted by the light source. One type of photodetector is an optical integrated circuit (IC) including a photodiode having a peak sensitivity at 700 nm, an amplifier and a voltage regulator. If the light source is pulse modulated, the photodetector may include a filter to remove the effect of light that is not at the selected frequency. When multiple and neighboring signals are detected at the same time, the light source used for each detection zone can be modulated at a frequency sufficiently different from that of its neighboring light source. In this configuration, the detector can be assorted with a filter of matching fervency (compared to its attributed light source), thereby avoiding interfering light form neighboring optical pairs.

As described herein, a meandering channel of a reaction area may be configured and arranged to align with a detector such that upon alignment, the detector can measure a single signal through more than one adjacent segment of the meandering channel. In some embodiments, the detector is able to detect a signal within at least a portion of the area of the meandering channel and through more than one segment of the meandering channel such that a first portion of the signal, measured from a first segment of the meandering channel, is similar to a second portion of the signal, measured from a second segment of the meandering channel. In some such embodiments, because the signal is present as a part of more than one segment of the meandering channel, there is no need for precise alignment between a detector and a detection zone.

The positioning of the detector over the detection zone (e.g., a meandering region) without the need for precision is an advantage, since external (and possibly, expensive) equipment such as microscopes, lenses, and alignment stages are not required (although they may be used in certain embodiments). Instead, alignment can be performed by eye, or by low-cost methods that do not require an alignment step by the user. In one embodiment, a device comprising a meandering region can be placed in a simple holder (e.g., in a cavity having the same shape as the device), and the measurement area can be automatically located in a beam of light of the detector. Possible causes of misalignment caused by, for instance, chip-to-chip variations, the exact location of the chip in the holder, and normal usage of the device, are negligible compared to the dimensions of the measurement area. As a result, the meandering region can stay within the beam of light and detection is not interrupted due to these variations.

The detector may detect a signal within all, or a portion, of a detection zone (e.g., including a meandering region). In other words, different amounts of the meandering region may be used as an optical detection pathway. For instance, the detector may detect a signal within at least 15% of the detection zone, at least 20% of the detection zone, at least 25% of the detection zone, within at least 50% of the detection zone, or within at least 75% of the detection zone (but less than 100% of the detection zone). In some instances, 100% of the detection zone is used for detection by a detector (e.g., detection in a transparent channel by the unaided eye). The area in which the detection zone is used as an optical detection pathway may also depend on, for instance, the opacity of the material in which the channel is fabricated (e.g., whether all, or, a portion, of the channel is transparent), the amount of a non-transparent material that may cover a portion of the channel (e.g., via use of a protective cover), and/or the size of the detector and the detection zone.

In one embodiment, a signal produced by the reaction is homogenous over the entire detection zone (e.g., over an entire meandering channel region). That is, the detection zone (e.g., meandering channel region) may allow production and/or detection of a single, homogenous signal in said region upon carrying out a chemical and/or biological reaction (e.g., and upon detection by a detector). Prior to carrying out a reaction in the meandering channel region, the meandering channel may include, for example, a single species (and concentration of species) to be detected/determined. The species may be adsorbed to a surface of the meandering channel. In another embodiment, the signal may be homogeneous over only portions of the meandering region, and one or more detectors may detect different signals within each of the portions. In certain instances, more than one detection zone can be connected in series and each detection zone can be used to detect/determine a different species.

In some embodiments, a chemical and/or biological reaction involves binding. Different types of binding may take place in devices described herein. The term "binding" refers to the interaction between a corresponding pair of molecules that exhibit mutual affinity or binding capacity, typically specific or non-specific binding or interaction, including biochemical, physiological, and/or pharmaceutical interactions. Biological binding defines a type of interaction that occurs between pairs of molecules including proteins, nucleic acids, glycoproteins, carbohydrates, hormones and the like. Specific examples include antibody/antigen, antibody/hapten, enzyme/substrate, enzyme/inhibitor, enzyme/cofactor, binding protein/substrate, carrier protein/substrate, lectin/carbohydrate, receptor/hormone, receptor/effector, complementary strands of nucleic acid, protein/nucleic acid repressor/inducer, ligand/cell surface receptor, virus/ligand, etc.

In some cases, a heterogeneous reaction (or assay) may take place in a channel; for example, a binding partner may be associated with a surface of a channel, and the complementary binding partner may be present in the fluid phase. The term "binding partner" refers to a molecule that can undergo binding with a particular molecule. Biological binding partners are examples; for instance, Protein A is a binding partner of the biological molecule IgG, and vice versa. Likewise, an antibody is a binding partner to its antigen, and vice versa. In other cases, a homogeneous reaction may occur in the channel. For instance, both binding partners can be present in the fluid phase (e.g., in two-fluid laminar flow system). Non-limiting examples of typical reactions that can be performed in a meandering channel system include chemical reactions, enzymatic reactions, immuno-based reactions (e.g., antigen-antibody), and cell-based reactions.

In another embodiment of the invention, a microfluidic device developed to perform a specific clinical test is labeled with information specific to the test (e.g., name of the test, batch-specific data and expiration date). One or more components of the system, such as the sample introduction component, can be designed such that it is marked with patient-specific information (e.g., physically or electronically). Upon attachment of the sample introduction component to a microfluidic device (e.g., a microfluidic substrate, optionally in connection with other (e.g., electronic) components), the patient's information can become linked to the device and the particular test performed on the device. In some cases, e.g., for certain embodiments involving permanent attachment of the sample introduction component to a disposable microfluidic device (e.g., by zip tie or snapping mechanism as described above), the two sets of information (one from the sample introduction component and one from the microfluidic device) cannot be separated. This can provide a safe method for adding the patient's information onto the microfluidic device. For example, in one embodiment, a microfluidic device is labeled with test-specific information (e.g., name of the test, data for the test calibration, batch name and number), and the sample introduction component includes a surface that can accommodate a standard-sized sticker containing a code referring to the patient identity (e.g., a bar code).

As described above, another aspect of the invention involves a liquid containment region for containing and/or capturing one or more liquids in the device. Examples of liquid containment regions are shown in the embodiments illustrated in FIGS. 18A-23B.

Figure 18A:
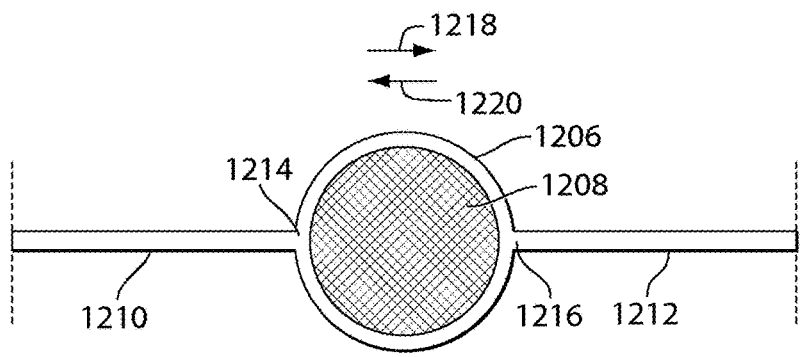
FIG. 18A is a schematic diagram showing a top view of a liquid containment region according to an embodiment of the invention.

As shown in the embodiment illustrated in FIG. 18A, a microfluidic system described herein may include a liquid containment region 1206 having contained therein an absorbent material 1208. The absorbent material can absorb at least one liquid in the microfluidic system and, optionally, may be designed to allow certain fluids to pass therethrough without being absorbed. As illustrated, the liquid containment region may be in fluidic communication with microfluidic channels 1210 and 1212. In some such embodiments, the liquid containment region includes openings 1214 and 1216 which may allow fluid to flow into and/or out of the liquid containment region, e.g., depending on the direction of fluid flow.

Fluid may flow into and/or out of the liquid containment region in any suitable manner. For instance, in one embodiment, fluids in channels 1210 and 1212 flow in the direction of arrow 1218. In another embodiment, fluids in channel 1210 and 1212 flow in the direction of arrow 1220. In yet another embodiment, fluids in channel 1210 flow in the direction of arrow 1218 and fluid flow in channel 1212 is in the direction of arrow 1220. In a further embodiment, fluid in channel 1210 flows in the direction of arrow 1218 but fluid may be prevented from flowing out of the liquid containment region through opening 1216 (e.g., by use of a valve or other component positioned at opening 1216). Other combinations of fluid flow are also possible. Furthermore, although one or more absorbent materials may be associated with a liquid containment region, in some embodiments the absorbent material is not used to control or vary the rate of fluid flow. Methods involving controlling fluid flow are described in more detail below.

Although the liquid containment region of FIG. 18A is shown to be in fluid communication with only two microfluidic channels, any suitable number of microfluidic channels may be associated with the liquid containment region. For instance, at least 1, 2, 3, 5, 8, 10, or 20 channels may be in fluid communication with a liquid containment region described herein.

Figure 18B:
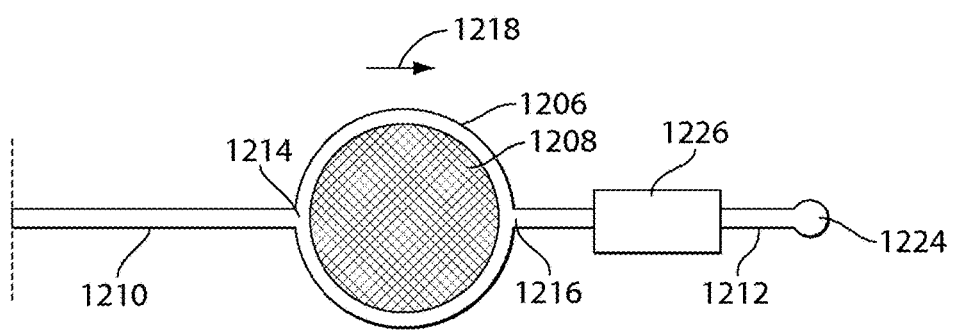
FIG. 18B is a schematic diagram showing a top view of a liquid containment region in fluid communication with an outlet according to an embodiment of the invention.

As shown in the embodiment illustrated in FIG. 18B, liquid containment region 1206 is positioned near an outlet

1224, the liquid containment region and outlet being separated by at least one microfluidic channel 1212. Accordingly, fluid may flow from the liquid containment region towards the outlet in the direction of arrow 1218. In other embodiments, the liquid containment region is positioned at the end of a microfluidic channel and an outlet is a part of the liquid containment region; e.g., the outlet may be positioned in the liquid containment region (not shown). In the configurations above, the liquid containment region may be used as a waste area, such as a waste area described in connection with FIGS. 3-7. In some such embodiments, liquid containment region 1206 may be positioned downstream of a reaction area, reagent storage area, and/or sampling loading area, the liquid containment region being used to contain, absorb, or capture one or more liquids in a stream of fluid flowing in the microfluidic system. In some cases, absorption of liquid is performed while removing gas bubbles from the stream of fluid, resulting in the release of the gas at the outlet. Optionally, a source of vacuum may be connected to the outlet for controlling fluid flow in the device.

Microfluidic channel 1212, a connecting microfluidic channel which separates the liquid containment region from the outlet, may have any suitable length such as, for example, at least 0.1 mm, at least 1 mm, at least 1 cm, at least 3 cm, at least 5 cm, or at least 10 cm. Microfluidic channel 1212 may be linear, serpentine, or have any other suitable shape. In some cases, a portion of microfluidic channel 1212 includes a meandering region that can be used a detection region, as described in more detail below.

Additionally, in some embodiments where an absorbent material is positioned in a liquid containment region that is separated from an outlet, e.g., as shown in the embodiment illustrated in FIG. 18B, the absorbent material is not in direct contact with an atmosphere external to the device. In some such embodiments, the absorbent material is not accessible via the outlet. This arrangement may, in some cases, reduce or prevent evaporation of a liquid from the absorbent material and/or reduce exposure of the liquid to a user. Sometimes, this arrangement can be combined with a means of fluid flow other than absorption such as application of positive pressure at an inlet, application of vacuum at an outlet, gravity, capillary forces, or combinations thereof. In certain embodiments, an external source such as application of a positive pressure or a vacuum can be used to control fluid flow, instead of forces that are inherent to a material and/or a dimension of a device (such as wicking and capillary forces). Thus, the absorbent material, in some such embodiments, is not used as a wick for controlling or modulating fluid flow in the device, as described in more detail below.

In other embodiments, however, fluid flow in the device may be controlled and/or modulated by wicking action by using the absorbent material as the main source of driving fluid flow. Control and/or modulation of fluid flow can be enhanced especially in embodiments where the absorbent material is contained in a liquid containment region having an outlet as part of the liquid containment region (e.g., where the absorbent material is in direct contact with an atmosphere external to the device via the outlet), since liquid can evaporate from the absorbent material, thereby enhancing the wicking action. In certain such embodiments, the absorbent material may extend beyond the microfluidic system, e.g., by protruding out of an outlet. Fluid flow in the device may also be controlled and/or modulated by wicking action without substantial evaporation by, for example, not letting the absorbent material extend beyond the microfluidic system but while using the absorbent material as the main source of driving fluid flow.

In some instances, liquid containment region 1206 is configured and arranged to contain, absorb or capture substantially all of the liquid in a device, thereby preventing any liquid from exiting the device. That is, substantially all of the liquid introduced and/or stored in a microfluidic system ends up in the liquid containment region after use of the device. This arrangement can reduce the chances of a user being exposed to and/or infected by a liquid contained in the device. In some such embodiments, the liquid containment region further includes a disinfectant material that neutralizes, reacts with, denatures, disinfects, and/or sterilizes a liquid, a component of the liquid, or a portion of a microfluidic system in contact with the liquid, as described in more detail below. Substantially all of the liquid may include, for example, greater than 95% of any liquid in the microfluidic system in one embodiment, or, in other embodiments, greater than 97%, greater than 99%, or greater than 99.9% of any liquid in the microfluidic system. Any remaining liquid that is not captured by the system may include, for example, minute portions of the liquid that may be associated with a binding reaction at a reaction site and/or any liquid remaining in a valve or other component positioned in the device (e.g., droplets or films of liquid left on a surface of the microfluidic channel).

While the liquid containment region may capture or absorb at least one liquid in a microfluidic system, in some cases the liquid containment region is configured so that any air or other gases flowing in the device is not captured by absorbent material 1208. This configuration can allow the air or other gases to escape through outlet 1224. In some embodiments, a detector 1226 is positioned between the liquid containment region and outlet 1224 to detect the presence of any liquids that have not been captured by absorbent material 1208. Such detection is described in more detail below.

Although much of the description herein relates to a liquid containment region being used as a waste area for capturing liquid waste in a microfluidic system, it should be understood that the liquid containment region may be positioned at any suitable position in a microfluidic system and that the invention is not limited in this respect. For instance, in other embodiments, a liquid containment region may be positioned at one or more of a reagent inlet area, a region storage area, a sample loading area, a reaction area, or at an outlet. The liquid containment region may be positioned on top of, underneath, or may be coplanar with one of the above regions (e.g., a reaction region). For example, a liquid containment region positioned at a sample loading area and/or at a reagent inlet area may be useful for storing liquid in the device after the liquid (e.g., a sample or reagent) is introduced into the device. In some embodiments, application of a positive pressure at the inlet or a reduced pressure at an outlet can cause the liquid contained in the liquid containment region to flow into other portions of the microfluidic system.

Figure 18C:
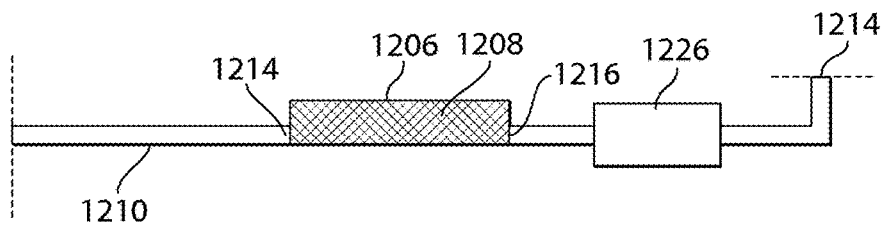
FIG. 18C is a schematic diagram showing a side view of the liquid containment region of FIG. 18B according to an embodiment of the invention.

FIG. 18C shows a side view of liquid containment region 1206. As shown in this illustrative embodiment, liquid containment region 1206 is in the form of a large reservoir; however, a liquid containment region may have any suitable configuration for containing, capturing, or absorbing one or more liquids in a device. For instance, in some embodiments, a liquid containment region is a portion of a microfluidic channel having an absorbent material associated therewith. In addition, liquid containment regions may have any suitable shape. For example, as viewed from above, a liquid containment region may be circular, curved, square, rectangular, triangular, oval, or irregularly shaped. Absorbent materials associated with the liquid containment region may have a shape similar to that of the liquid containment region or, in other embodiments, may have a shape different from that of the liquid containment region. For example, a liquid containment region may be square and an absorbent material positioned in the containment region may be circular. This arrangement can allow any fluids that are not absorbed by the absorbent material to flow around the absorbent material along the edges of the liquid containment region.

A liquid containment region may have any suitable dimensions. For instance, the liquid containment region may have a same height as that of an adjacent microfluidic channel, or, in other embodiments, may have a height that is smaller or greater than that of an adjacent microfluidic channel. For example, a ratio of an average height of a liquid containment region to an average height of an adjacent microfluidic channel may be, for example, greater than 1:20 in one embodiment, or greater than 1:10, 1:5, 1:2, 1:1, 2:1, 4:1, 6:1, 10:1, 20:1, 30:1, or 50:1 in other embodiments. The average height of the liquid containment region may be greater than 20 microns, or, in other embodiments, greater than 40 microns, 80 microns, 100 microns, 150 microns, 200 microns, 300 microns, 500 microns, 1 mm, 2 mm, or 5 mm.

The liquid containment region may also have any suitable volume for containing, absorbing, or capturing a liquid. The liquid containment region may have a volume of, for example, greater than 0.1 microliters, greater than 1 microliter, greater than 10 microliters, greater than 20 microliters, greater than 50 microliters, greater than 75 microliters, greater than 100 microliters, greater than 250 microliters, greater than 500 microliters, or greater than 1000 microliters.

The absorbent material may have essentially the same volume as that of the liquid containment region, or it may have a smaller volume than that of the containment region. For instance, the total volume occupied by the absorbent material prior to absorption of a liquid (and/or prior to first use of the device), including the volume occupied by any pores present in the material, may be less than 100% but greater than 20%, 40%, 60%, 80%, or 90% of the volume of the liquid containment region. Sometimes, the total volume of the absorbent material is less than 80%, 60%, 40%, 20%, or even 10% of the volume of the liquid containment region. Advantageously, in some embodiments involving an absorbent material having a volume less than the volume of the liquid containment region, certain fluids may flow through the absorbent material while other fluids can flow around the absorbent material. An absorbent material having a volume larger than that of the containment region is also possible.

In some cases, the volume of the liquid containment region and/or volume of the absorbent material is designed to be greater than the amount of liquid to be used with the device (e.g., stored, introduced, etc.). For instance, in some embodiments, the total volume of liquids introduced into the device, stored in the device, and/or flowing in the device is less than the volume of the liquid containment region. In some such embodiments, substantially all of the liquid introduced, stored, and/or flowed in the device can be absorbed in the liquid containment region. In another embodiment, the combined volume of the microfluidic channels, inlets, and other areas of the device besides the liquid containment region is less than the volume of the liquid containment region and/or the volume of the absorbent material.

A variety of absorbent materials may be used in devices described herein. The material and configuration of the absorbent material may depend, at least in part, on the fluid to be absorbed, compatibility with material(s) used to form the microfluidic system, configuration of the liquid containment region, or other factors. The absorbent material may be, for example, a solid material, a porous material, or in the form of particles, a powder, or a gel. In certain embodiments, the absorbent material is dried such as a piece of fabric, cellulose (e.g., paper), cotton, or the like. The absorbent material may include a polymer such poly(dimethylsiloxane), polypropylene, polyacrylamide, agarose, polyvinylidene fluoride, ethylene-vinyl acetate, styrenes, polytetrafluoro ethylene, polysulfones, polycarbonates, and dextran. In certain embodiments, the absorbent material is in the form of a single layer of material, multiple layers of materials, particles, beads, a coating, or a film. The absorbent material may be hydrophilic, hydrophobic, or a combination thereof.

In one embodiment, the absorbent material is pre-shaped prior to being associated with the liquid containment region; for instance, the material may be cut into a shape compatible with the liquid containment region. In another embodiment, the absorbent material takes on its shape after being associated with liquid containment region. In one particular embodiment, the absorbent material is in a first form prior to being associated with the liquid containment region and in a second form after being associated with the liquid containment region. For example, a gel precursor in fluid form may be flowed into a liquid containment region, where it forms a gel while positioned in the liquid containment region. In some cases, the absorbent material is sealed between walls of the liquid containment region. The absorbent material may be contained in the liquid containment region prior to use of the device, or, in other embodiments, during use of the device. Depending on the material, the absorbent material may be in dry form prior to use of the device.

Figure 19A:
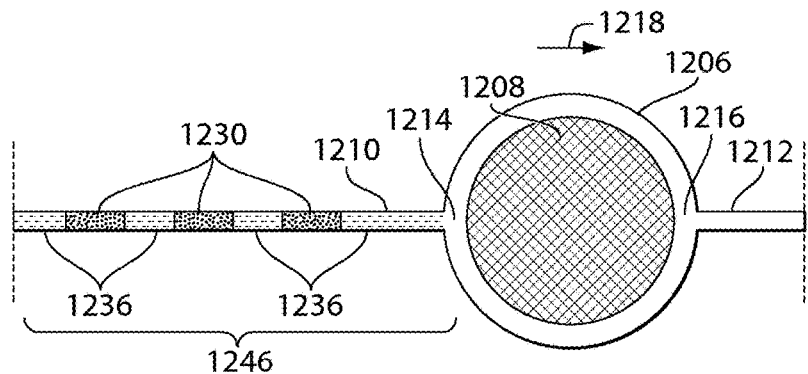
FIGS. 19A-19C show the progression of absorption of a liquid in a liquid containment region of a microfluidic system according to an embodiment of the invention.
Figure 19B:
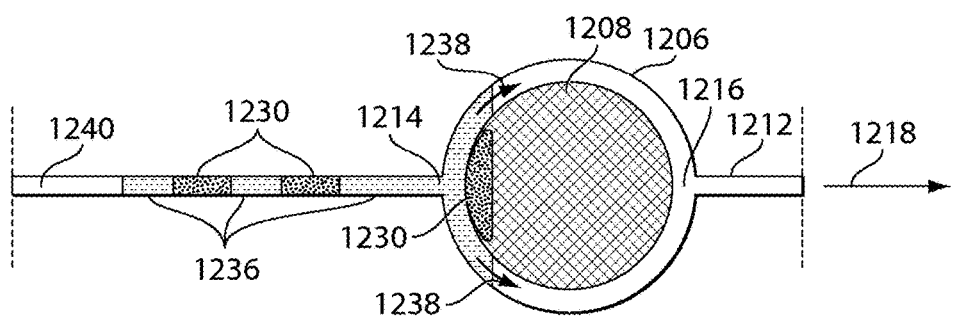
Figure 19C:
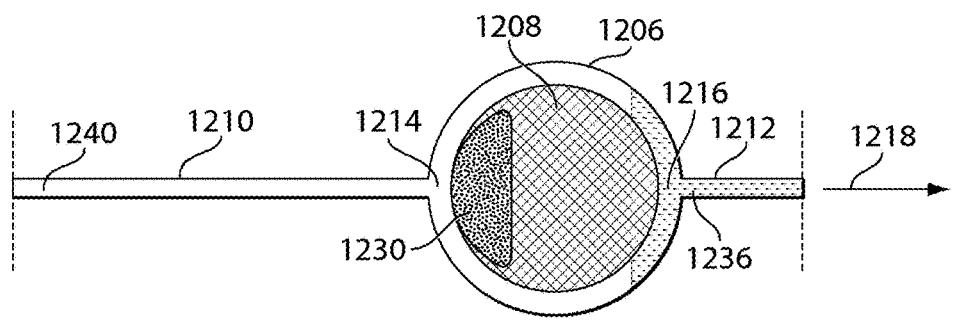

FIGS. 19A-19C show the use of a liquid containment region with immiscible liquids according to another embodiment of the invention. As shown in the embodiment illustrated in FIG. 19A, liquid containment region 1206 includes an absorbent material 1208, which may be configured to absorb at least one liquid in a fluid stream comprising the liquid and an immiscible fluid. In one particular embodiment, the fluid stream includes aqueous fluids in the forms of plugs 1230 separated from each other by immiscible plugs of fluid 1236. As a fluid stream flows in the direction of arrow 1218 into channel 1210, aqueous plugs 1230 maintain their separation from one another. Accordingly, flow of a first fluid immiscible with a second fluid is established. As the fluid stream enters liquid containment region 1206 via opening 1214, however, the aqueous plugs are absorbed by absorbent material 1208, which is in the form of a hydrophilic absorbent material (FIG. 19B). Immiscible fluids 1236, which may be in the form of a gas or a hydrophobic liquid, are not absorbed by absorbent material 1208. These immiscible fluids can travel around the side portions of the absorbent material in the direction of arrows 1238 and may exit the liquid containment region via opening 1216. Additionally and/or alternatively, the immiscible fluids may travel around the top and/or bottom portions of the absorbent material as viewed from a cross-section. In other embodiments, immiscible fluid 1236 may travel through absorbent material 1208, optionally exiting the liquid containment region at opening 1216. For instance, immiscible fluid 1236 may be in the form of a gas that can pass through the pores of the absorbent material. An outlet may be positioned downstream of channel 1212 and the immiscible fluids may exit the device, while the liquid reagents are captured in the liquid containment region.

In some instances, immiscible fluid 1236 is in the form of a gas and substantially all of aqueous liquid is absorbed in the liquid containment region. As shown in the embodiment illustrated in FIG. 19C, liquid containment region 1206 and absorbent material 1208 may be designed to absorb substantially all of the liquid in the device without saturating the absorbent material with the liquid. This may be achieved, in one embodiment, by designing the liquid containment region and/or absorbent material to have a volume larger than the total volume of liquids to be used with the device. This configuration can reduce the probability of any liquid exiting the device. After all of the liquid is absorbed, channel 1210 may be empty and may contain air 1240.

In another embodiment, a liquid containment region such as the one shown in FIGS. 19A-19C is positioned at or near a reagent storage area. For instance, in one particular embodiment, area 1246 of FIG. 19A is in the form of a reagent storage area. Reagents that are stored in the reagent storage area may be required to pass through the liquid containment region in order to reach a reaction area positioned downstream of the liquid containment region. In some cases, the reagent storage area includes stored aqueous reagents in the form of plugs separated from each other by an immiscible fluid such as a gas or a hydrophobic liquid. As mentioned above, these immiscible fluids can prevent the plugs of aqueous reagent from interacting with each other during storage and/or upon being introduced into the microfluidic system. However, later during use, it may be desirable to remove the immiscible fluids from the channel to allow interaction between the aqueous liquids. In one such embodiment, a stream of fluid comprising aqueous liquids in the form of plugs separated by a hydrophobic liquid is flowed through a liquid containment region. Unlike the embodiment described above where the absorbent material 1208 is a hydrophilic absorbent material, the absorbent material in this case may be a hydrophobic absorbent material. The hydrophobic material may absorb only the hydrophobic liquid, allowing the aqueous liquids to pass through. In some cases, the aqueous liquids mix with one another while passing through the absorbent material. The liquid reagents can then proceed to a reaction area or to another area of the device.

Figure 20A:
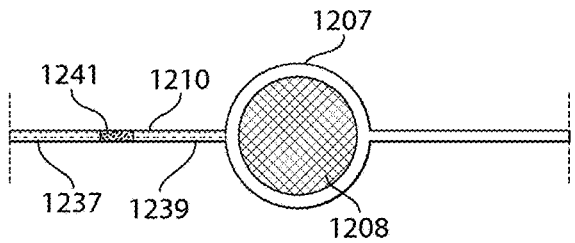
FIGS. 20A-20E show a method of absorbing a fluid and, in some embodiments, mixing fluids, according to an embodiment of the invention.
Figure 20B:
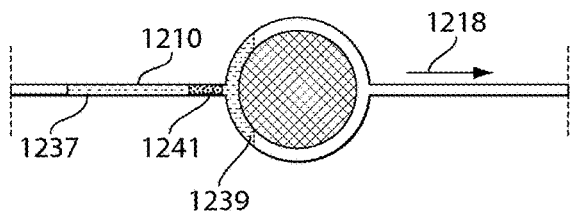
Figure 20C:
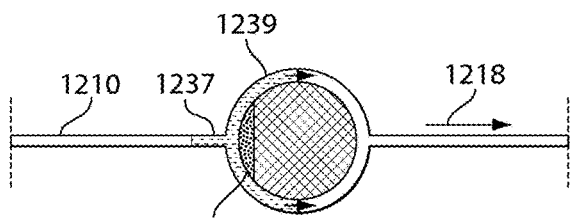
Figure 20D:
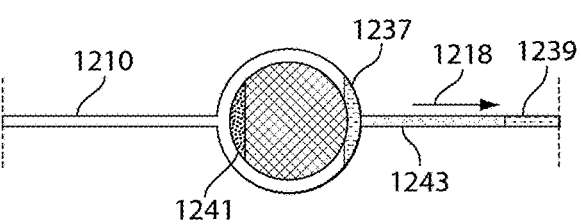
Figure 20E:
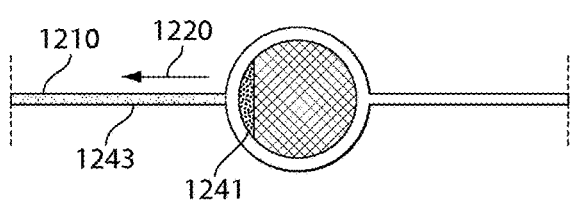

As shown in the embodiments illustrated in FIGS. 20A-20E, in some cases a first fluid 1237 and a second fluid 1239 are stored in a microfluidic channel 1210, e.g., on both sides of a plug of fluid 1241 immiscible with the first and second fluids. After flowing the sequence of fluids in the direction of arrow 1218 through a fluidic structure 1207 containing an absorbent material 1208 (FIGS. 20A-20C), immiscible fluid 1241 can be retained by the absorbing material, allowing the first and second fluids to mix with each other to form a mixture 1243 (FIG. 20D). Mixture 1243 may be, for example, an activated (or reactive) mixture, which can be used upstream or downstream of the structure containing the absorbent material. In some cases, the first and second fluids may be aqueous solutions and the immiscible fluid may be a hydrophobic liquid or a gas. For instance, in one embodiment, the first fluid is a solution containing hydroquinone and the second fluid is a solution containing silver salts. In another embodiment, the first fluid is a solution containing a substrate and the second fluid is a solution containing an enzyme specific for the substrate. The immiscible fluid may be a hydrophobic liquid that is absorbed by a hydrophobic absorbent material. Optionally, mixing between the first and second fluids can be facilitated by flowing the fluids backwards into fluidic structure 1207 (FIG. 20E) in the direction of arrow 1220. Because the dimensions of fluidic structure 1207 may be larger than that of channel 1210, the limitation in mixing usually found in microchannels due to laminar flow may be alleviated (e.g., chaotic mixing may occur while the fluids travel backwards in the fluidic structure).

Figure 21A:
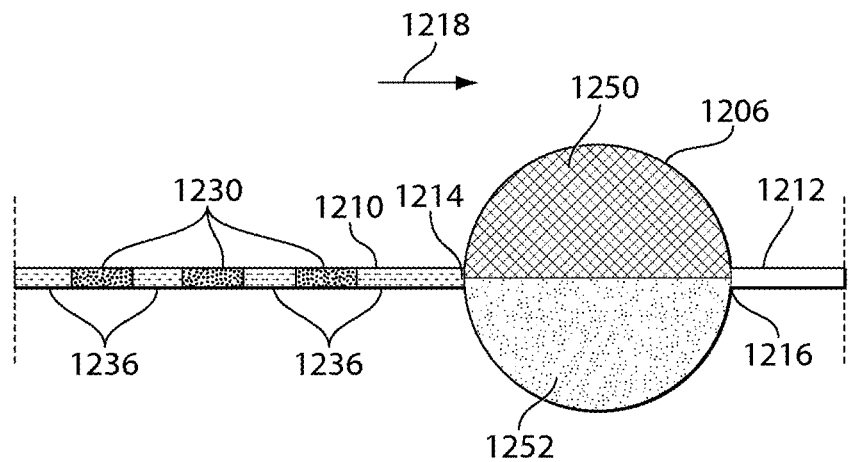
FIGS. 21A-21B show a progression of absorption of two different liquids in a liquid containment region according to an embodiment of the invention.
Figure 21B:
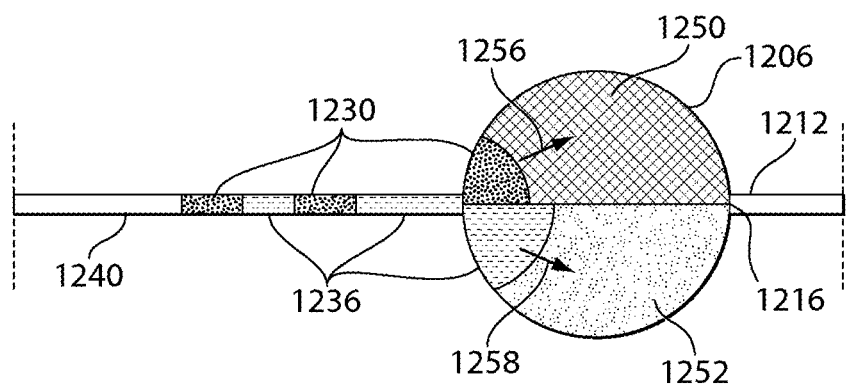

In some embodiments, a liquid containment region can include more than one types of absorbent material contained therein. For example, in the embodiments illustrated in FIGS. 21A and 21B, liquid containment region 1206 includes a first absorbent material 1250, which may absorb hydrophilic liquids, positioned adjacent a second absorbent material 1252, which may absorb hydrophobic liquids. Upon the flow of aqueous reagents in the form of plugs 1230 separated by immiscible fluid 1236 (e.g., a hydrophobic liquid or a gas) into the liquid containment region, the aqueous liquids can be absorbed by absorbent material 1250. If immiscible fluid 1236 is a hydrophobic liquid, these liquids can be absorbed by absorbent material 1252, e.g., as shown in FIG. 21B. Absorption of the aqueous liquid extends in the direction of arrow 1256 and absorption of the hydrophobic liquid extends in the direction of arrow 1258. The liquids may remain in the liquid containment region while any gases contained in the microfluidic system may pass through or around the absorbent materials, the gases exiting the liquid containment region at opening 1216.

Figure 22A:
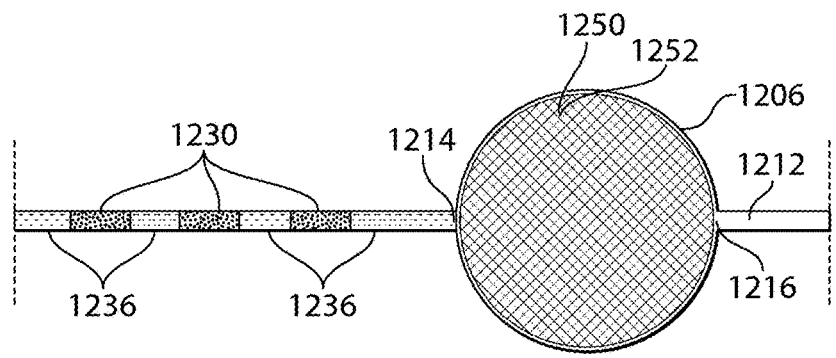
FIG. 22A is a schematic diagram showing a top view of a liquid containment region including two different types of stacked absorbent materials according to an embodiment of the invention.
Figure 22B:
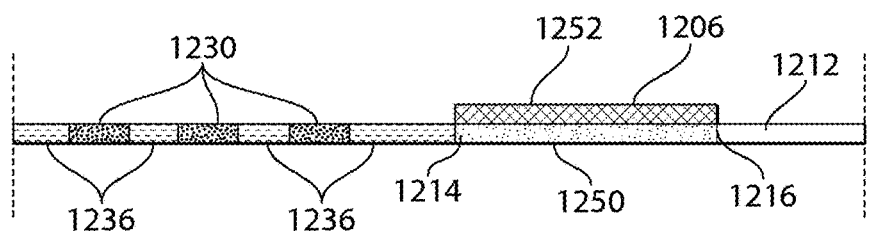
FIG. 22B shows a side view of the liquid containment region shown in FIG. 22A according to an embodiment of the invention.
Figure 22C:
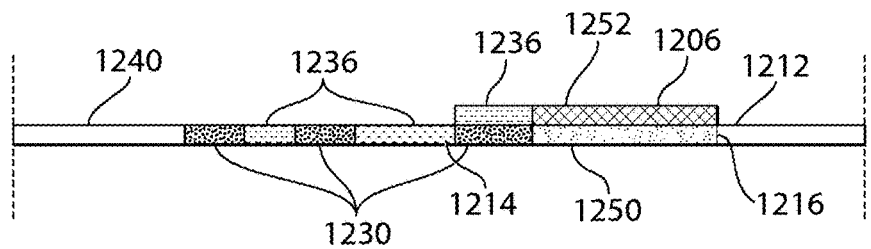
FIG. 22C shows absorption of two different types of liquids in the liquid containment region shown in FIGS. 22A and 22B according to an embodiment of the invention.

In other embodiments, a liquid containment region may include two or more types of absorbent material positioned on top of one another within the containment region. For instance, as shown in the embodiments illustrated in FIGS. 22A-22C, a first absorbent material 1250, e.g., a hydrophilic absorbent material, and a second absorbent material 1252, e.g., a hydrophobic absorbent material, are positioned on top of one another in liquid containment region 1206. Accordingly, as shown in FIG. 22C, aqueous reagents (e.g., in the form of plugs 1230) can be absorbed near or at the bottom of the liquid containment region and hydrophobic liquids cab be absorbed near or at the top of the region. Of course, in other embodiments, absorbent materials can be positioned in other configurations relative to one another. For example, in some cases, alternating first and second absorbent materials may be stacked on top of one another or beside one another. In other cases, first and second absorbent materials may be interwoven, intertwined, or mixed with one another in a liquid containment region.

Figure 23A:
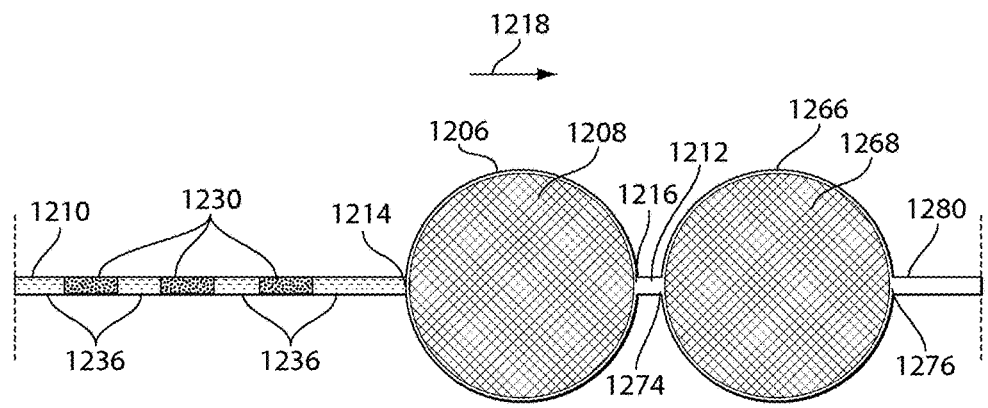
FIGS. 23A-23C show a progression of absorption of fluids in a microfluidic system comprising multiple liquid containment regions according to an embodiment of the invention.
Figure 23B:
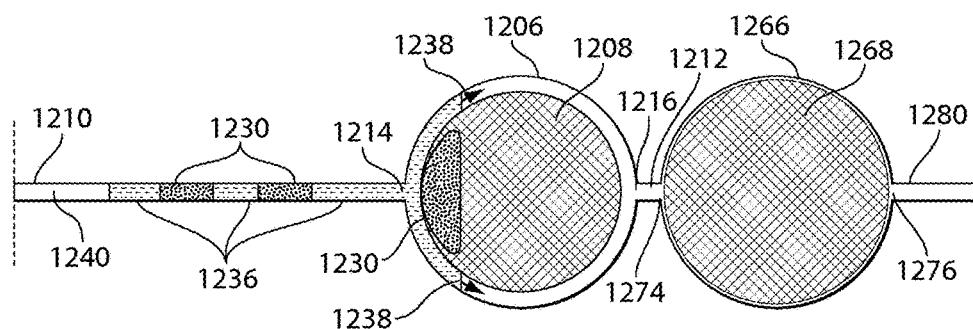
Figure 23C:
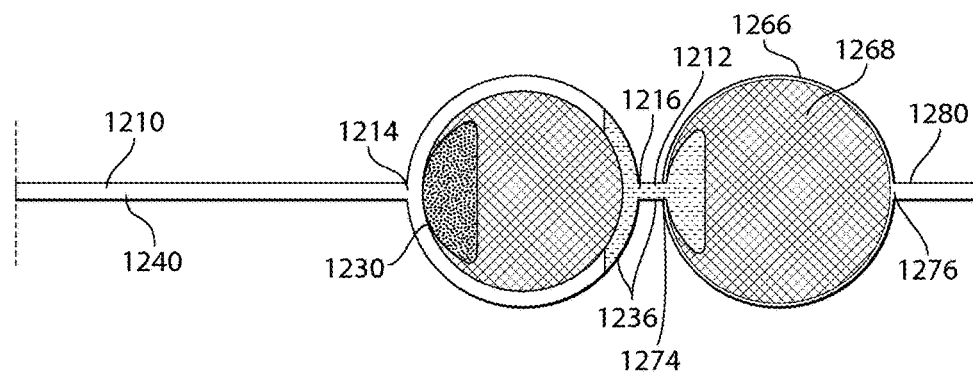

As shown in the embodiments illustrated in FIGS. 23A-23C microfluidic systems described herein may include multiple liquid containment regions. In some cases, the liquid containment regions are positioned adjacent one another. Multiple liquid containment regions (e.g., 2, 3, 4, 5, etc. containment regions) may be connected in series and/or in parallel. The multiple liquid containment regions may contain the same absorbent material or may include different absorbent materials that absorb different liquids, for example. As illustrated in FIG. 23A, first liquid containment region 1206 includes first absorbent material 1208, and second liquid containment region 1266 contains second absorbent material 1268. The liquid containment regions are in fluid communication with one another via channel 1212. In one particular embodiment, first absorbent material 1208 absorbs an aqueous liquid and second absorbent material 1268 absorbs a hydrophobic liquid. Aqueous liquids may be in the form of plugs 1230, each of which are separated from one another by an immiscible fluid 1236 (e.g., a hydrophobic liquid). Upon flowing in the direction of arrow 1218 and entering the first liquid containment region via opening 1214, the hydrophobic liquid is not absorbed by first absorbent material 1208, but instead flows around the absorbent material in the direction of arrows 1238. The aqueous liquids, however, are absorbed by absorbent material 1208. As illustrated in FIG. 23C, the aqueous liquids remain in the first liquid containment region while the hydrophobic liquids exit the first liquid containment region via opening 1216, flowing through channel 1212 to the second liquid containment region. The hydrophobic liquid is absorbed by the second absorbent material 1268, which may be hydrophobic in nature. In some such embodiments, the liquid containment region and absorbent material(s) contained therein may be configured to absorb substantially all of the liquids in the device. Accordingly, essentially none of the liquids in the device exit the device during or after use, in some embodiments.

As described herein, fluids may be flowed in a microfluidic system by any suitable method such as by applying a positive pressure at an inlet (e.g., by using a plunger, gravity, and/or a pump), gravity, capillary action, applying a vacuum source to an outlet of the device, and combinations thereof. Optionally, flow of fluids may be controlled by methods described in U.S. Patent Application Ser. No. 61/047,923, filed Apr. 25, 2008 and entitled "Flow Control in Microfluidic Systems", which is incorporated herein by reference in its entirety. In some embodiments, the flow rate of a liquid flowing in the microfluidic system is controlled by one or more of the methods described above, and the act of absorbing a liquid by an absorbent material associated with a liquid containment region does not substantially modulate the flow rate. In certain embodiments, the act of absorbing does not substantially modulate the flow rate of a liquid flowing at a region positioned upstream or downstream of the liquid containment region and/or at a region positioned outside of a reaction area. The act of absorbing does not substantially modulate the flow rate of a fluid if, for example, the rate of flow of the fluid is constantly being controlled by a source other than absorption (e.g., pumping, gravity, capillary action, source of vacuum, etc.). If any absorption is present in the microfluidic system (e.g., in a liquid containment region), the resulting flow rate as provided by the source may be much greater than the rate of absorption. In certain embodiments, the flow rate as provided by a non-wicking source may be at least 10 times, at least 20 times, at least 50 times, at least 70 times, or at least 100 times greater than the flow rate provided by the wicking source, all else being equal. Therefore, even though absorption may take place in a microfluidic system, absorption does not substantially contribute to the rate of fluid flow. Accordingly, in some embodiments, the volumetric flow rate of a fluid in the microfluidic system is not substantially altered due to absorption. In certain such embodiments, because the flow rate of the fluid is not substantially modulated due to absorption, a liquid containment region and absorbent material associated therewith, if present, may be configured in a variety of configurations and arrangements without needing to account for the size and dimensions of the absorbent material. This method of operating the device affords flexibility in the design and use of the device.

Furthermore, in some embodiments, when a sequence of immiscible fluids (e.g., alternating plugs of aqueous reagents separated by a hydrophobic liquid, a fluorinated liquid, or a gas, for example) arrives at a liquid containment region, not all fluid is absorbed by the absorbent material. For instance, if the absorbent material is hydrophilic (e.g., made of hydrophilic filter paper), it will selectively absorb the aqueous reagents, and in some instances, may provide a contribution to flow actuation by wicking. (The contribution to flow actuation by wicking may be small compared to flow actuation by a non-wicking mechanism, as described above.) During the course of the operation of the device, however, the fluid arriving at the liquid containment region will be alternatively aqueous and non-aqueous. When the non-aqueous fluid arrives at the liquid containment region, it is not absorbed by the hydrophilic absorbent material and therefore does not contribute to flow actuation by wicking. Accordingly, the ability to use the absorbent properties of the liquid containment region to generate fluid flow are thus limited to actuating fluid of one kind (e.g., an aqueous reagent), and wicking mechanisms will be inactive in driving fluid flow of the other fluids (e.g., the non-aqueous fluids). In this context, an alternative source of flow control (e.g., a source of flow actuation other than by wicking) may be necessary for the proper operation of the device.

As mentioned, in some embodiments, the rate of flow of a liquid in a microfluidic system described herein is controlled by a method other than absorption (e.g., other than wicking by an absorbent material). In some such embodiments, a liquid containment region may be positioned outside of a reaction area. In some instances, the liquid containment region is positioned downstream of the reaction area (e.g., near an outlet of the device), and the rate of flow of a liquid in the device is controlled by methods described herein. In one particular embodiment, the flow rate is controlled by applying a vacuum source to an outlet of the device. A method of using the device may include, for example, contacting the liquid with the reaction area of the microfluidic system, absorbing at least a portion of the liquid with an absorbent material contained in the liquid containment region, and controlling a rate of flow of the liquid. In certain such embodiments, the act of absorbing does not substantially modulate the flow rate of a liquid flowing upstream of the liquid containment region. For instance, as a first liquid portion is being absorbed by an absorbent material in the liquid containment region, a second liquid portion flowing upstream of the liquid containment region (or downstream of the liquid containment region, in other embodiments) flows at the same rate after absorption of the first liquid portion as before absorption of the first liquid portion. The first and/or second liquid portions may be a continuous stream of liquid, or may be in the form of liquid plugs. By not allowing the flow rate of a liquid in the microfluidic system to be modulated by the act of absorption, the flow rate can be controlled accurately by a single external source (e.g., a pump or a source of vacuum). This control is especially useful for performing timed processes within the microfluidic device, such as flowing a particular amount of reagent over a reaction area for a specified period of time.

In one particular embodiment, a series of reaction/binding and washing steps are combined with absorption of a liquid in a liquid containment region, wherein the act of absorbing does not substantially modulate flow rate. For example, a method may comprise establishing flow of a first liquid in a device comprising a microfluidic network including at least one microfluidic channel, and causing a chemical and/or biological reaction between a first component contained in the first liquid and a second component immobilized in the reaction area in fluid communication with the microfluidic channel. Next, a wash solution may be passed across the reaction area. All or a portion of the first liquid and/or the wash solution may be absorbed with an absorbent material contained in a liquid containment region, which may be positioned outside (e.g., downstream) of the reaction area. In some such embodiments, the rate of flow of one or more liquids in the device may be controlled by a method other than absorption such that the act of absorbing does not substantially modulate the flow rate of a liquid flowing upstream of the liquid containment region. Control of the flow rate may be performed, for example, using a pump or other component providing a positive pressure at an inlet of the device, by a source of vacuum positioned at an outlet of the device, and/or by other methods.

As mentioned, a disinfectant may be associated with a liquid containment region, and optionally with an absorbent material contained therein, in some embodiments. A disinfectant may be used to neutralize, react with, denature, disinfect, and/or sterilize components such as microorganisms, cells, proteins, chemical compounds, or a portion of a microfluidic system containing such components. A variety of disinfectants may be used, which may depend, at least in part, on the particular types of reagents and samples to be used with the device. Other factors that may be used in determining an appropriate disinfectant include, for example, it's compatibility with an absorbent material (if present), it's compatibility with material(s) used to form the microfluidic system, any components that may be integrated with the system, and potential toxicity to the user (e.g., in case the disinfectant leaks out of the system).

Disinfectants can be in any suitable form such as a solid, powder, liquid, gel, or the like. For instance, a liquid disinfectant may be associated with an absorbent material in the form of a gel, and a dried disinfectant may be associated with a dried absorbent material. Of course, other combinations of disinfectants and absorbent materials are possible. Disinfectants may be associated with all or only portions of an absorbent material and/or of a liquid containment region.

Non-limiting examples of disinfectants include alcohols (e.g., ethanol and isopropanol), aldehydes (e.g., glutaraldehyde), halogens (e.g., chloramine, chlorine, hypochlorites (e.g., bleach), and iodine), oxidizing agents (e.g., chlorine dioxide, hydrogen peroxide, ozone, peracetic acid, potassium permanganate, and potassium peroxymonosulfate), phenolics (e.g., phenol, O-phenylphenol, chloroxylenol, hexachlorphene, and thymol), quaternary ammonium compounds (e.g., benzalkonium chloride), acids, bases, and salts.

In one embodiment, additives such as complexing agents, weak acids, weak bases weak oxidizers and weak reducers can be added to the liquid containment region (e.g., a waste containment region) to inactivate toxic chemicals (e.g., heavy metals, oxidizing or reducing species, acidic or alkaline species, azides, cyanides or the like) that may otherwise be exposed to the user and/or to the environment. Such embodiments may improve the safe use of the device.

Accordingly, a device described herein may include, in one embodiment, a first microfluidic channel, a reaction area in fluid communication with the first microfluidic channel, and a disinfectant stored in a liquid containment region prior to use of the device (optionally, in association with an absorbent material). In some cases, the liquid containment region is positioned downstream of the reaction area and in fluid communication with the reaction area during use of the device. The device may further comprise a second microfluidic channel containing a second reagent disposed therein prior to use of the device. In some embodiments, the first and second microfluidic channels are in fluid communication with one another prior to use of the device; however, in other embodiments, the first and second microfluidic channels are not in fluid communication with one another prior to use of the device. In some such embodiments, during use of the device, the first and second microfluidic channels may be brought into fluid communication with one another by using, for example, a fluid connector. In some cases, the liquid containment region is not positioned in a reaction area, but is positioned upstream and/or downstream from the reaction area. For instance, in one particular embodiment, the liquid containment region is used as a waste area.

Optionally, a liquid containment region may be associated with one or more components such as a detector, valve, membrane, pump, filter, or the like. Such components may be positioned at an opening of a liquid containment region, within the containment region, above or below the containment region, adjacent a liquid containment region, or at any other suitable position. In some cases, such a component is positioned downstream of a liquid containment region.

In some embodiments, a liquid containment region is associated with a detector that can detect the presence or absence of a fluid in the liquid containment region and/or in a region adjacent a liquid containment region. For example, as shown in embodiment illustrated in FIGS. 24A and 24B, microfluidic system 1300 includes a liquid containment region 1306 containing an absorbent material 1308. The system also includes a detector 1312 positioned adjacent detection area 1316 of microfluidic channel 1320. In some cases, a portion of microfluidic channel 1320 includes one or more meandering regions that can be aligned with the detector and used a detection region. The detector may include, for example, a light source 1312-A and a reader 1312-B, or any other suitable configuration. As shown in this illustrative embodiment, the detector is positioned between the liquid containment region and area 1324 of the device. In some embodiments, area 1324 is an outlet of a device; however, in other embodiments area 1324 may be a second containment region, a storage area, a reaction area, or the like.

Detector 1312 may be used to detect the presence of any liquid, or a particular type of liquid, present in microfluidic channel 1320. For instance, in one embodiment, the detector detects any liquids that flow out of the liquid containment region. This arrangement may be useful, for example, for devices designed to trap a liquid within a liquid containment region. Such devices may be used, for example, in applications involving toxic, infectious, or other potentially harmful materials where it is desirable to prevent exposure of the materials to a user. In these and other embodiments, upon detection of a liquid or a particular type of liquid in detection area 1316, a signal may be sent to a control system (not shown), which can shut down or modulate a source of fluid flow in the system (e.g., a source of vacuum or a pump), thereby preventing the liquid from exiting the device.

Figure 24A:
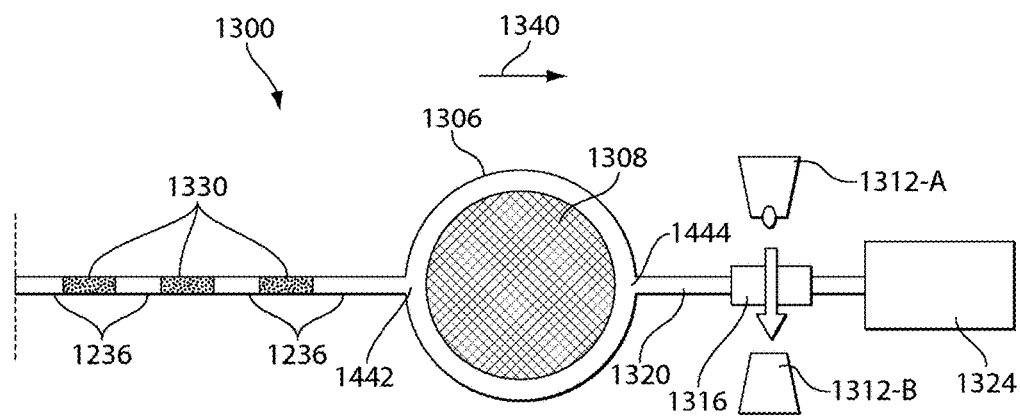
FIGS. 24A-24B are schematic diagrams showing detection of a fluid that has exited a liquid containment region according to an embodiment of the invention.
Figure 24B:
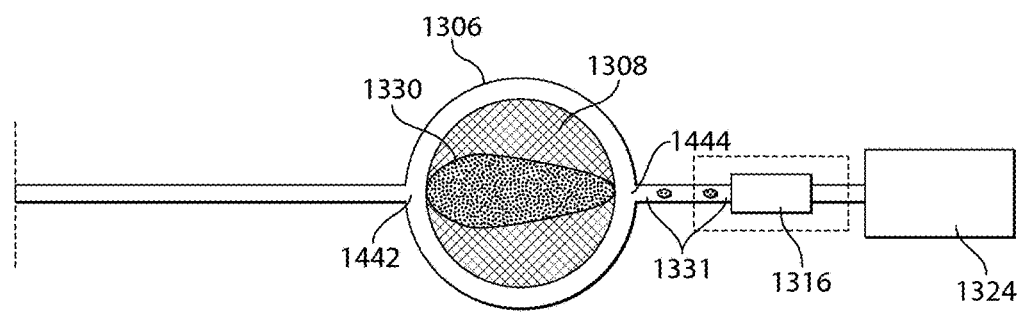

As shown in the embodiment illustrated in FIG. 24A, a microfluidic channel 1328 positioned upstream of liquid containment region 1306 contains liquid reagents 1330 separated from one another by an immiscible fluid 1332 (e.g., a gas). Upon flow of the reagents in the direction of arrow 1340, the liquid reagents enter the liquid containment region via opening 1442 and are absorbed in the liquid containment region (FIG. 24B). In one embodiment, the immiscible fluid is not absorbed by the absorbent material and exits the liquid containment region via opening 1444; however, in other embodiments, the immiscible fluid may be absorbed by the absorbent material. In some cases, portions 1331 of the liquid reagents exit the liquid containment region via opening 1444. As the portions reach detection area 1316, detector 1312 can detect the presence and/or identity of the liquids. It should be understood that any suitable detector can be used for determining a fluid. In some embodiments, the arrangements described in connection with FIGS. 16 and/or 17 can be associated with a liquid containment region.

Though in some embodiments, systems of the invention may be microfluidic, in certain embodiments, the invention is not limited to microfluidic systems and may relate to other types of fluidic systems. "Microfluidic," as used herein, refers to a device, apparatus or system including at least one fluid channel having a cross-sectional dimension of less than 1 mm, and a ratio of length to largest cross-sectional dimension of at least 3:1. A "microfluidic channel," as used herein, is a channel meeting these criteria.

The "cross-sectional dimension" (e.g., a diameter) of the channel is measured perpendicular to the direction of fluid flow. Most fluid channels in components of the invention have maximum cross-sectional dimensions less than 2 mm, and in some cases, less than 1 mm. In one set of embodiments, all fluid channels containing embodiments of the invention are microfluidic or have a largest cross sectional dimension of no more than 2 mm or 1 mm. In another set of embodiments, the maximum cross-sectional dimension of the channel(s) containing embodiments of the invention are less than 750 microns, less than 500 microns, less than 200 microns, less than 100 microns, less than 50 microns, or less than 25 microns. In some cases the dimensions of the channel may be chosen such that fluid is able to freely flow through the article or substrate. The dimensions of the channel may also be chosen, for example, to allow a certain volumetric or linear flowrate of fluid in the channel. Of course, the number of channels and the shape of the channels can be varied by any method known to those of ordinary skill in the art. In some cases, more than one channel or capillary may be used.

A "channel," as used herein, means a feature on or in an article (substrate) that at least partially directs the flow of a fluid. The channel can have any cross-sectional shape (circular, oval, triangular, irregular, square or rectangular, trapezoidal, or the like) and can be covered or uncovered. In embodiments where it is completely covered, at least one portion of the channel can have a cross-section that is completely enclosed, or the entire channel may be completely enclosed along its entire length with the exception of its inlet(s) and outlet(s). A channel may also have an aspect ratio (length to average cross sectional dimension) of at least 2:1, more typically at least 3:1, 5:1, or 10:1 or more. An open channel generally will include characteristics that facilitate control over fluid transport, e.g., structural characteristics (an elongated indentation) and/or physical or chemical characteristics (hydrophobicity vs. hydrophilicity) or other characteristics that can exert a force (e.g., a containing force) on a fluid. The fluid within the channel may partially or completely fill the channel. In some cases where an open channel is used, the fluid may be held within the channel, for example, using surface tension (e.g., a concave or convex meniscus).

A microfluidic substrate can be fabricated of any material suitable for forming a microchannel. Non-limiting examples of materials include polymers (e.g., polyethylene, polystyrene, polycarbonate, poly(dimethylsiloxane), and a cyclo-olefin copolymer (COC)), glass, quartz, and silicon. Those of ordinary skill in the art can readily select a suitable material based upon e.g., its rigidity, its inertness to (e.g., freedom from degradation by) a fluid to be passed through it, its robustness at a temperature at which a particular device is to be used, and/or its transparency/opacity to light (e.g., in the ultraviolet and visible regions). In some embodiments, the material and dimensions (e.g., thickness) of a substrate are chosen such that the substrate is substantially impermeable to water vapor.

In some instances, an microfluidic substrate is comprised of a combination of two or more materials, such as the ones listed above. For instance, the channels of the device may be formed in a first material (e.g., poly(dimethylsiloxane)), and a cover that is formed in a second material (e.g., polystyrene) may be used to seal the channels. In another embodiment, a channels of the device may be formed in polystyrene or other polymers (e.g., by injection molding) and a biocompatible tape may be used to seal the channels. A variety of methods can be used to seal a microfluidic channel or portions of a channel, including but not limited to, the use of adhesives, gluing, bonding, lamination of materials, or by mechanical methods (e.g., clamping).

A microfluidic system described herein may have any suitable volume for carrying out a chemical and/or biological reaction or other process. The entire volume of a microfluidic system includes, for example, any reagent storage areas, reaction areas, liquid containment regions, waste areas, as well as any fluid connectors, and microfluidic channels associated therewith. In some embodiments, small amounts of reagents and samples are used and the entire volume of the microfluidic system is, for example, less than 10 milliliters, less than 5 milliliters, less than 1 milliliter, less than 500 microliters, less than 250 microliters, less than 100 microliters, less than 50 microliters, less than 25 microliters, less than 10 microliters, less than 5 microliters, or less than 1 microliter. In other embodiments, relatively larger amounts of reagents and/or samples may be used and the entire volume of the microfluidic system is, for example, greater than 1 microliter, greater than 5 microliters, greater than 10 microliters, greater than 25 microliters, greater than 50 microliters, greater than 100 microliters, greater than 250 microliters, greater than 500 microliters, greater than 1 milliliter, greater than 5 milliliters, or greater than 10 milliliters.

The following examples are intended to illustrate certain embodiments of the present invention, but are not to be construed as limiting and do not exemplify the full scope of the invention.

Example 1

Fabrication of Microfluidic Channels in a Substrate

A method for fabricating a microfluidic channel system is described.

The layouts of the channel system were designed with a computer-aided design (CAD) program and are illustrated in FIGS. 3 and 4. The microfluidic devices were formed in poly(dimethylsiloxane) Sylgard 184 (PDMS, Dow Corning, Distrelec, Switzerland) by rapid prototyping using masters made in SU8 photoresist (MicroChem, Newton, Mass.). The masters were produced on a silicon wafer and were used to replicate the negative pattern in PDMS. The masters contained two levels of SU8, one level with a thickness (height) of ~50 μm defining the channels in the immunoassay area, and a second thickness (height) of ~250 μm defining the reagent storage and waste areas. The master was silanized with (tridecafluoro-1,1,2,2-tetrahydrooctyl)trichlorosilane (ABC-R, Germany). PDMS was mixed according to the manufacturer's instructions and poured onto the master.

After polymerization (4 hours, 65°), the PDMS replica was peeled off the master and access ports were punched out of the PDMS using brass tubing with sharpened edges (1.5 mm in diameter). To complete the fluidic network, a flat substrate such as a glass slide, silicon wafer, polystyrene surface, flat slab of PDMS, or an adhesive tape was used as a cover and placed against the PDMS surface. The cover was held in place either by van der Waals forces, or fixed to the PDMS using an adhesive.

In other embodiments, the microfluidic channels were made in polystyrene by injection molding. This method is known to those of ordinary skill in the art.

Example 2

Storing Reagents in a Microfluidic System

This example describes a method for storing dry and liquid reagents in a microfluidic system.

Dry and wet reagents were stored in the microfluidic systems shown in FIGS. 3-5 and 14. To store dry reagents, drops of biomolecules were placed onto the detection zones of the substrate. After 30 min, the solution was removed and the surface of the substrate modified with proteins was rinsed with buffer. The surface was dried with compressed nitrogen for 20 s, and then the substrate was sealed against a cover. The cover was either a plate of polystyrene (in the case PDMS substrates) (NUNC Omnitray, VWR, Switzerland) or a biocompatible adhesive (in the case of polystyrene substrates). When a biocompatible adhesive was used, the polystyrene substrate was drilled to obtain access holes prior to application of the cover. In a different approach, the holes were formed in the thermoplastic during the injection molding process by using pillars inside the cavity of the injection molding machine. All of the microchannels, including those of the reagent storage and immunoassay areas, were filled with blocking buffer (Tween 20 and/or BSA in phosphate buffered saline (PBS)) to render the surfaces of the microfluidic channels hydrophilic and to block the surfaces to avoid non-specific adsorption of protein on the walls of the microchannels. The blocking solution was removed by suction and the device was dried at room temperature under vacuum.

To store wet reagents in the microfluidic system, reagent solutions for an immunoassay were first prepared in separate containers (e.g., wells of a 96-well plate, or centrifuge tubes). The reagents were sequentially aspirated as liquid plugs, followed by air spacers between successive liquid plugs, into secondary tubing (polyethylene with a inner diameter of 0.2 mm) with a manually operated syringe connected to the back of the tubing.

Reagents were stored in channels of a reagent storage area of the microfluidic system (fabricated by the method described in Example 1) by connecting an outlet port of the tubing into an inlet of the channel. The fluids flowed from the tubing to the channel by either capillary forces, applying a reduced pressure (e.g., a vacuum) to the outlet of the channel, or by applying positive pressure to the inlet of the tubing (using a syringe plunger). The reagents resided in the reagent storage area of the channel.

The inlets and outlets of the channels were then sealed by placing a biocompatible adhesive over the inlets and outlets. In the case of a polystyrene substrate, this second tape was applied onto the surface opposite of the surface modified with the cover. This sealing protected the stored reagents from degradation/denaturation due to atmospheric conditions.

The reagents were stored in the microfluidic channels for three months without degradation/denaturation, as tested by use of the reagents in quantitative immunoassays. This example shows that both dry and liquid reagents (including proteins) can be stored for extended periods of time in microfluidic channels.

Example 3

Performing an Immunoassay by Loading a Sample Using an Open-Ended Capillary Tube This example shows that an immunoassay can be performed by loading a sample using an open-ended capillary tube and using reagents stored on a microfluidic substrate.

The microfluidic system of FIG. 7 was fabricated using the method described in Example 1. This system included four sections: a reagent storage area, a sample loading area, an immunoassay area and a waste area. The reagent storage area was pre-filled with reagents required to perform an immunoassay for the detection of total human IgG in whole blood: antibody solutions, washing buffers and amplification reagents (either enzymatic substrates or silver amplification reagents) using the method described in Example 2. These reagents were presented as ready-to-use aqueous solutions loaded as a sequence of liquid plugs, separated from each other by air gaps.

A sample of blood from a donor was obtained and the sample was loaded into a capillary tube (e.g., as shown in FIG. 8A) by capillary forces (or, in other experiments, by aspirating the sample in the capillary tube using a negative pressure applied at the other end of the tube). The outlet of the capillary tube was fitted to the sample loading port of the substrate and the sample was introduced into the microfluidic system by moving the frit within the tube towards the end of the capillary tube with a plunger. Because the reagent inlet of the microfluidic substrate had been previously sealed, the flow of sample was automatically directed inside the microfluidic channel towards the outlet of the device, which was vented. The capillary was left in place, and the frit (now wetted with sample) acted as an air-tight seal.

After introducing the sample into the substrate, the seal over the inlet and outlet ports were removed. Application of vacuum at the outlet of the system resulted in the delivery of the sample and the reagents to the immunoassay area according to the sequence pre-defined by the order of reagents lined up inside the reagent storage area. All fluids exiting the immunoassay area were eventually trapped inside the waste area. After completion of the assay, a signal specific for the target analyte was observable in the immunoassay areas.

Example 4

Performing an Immunoassay by Loading a Sample Using a Fluidic Connector

This example shows that an immunoassay can be performed by loading a sample using a fluidic connector and using reagents stored on a microfluidic substrate.

The microfluidic system of FIG. 5 was fabricated using the method described in Example 1. Device 300 includes sections 302 containing wet stored reagents and section 350 containing stored dry reagents. Immunoassay area 360 was pre-fabricated with physisorbed molecules using the method described in Example 2. The immunoassay area included a first detection zone 362 patterned with Tween (using a solution of Tween in PBS), second and third detection zones 364 and 366 patterned with anti-human IgG (using a solution of anti-human IgG in PBS), and a fourth detection zone 368 included patterned human IgG (using a solution of human IgG in PBS).

Reagent storage area 304 was pre-filled (using the method described in Example 2) with reagents required to perform an immunoassay for the detection of total human IgG in whole blood. The reagents were filled in the form of a sequence of liquid plugs, each of the liquid plugs separated by gaseous spacers. The reagents in lower portion 306 of the reagent storage area were (in order of introduction into the immunoassay area): three buffer washes, one plug of anti-human IgG labeled with gold colloid, three buffer washes, and six water washes. Upper portion 305 of the reagent storage area contained solutions for electroless silver deposition used as the amplification solutions. These solutions included silver salt, stored in channel 308, and hydroquinone, stored in channel 309. These solutions were kept separate prior to use. In FIG. 5A, the inlet 354 and outlet 318, which had previously been sealed, were unsealed at this stage.

A sample of venous blood from a healthy donor was obtained and the sample was loaded into a fluidic connector by capillary forces (or, in other experiments, by aspirating the sample in the capillary tube using a negative pressure applied at the other end of the tube). The fluidic connector was filled with a known, predetermined volume of sample (15 μL) by choosing an appropriate length of the capillary (and knowing the internal volume of the capillary). (This volume of sample was enough to sustain sample incubation for 10 minutes after the source of vacuum was set at −15 kPa.) The fluidic connector was bent so that one end of the fluidic connector fit into an outlet 318 of the reagent storage area, and the other end fit into an inlet 354 leading to the immunoassay area (see FIG. 5B). The fluidic connector enabled fluidic connection between sections 302 and 350. In FIG. 5A, inlets 316 and 317 and outlet 356, which had previously been sealed, were unsealed at this stage.

Application of a source of vacuum 390 (−15 kPa) at outlet 356 of the system initiated the assay. The sample entered the immunoassay area, including detection zones 362, 364, 366, and 368 (FIG. 5C), followed by the stored reagents from section 302 (FIG. 5D). The stored regents from section 302 included several rinsing reagents (e.g., buffer), which washed away any residual, unbound sample in the reaction area (FIG. 5D), as well as antibody solutions and amplification reagents.

After completion of the assay, an optical signal (a grayish film of metallic silver) specific for the analyte of interest was observable in detection zones 364, 366, and 368 of the immunoassay area (FIG. 5E). Using the series of physisorbed biomolecules in the detection zones as described above, the following results were observed at the end of the assay: 1) no signal in the detection zone modified with Tween (a detergent known to prevent adhesion of proteins), as this detection zone acts as an internal negative reference (detection zone 362); 2) a concentration-dependant signal in the detection zones modified with anti-human IgG, reflecting the binding of human IgG from the sample (detection zones 364 and 366); and 3) a constant signal in the detection zone modified with human IgG, which acts as an internal positive reference (detection zone 368). These observations were expected.

As shown in FIG. 5F, after removal of the fluidic connector and the source of vacuum, the signal remained permanently bound in the immunoassay area of the device, and could be directly observed and used for data storage.

This example demonstrates that a microfluidic system having stored reagents contained therein, connected by a fluidic connector containing a sample, can be used to detect total human IgG in a sample of whole blood.

Example 5

Absorbing Liquids in a Liquid Containment Region

This example describes the fabrication and use of a microfluidic system including a liquid containment region in the form of a waste containment region for performing an immunoassay to detect total human IgG in whole blood. The assay described below is only one example among many possible formats of solid-phase assays, and can be extrapolated to other solid-phase assays that involve affinity reaction between proteins, other biomolecules (e.g., DNA, RNA, and carbohydrates) or non-naturally occurring molecules.

Figure 25A:
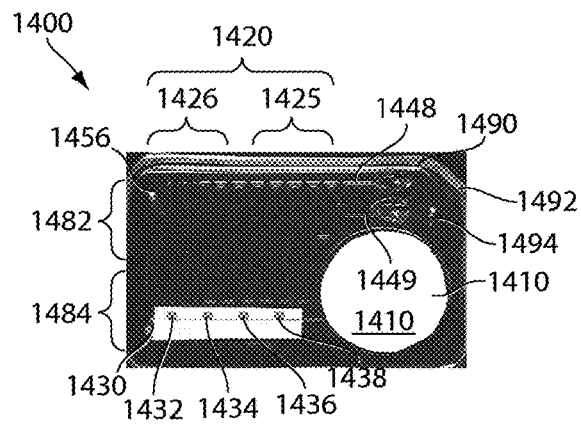
FIGS. 25A-25F are photographs of an experiment being performed in a microfluidic system including a liquid containment region used as a waste area according to an embodiment of the invention.

A microfluidic device was fabricated in PDMS using the materials and methods described in Example 1. Photographs of the device are shown in FIGS. 25A-25F. The design of the network of microchannels was similar to the design shown in FIGS. 4A-4C, except waste area 274 of FIG. 4A was in the form of a circular liquid containment region 1410, as shown in FIG. 25A. Liquid containment region 1410 was a circular cavity of 33 mm in diameter, having a depth of 350 microns.

Biomolecules were patterned onto the surface of a polystyrene dish (NUNC Omnitray, VWR, Switzerland) aligning with the detection zones of reaction area 1430. The reaction area included a first detection zone 1432 patterned with Tween (using a solution of Tween in PBS), second and third detection zones 1434 and 1436 patterned with anti-human IgG (using a solution of anti-human IgG in PBS), and a fourth detection zone 1438 included patterned human IgG (using a solution of human IgG in PBS).

Reagent storage area 1420 and reaction area 1430 were filled with a blocking buffer to render the surfaces of the areas hydrophilic and to avoid non-specific adsorption of protein on the walls of the areas. The blocking solution was removed by suction and the areas were dried at room temperature under vacuum.

A liquid-selective absorbent pad was obtained by cutting a 30 mm disc of filter paper (Waterman #1 (VWR, Switzerland)), which was positioned in the liquid containment region cavity. The PDMS was then sealed against the polystyrene substrate. In this configuration, the filter paper was encapsulated between the PDMS and polystyrene substrates.

In this example, detection in device 1400 was achieved by signal amplification based on silver enhancement. This choice was motivated to illustrate a scenario where two amplification reagents can be stored individually within the device, before being mixed in order to amplify the signal. (In other experiments, a similar assay was performed using the device shown in FIGS. 3A-3D, where amplification reagents were stored as an reagents in the sequence, and which did not require mixing. The amplification reagents used was the precipitating dye DAB.)

Reagent storage area 1420 was pre-filled (using the method described in Example 2) with reagents required to perform an immunoassay for the detection of total human IgG in whole blood based on silver enhancement. The reagents were filled in the form of a sequence of liquid plugs, each of the liquid plugs separated by gaseous spacers. The reagents in lower portion 1426 of the reagent storage area were (in order of introduction into the immunoassay area): three buffer washes, one plug of anti-human IgG labeled with gold colloid, three buffer washes, and six water washes. Upper portion 1425 of the reagent storage area contained solutions for electroless silver deposition used as the amplification solutions. These solutions included silver salt, stored in channel 1448, and hydroquinone, stored in channel 1449. These solutions were kept separate prior to use. In FIG. 25A, an inlet 1454 and an outlet 1456, which had previously been sealed, were unsealed at this stage.

A sample of venous blood from a healthy donor was collected in a heparinized tube, and the sample was loaded into a fluidic connector 1480 by capillary forces (or, in other experiments, by aspirating the sample in the capillary tube using a reduced pressure applied at the other end of the tube). The fluidic connector was filled with a known, pre-determined volume of sample (15 µL) by choosing an appropriate length of the capillary (and knowing the internal volume of the capillary). (This volume of sample was enough to sustain sample incubation for 10 minutes after the source of vacuum was set at −15 kPa.) The fluidic connector was bent so that one end of the fluidic connector fit into outlet 1456 of the reagent storage area, and the other end fit into inlet 1454 leading to the immunoassay area (see FIG. 25B). The fluidic connector enabled fluidic connection between sections 1482 and 1484 of the microfluidic system. In FIG. 25A, inlets 1490 and 1492 and outlet 1494, which had previously been sealed, were unsealed at this stage.

Figure 25D:
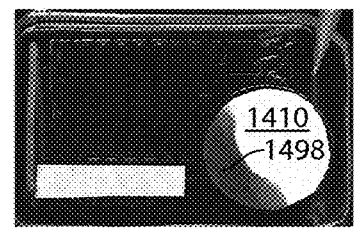
Figure 25B:
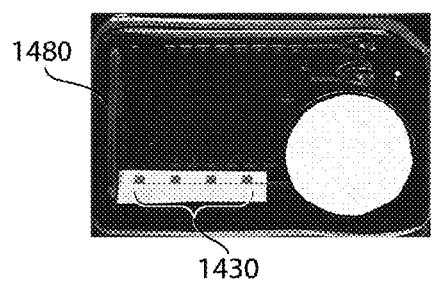

Application of a source of vacuum 1496 (−15 kPa) at outlet 1494 of the system initiated the assay. The sample entered the reaction area, including detection zones 1432, 1434, 1436, and 1438 (FIG. 25C), followed by the stored reagents from section 1482 (FIG. 25D). The stored regents from section 1482 included several rinsing reagents (e.g., buffer), which washed away any residual, unbound sample in the reaction area (FIG. 25D), as well as antibody solutions and amplification reagents.

As the reagents passed through the reaction area, they entered liquid containment region 1410 which was in the form of a waste area. The liquid containment region was positioned between reaction area 1430 and outlet 1494. As shown in FIG. 25C, liquid reagent 1498 (e.g., excess sample, stored reagents, and buffer) was absorbed by the absorbent material within the liquid containment region. The absorption increased as additional liquids entered the containment region (FIGS. 25C-25F). The gaseous spacers that separated the liquid reagents passed through the liquid containment region (and around the absorbent material), exiting at outlet 1494; however, no liquids were observed to exit the liquid containment region or the device.

Figure 25E:
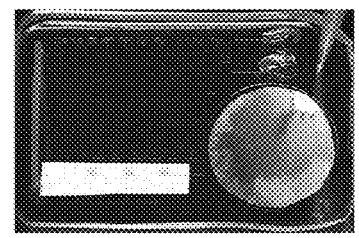
Figure 25C:
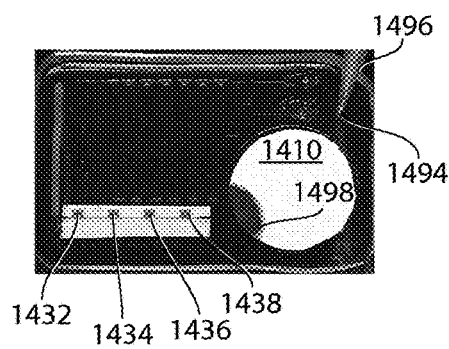

After completion of the assay, an optical signal (a grayish film of metallic silver) specific for the analyte of interest was observable in detection zones 1434, 1436, and 1438 of the reaction area (FIG. 25E). Using the series of physisorbed biomolecules in the detection zones as described above, the following results were observed at the end of the assay: 1) no signal in the detection zone modified with Tween (a detergent known to prevent adhesion of proteins), as this detection zone acts as an internal negative reference (detection zone 1432); 2) a concentration-dependant signal in the detection zones modified with anti-human IgG, reflecting the binding of human IgG from the sample (detection zones 1434 and 1436); and 3) a constant signal in the detection zone modified with human IgG, which acts as an internal positive reference (detection zone 1438). These observations were expected.

Figure 25F:
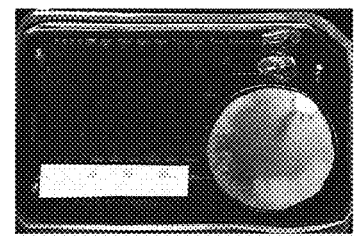

After removal of the fluid connector and the source of vacuum, the signals remained permanently bound to the device for direct observation or data storage (FIG. 25F).

While several embodiments of the present invention have been described and illustrated herein, those of ordinary skill in the art will readily envision a variety of other means and/or structures for performing the functions and/or obtaining the results and/or one or more of the advantages described herein, and each of such variations and/or modifications is deemed to be within the scope of the present invention. More generally, those skilled in the art will readily appreciate that all parameters, dimensions, materials, and configurations described herein are meant to be exemplary and that the actual parameters, dimensions, materials, and/or configurations will depend upon the specific application or applications for which the teachings of the present invention is/are used. Those skilled in the art will recognize, or be able to ascertain using no more than routine experimentation, many equivalents to the specific embodiments of the invention described herein. It is, therefore, to be understood that the foregoing embodiments are presented by way of example only and that, within the scope of the appended claims and equivalents thereto, the invention may be practiced otherwise than as specifically described and claimed. The present invention is directed to each individual feature, system, article, material, kit, and/or method described herein. In addition, any combination of two or more such features, systems, articles, materials, kits, and/or methods, if such features, systems, articles, materials, kits, and/or methods are not mutually inconsistent, is included within the scope of the present invention.

All definitions, as defined and used herein, should be understood to control over dictionary definitions, definitions in documents incorporated by reference, and/or ordinary meanings of the defined terms.

The indefinite articles "a" and "an," as used herein in the specification and in the claims, unless clearly indicated to the contrary, should be understood to mean "at least one."

It should also be understood that, unless clearly indicated to the contrary, in any methods claimed herein that include more than one step or act, the order of the steps or acts of the method is not necessarily limited to the order in which the steps or acts of the method are recited.

In the claims, as well as in the specification above, all transitional phrases such as "comprising," "including," "carrying," "having," "containing," "involving," "holding," "composed of," and the like are to be understood to be open-ended, i.e., to mean including but not limited to. Only the transitional phrases "consisting of" and "consisting essentially of" shall be closed or semi-closed transitional phrases, respectively, as set forth in the United States Patent Office Manual of Patent Examining Procedures, Section 2111.03.

What is claimed is:

1. A method, comprising:
    in a device including a microfluidic network containing a first plug comprising a first liquid and a second plug comprising a second liquid stored in one or more channels of the device, wherein the first and second plugs are separated by a fluid immiscible with the first and second liquids, and wherein a port of the one or more channels of the device is sealed, performing the steps of:
    unsealing the port;
    inserting both an inlet and an outlet of a sample introduction component containing a sample into ports of the device, wherein upon insertion, the inlet of the sample introduction component is downstream of the first and second plugs, and the outlet of the sample introduction component is upstream of a reaction area of the microfluidic network;

introducing the sample into the device downstream of the first and second plugs;

passing the sample across the reaction area of the microfluidic network;

passing at least a portion of the first liquid and/or the second liquid across the reaction area after the step of passing the sample across the reaction area;

absorbing at least a portion of the first liquid and at least a portion of the second liquid with an absorbent material contained in a liquid containment region positioned downstream of the reaction area and upstream of an outlet of the microfluidic network; and controlling a rate of flow of a liquid in the channel by applying a source of fluid flow to the channel, wherein the act of absorbing does not substantially control the flow rate of a liquid flowing in the channel upstream of the liquid containment region and wherein the rate of flow is at least 10 times greater than the rate of absorbing.

2. A method as in claim 1, wherein controlling the rate of flow of the liquid comprises applying a vacuum source to an outlet of the device.

3. A method as in claim 1, wherein controlling the rate of flow of the liquid comprises applying a positive pressure to an inlet of the device.

4. A method as in claim 1, wherein controlling a rate of flow of a liquid comprises controlling the rate of flow of the liquid upstream of the liquid containment region.

5. A method as in claim 1, wherein the fluid immiscible with the first and second liquids is a gas.

6. A method as in claim 5, further comprising allowing the gas to escape from the outlet of the device.

7. A method as in claim 6, wherein the gas escapes from the outlet of the device by flowing around the absorbent material.

8. A method as in claim 6, wherein the gas escapes from the outlet of the device by flowing through pores of the absorbent material.

9. A method as in claim 1, wherein the fluid immiscible with the first and second liquids is a third liquid.

10. A method as in claim 9, further comprising absorbing the third liquid with the absorbent material contained in the liquid containment region.

11. A method as in claim 1, wherein the total volume of liquids introduced into the device is less than the volume of the liquid containment region.

12. A method as in claim 1, wherein the total volume of liquids flowing in the device is less than the volume of the liquid containment region.

13. A method as in claim 1, wherein none of the liquid flowing in the device exits the device during use.

14. A method as in claim 1, wherein the microfluidic network does not include any channel intersections.

15. A method as in claim 1, wherein the liquid containment region comprises a first, hydrophilic absorbent material and a second, hydrophobic absorbent material.

16. A method as in claim 1, wherein the first and second liquids are aqueous solutions and the third liquid is hydrophobic.

17. A method as in claim 1, comprising absorbing substantially all of the liquid flowing in the device in the liquid containment region.

18. A method as in claim 1, wherein the liquid containment region is a waste reservoir.

19. A method, comprising:

in a device including a microfluidic network containing a first liquid comprising a first component for a chemical and/or biological reaction and a wash solution stored in one or more channels of the device, wherein a port of the one or more channels of the device is sealed, performing the steps of:

unsealing the port;

inserting both an inlet and an outlet of a sample introduction component containing a sample into ports of the device, wherein upon insertion, the inlet of the sample introduction component is downstream of the first and second plugs, and the outlet of the sample introduction component is upstream of a reaction area of the microfluidic network;

introducing the sample into the device downstream of the first liquid and wash solution;

passing the sample across a reaction area of the microfluidic network;

passing the wash solution across the reaction area after the step of passing the sample across the reaction area;

passing the first liquid across the reaction area after the step of passing the wash solution across the reaction area, and causing a chemical and/or biological reaction to occur between the first component contained in the first liquid and a second component immobilized at the reaction area;

absorbing at least a portion of the first liquid with an absorbent material contained in a liquid containment region positioned upstream of an outlet of the microfluidic network; and controlling a rate of flow of a liquid in the channel by applying a source of fluid flow to the channel, wherein the act of absorbing does not substantially control the flow rate of a liquid flowing in the channel upstream of the liquid containment region and wherein the rate of flow is at least 10 times greater than the rate of absorbing.

20. A method as in claim 1, wherein the device comprises a detector positioned downstream of the liquid containment region.

21. A method as in claim 1, wherein the absorbent material is not accessible via an outlet of the device.

22. A method as in claim 1, wherein a total volume occupied by the absorbent material prior to first use of the device, including the volume occupied by any pores present in the absorbent material, is less than 100% but greater than 40% of the volume of the liquid containment region.

23. A method as in claim 1, wherein the liquid containment region comprises a disinfectant stored therein prior to use of the device.

24. A method as in claim 1, wherein the first and second plugs are stored in the channel of the device prior to first use of the device.

25. A method as in claim 24, wherein the first and second plugs are not in fluid communication with the liquid containment region prior to first use of the device.

26. A method as in claim 20, wherein the detector is adapted and arranged such that upon detection of a liquid downstream of the liquid containment region, a signal is sent to a control system which can shut down or modulate a source of fluid flow that controls the rate of flow of liquids in the channel.

27. A method as in claim 1, comprising detecting a component contained in the first fluid and/or the second fluid at the reaction area using a detector associated with the reaction area.

28. A method as in claim 1, wherein the reaction area includes a first component immobilized therein, the method comprising causing a chemical and/or biological interaction to occur between the first component and a second component contained in the second liquid.

29. A method as in claim 28, wherein the first liquid comprises a wash solution, the method comprising passing the first liquid across the reaction area prior to the step of causing the chemical and/or biological interaction to occur.

30. A method as in claim 2, comprising applying the vacuum source at a constant pressure during the step of passing at least a portion of the first liquid and/or the second liquid across the reaction area and the absorbing step.

31. A method as in claim 1, wherein the microfluidic network comprises a connecting channel fluidly connecting the outlet with the liquid containing region, and wherein the connecting channel has a length of at least 1 cm.

32. A method as in claim 31, comprising trapping any of the first or second liquids exiting the liquid containment region in the connecting channel.

33. A method as in claim 19, wherein the microfluidic network comprises a connecting channel fluidly connecting the outlet with the liquid containing region, and wherein the connecting channel has a length of at least 1 cm.

34. A method as in claim 33, comprising trapping any of the first or second liquids exiting the liquid containment region in the connecting channel.

35. A method as in claim 1, wherein the liquid containment region is in fluidic communication with the outlet.

36. A method as in claim 19, wherein the liquid containment region is in fluidic communication with the outlet.

37. A method as in claim 1, wherein the step of introducing the sample into the device comprises transferring the sample from the sample introduction component to the device while the first and second plugs are substantially stationary.

38. A method as in claim 1, wherein the sample introduction component remains attached to the device during the steps of passing the sample and the first plug across the reaction area.

\* \* \* \* \*